United States Patent
Nishio et al.

(10) Patent No.: US 11,452,542 B2
(45) Date of Patent: Sep. 27, 2022

(54) MEDICAL DEVICE AND TREATMENT METHOD

(71) Applicant: TERUMO KABUSHIKI KAISHA, Tokyo (JP)

(72) Inventors: Kosuke Nishio, Irvine, CA (US); Tomonori Hatta, San Jose, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 203 days.

(21) Appl. No.: 16/138,024

(22) Filed: Sep. 21, 2018

(65) Prior Publication Data
US 2019/0021758 A1 Jan. 24, 2019

Related U.S. Application Data

(63) Continuation of application No. PCT/JP2017/010915, filed on Mar. 17, 2017.

(30) Foreign Application Priority Data

Mar. 23, 2016 (JP) .............................. JP2016-058362

(51) Int. Cl.
*A61B 17/32* (2006.01)
*A61B 17/3207* (2006.01)
*A61B 90/00* (2016.01)

(52) U.S. Cl.
CPC ............... *A61B 17/320725* (2013.01); *A61B 17/320758* (2013.01); *A61B 17/320783* (2013.01);
(Continued)

(58) Field of Classification Search
CPC ........... A61B 17/320758; A61B 2017/320004; A61B 2017/320716; A61B 2017/320741; A61B 2090/036
See application file for complete search history.

(56) References Cited

U.S. PATENT DOCUMENTS 3,886,943 A * 6/1975 Skiff ............... A61B 17/320708
606/159
4,887,613 A * 12/1989 Farr ............... A61B 17/320758
606/159
(Continued)

FOREIGN PATENT DOCUMENTS

JP 2013536740 A 9/2013
JP 2015213826 A 12/2015
(Continued)

OTHER PUBLICATIONS

International Search Report (PCT/ISA/210) daetd Jun. 13, 2017, by the Japanese Patent Office as the International Searching Authority for International Application No. PCT/JP2017/010915.
(Continued)

*Primary Examiner* — Alexander J Orkin
(74) *Attorney, Agent, or Firm* — Buchanan Ingersoll & Rooney PC

(57) ABSTRACT

A medical device and a treatment method are disclosed, which can improve safety by reducing damage to a biological tissue while an object inside a biological lumen can be cut. A medical device is disclosed for cutting an object inside a biological lumen includes a rotatable drive shaft, and a rotary structure that interlocks with a distal side of the drive shaft so as to be rotated by the drive shaft. The rotary structure has a cutting portion for cutting the object, and a non-cutting portion capable of smoothly coming into contact with a biological tissue. The non-cutting portion is located in a maximum outer diameter portion of the rotary structure.

17 Claims, 31 Drawing Sheets

(52) U.S. Cl.
CPC ............. *A61B 2017/320004* (2013.01); *A61B 2017/320032* (2013.01); *A61B 2017/320716* (2013.01); *A61B 2017/320741* (2013.01); *A61B 2017/320766* (2013.01); *A61B 2090/036* (2016.02); *A61B 2090/08021* (2016.02)

(56) References Cited

U.S. PATENT DOCUMENTS

| | | | | |
|---|---|---|---|---|
| 5,622,188 | A * | 4/1997 | Plaia | A61B 17/320725 |
| | | | | 128/898 |
| 6,146,395 | A | 11/2000 | Hirst | |
| 6,183,487 | B1 * | 2/2001 | Barry | A61B 17/320758 |
| | | | | 606/159 |
| 6,569,177 | B1 * | 5/2003 | Dillard | A61B 17/320758 |
| | | | | 606/168 |
| 6,579,298 | B1 * | 6/2003 | Bruneau | A61B 17/320758 |
| | | | | 606/159 |
| 7,252,674 | B2 | 8/2007 | Wyzgala et al. | |
| 2002/0151918 | A1 * | 10/2002 | Lafontaine | A61B 17/3207 |
| | | | | 606/159 |
| 2005/0273123 | A1 * | 12/2005 | Dongelmans | A61B 17/22012 |
| | | | | 606/159 |
| 2009/0099581 | A1 | 4/2009 | Kim et al. | |
| 2010/0010522 | A1 | 1/2010 | Shturman | |
| 2010/0168731 | A1 | 7/2010 | Wu et al. | |
| 2012/0143239 | A1 * | 6/2012 | Aklog | A61B 17/3207 |
| | | | | 606/200 |
| 2013/0158578 | A1 | 6/2013 | Ghodke et al. | |
| 2014/0100585 | A1 * | 4/2014 | Anderson | A61B 17/32 |
| | | | | 606/128 |
| 2015/0088246 | A1 * | 3/2015 | Astarci | A61B 17/320725 |
| | | | | 623/2.11 |
| 2016/0120565 | A1 | 5/2016 | Kobayashi et al. | |

FOREIGN PATENT DOCUMENTS

| | | |
|---|---|---|
| WO | 2015190578 A1 | 12/2015 |
| WO | 2016072107 A1 | 5/2016 |

OTHER PUBLICATIONS

Written Opinion (PCT/ISA/237) dated Jun. 13, 2017, by the Japanese Patent Office as the International Searching Authority for International Application No. PCT/JP2017/010915.

* cited by examiner

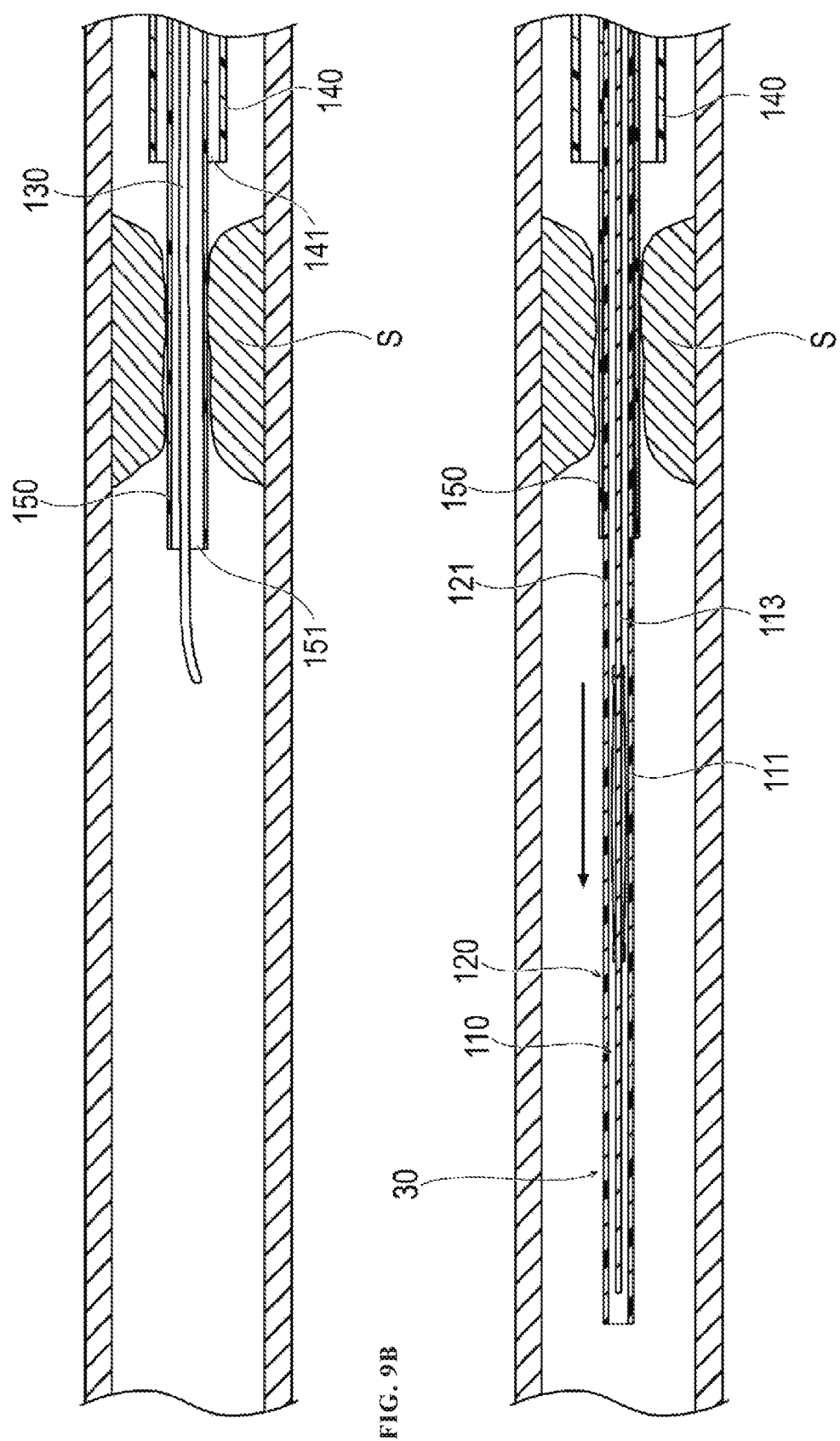

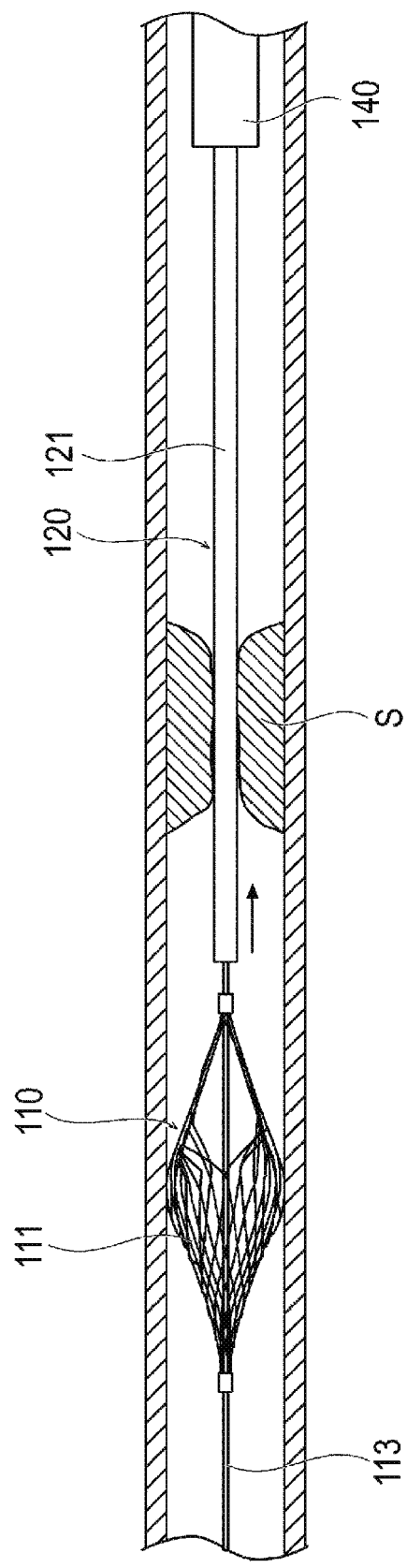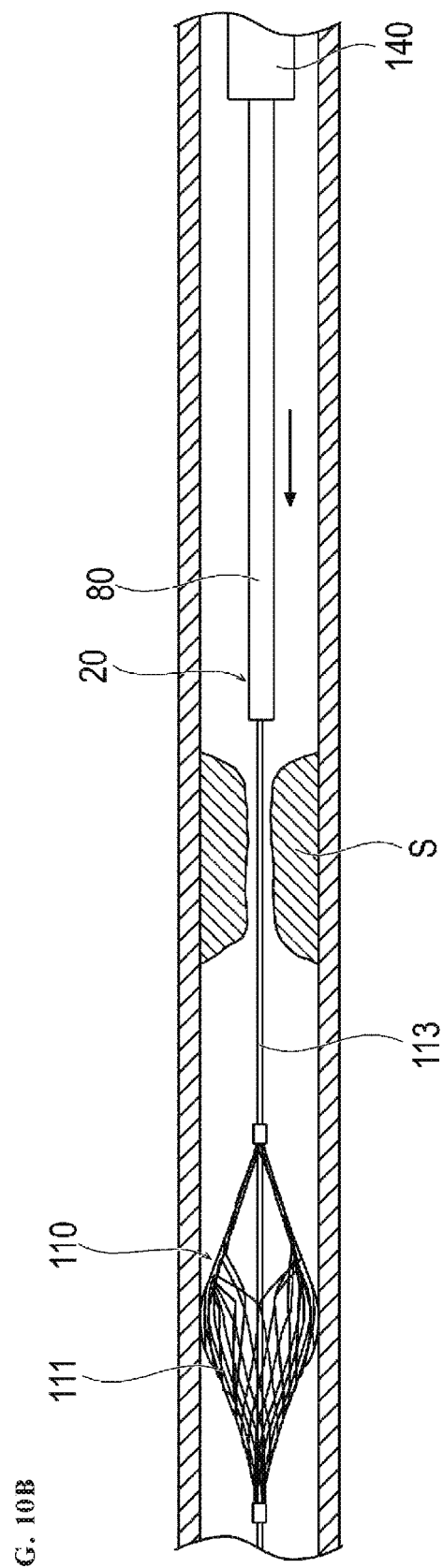

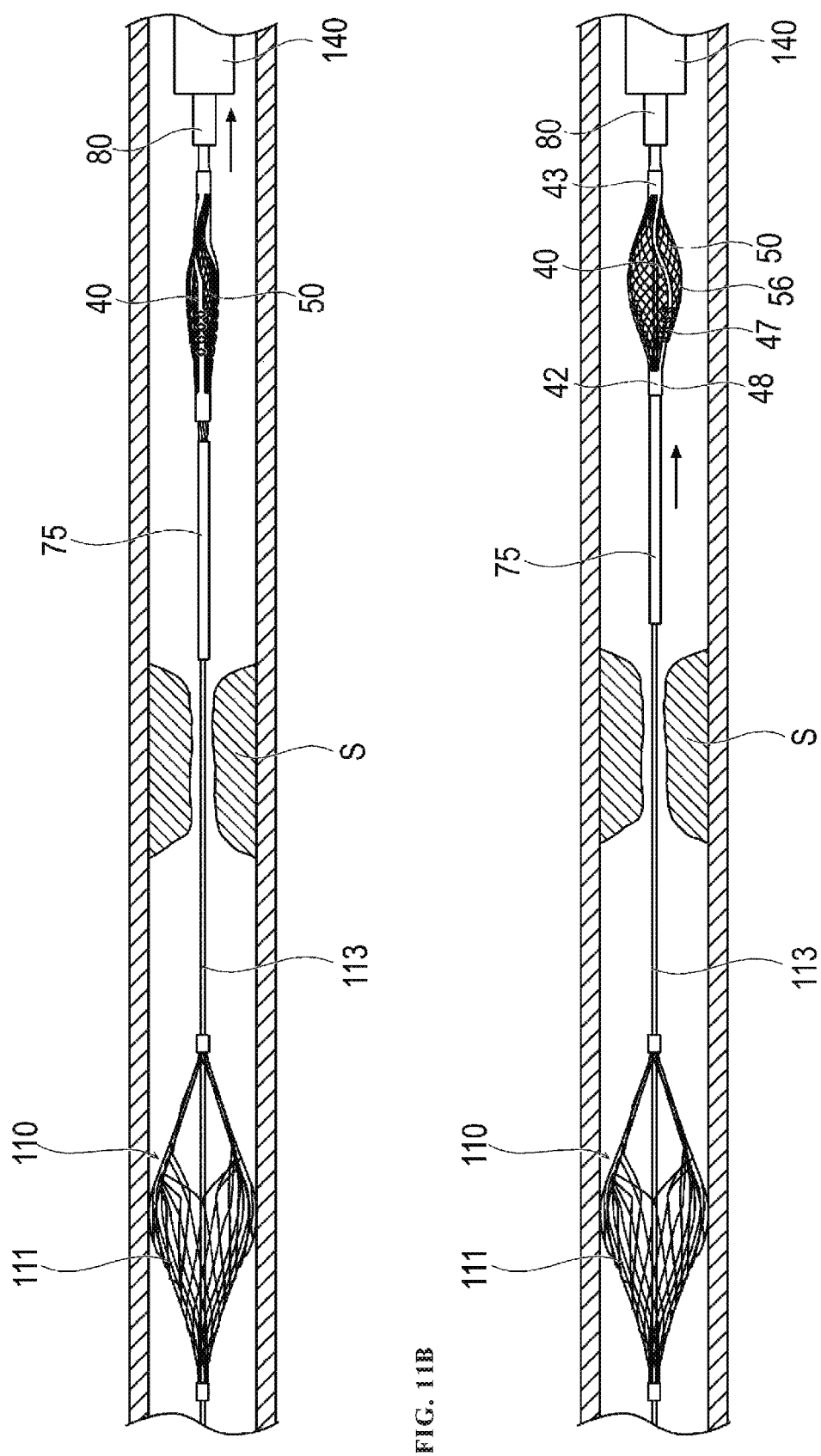

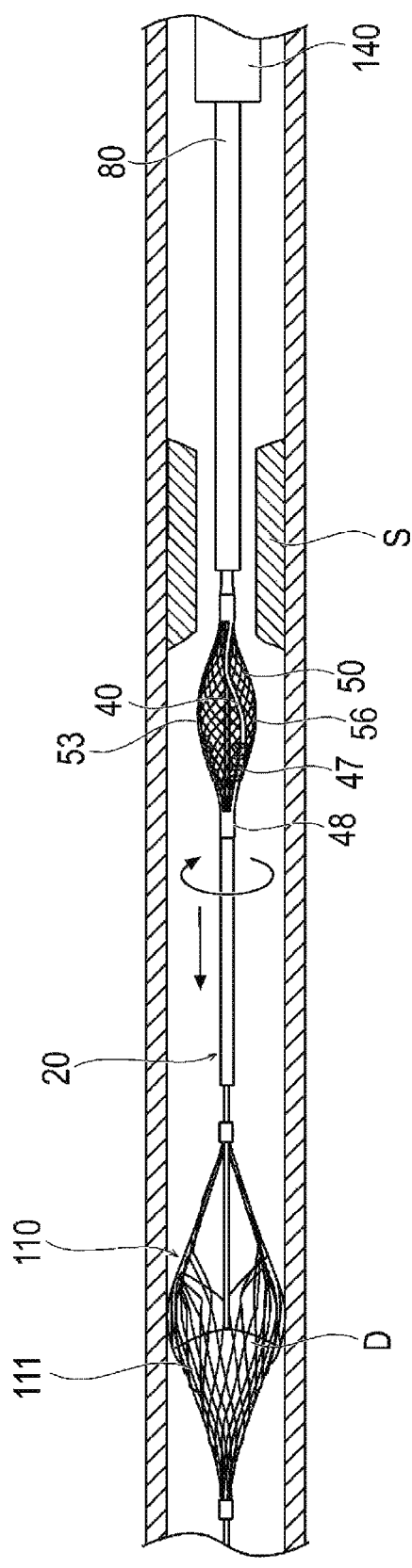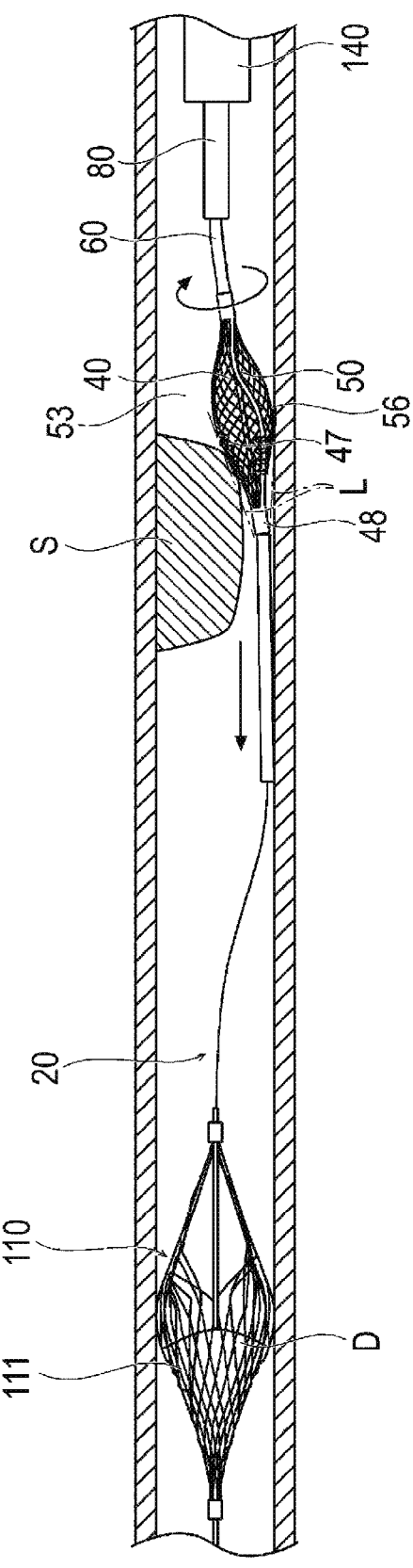
FIG. 12A
FIG. 12B

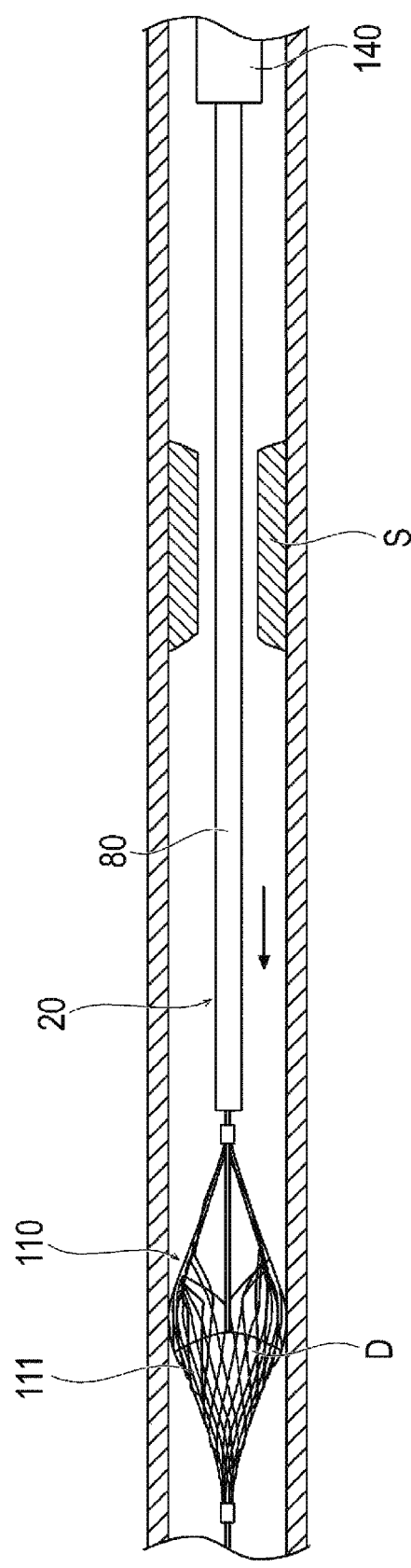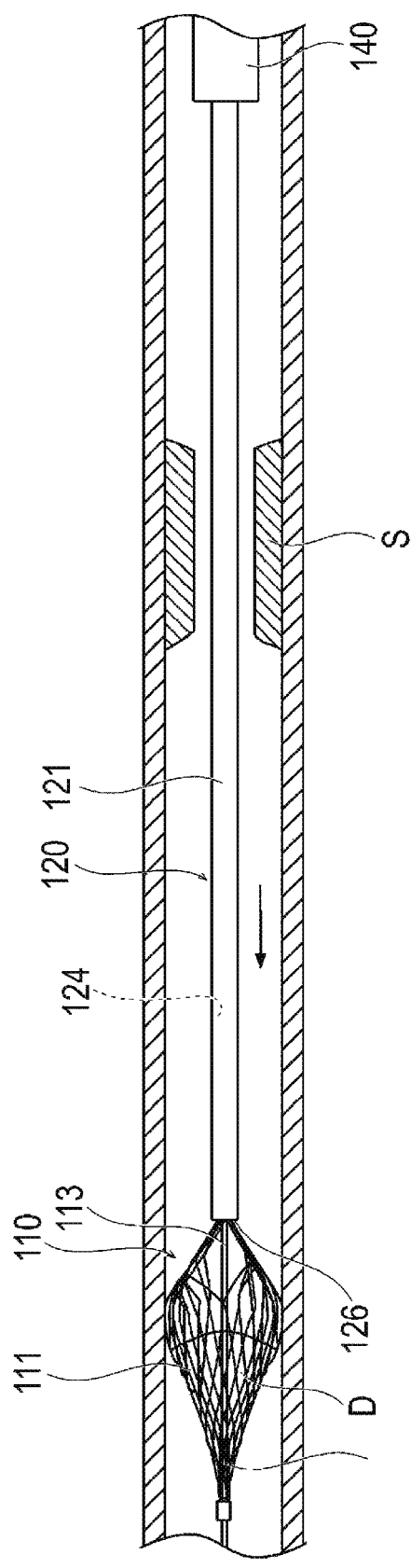

MEDICAL DEVICE AND TREATMENT METHOD

CROSS-REFERENCES TO RELATED APPLICATIONS

This application is a continuation of International Application No. PCT/JP2017/010915 filed on Mar. 17, 2017, which claims priority to Japanese Application No. 2016-058362 filed on Mar. 23, 2016, the entire content of both of which is incorporated herein by reference.

TECHNICAL FIELD

The present disclosure generally relates to a medical device and a treatment method for cutting an object from an inner wall surface of a biological lumen.

DESCRIPTION

A treatment method of a stenosed site caused by a plaque or a thrombus in a coronary artery includes percutaneous coronary angioplasty (PTCA) for dilating a blood vessel by using a balloon, or a method of causing a mesh-shaped or coil-shaped stent to indwell the blood vessel as a support for the blood vessel. However, these methods are less likely to be applicable to a case where the plaque of the stenosed site is calcified and hardened, or a case where the plaque appears in a bifurcated portion of the coronary artery. As a method of enabling the treatment even in these cases, atherectomy for cutting a stenosed substance such as the plaque and the thrombus is known.

As a device for performing the atherectomy, for example, U.S. Pat. No. 7,252,674 discloses the following device. The device cuts the stenosed substance by affixing diamond particles (polishing material) to an outer surface of a rotary body located in a distal portion of a catheter and rotating the rotary body inside the coronary artery. The rotary body of this device has four bars aligned in a circumferential direction. These bars are bent and protruded outward in a radial direction so as to be expandable in accordance with a blood vessel diameter.

The device disclosed in U.S. Pat. No. 7,252,674 has a possibility that the polishing material affixed to the rotary body may come into contact with a vascular wall in a case where the rotary body is inclined inside the blood vessel or in a case where the blood vessel is curved. Consequently, a risk of damage to a normal blood vessels increases.

SUMMARY OF INVENTION

A medical device and a treatment method are disclosed, which can improve relative safety by reducing damage to a biological tissue while an object inside a biological lumen can be cut.

A medical device is disclosed for cutting an object inside a biological lumen. The medical device includes a rotatable drive shaft, and a rotary structure that interlocks with a distal side of the drive shaft so as to be rotated by the drive shaft. The rotary structure has a cutting portion for cutting the object, and a non-cutting portion capable of smoothly coming into contact with a biological tissue. The non-cutting portion is located in a maximum outer diameter portion of the rotary structure.

A treatment method is disclosed for cutting an object inside a biological lumen by using the above-described medical device. The treatment method includes a step of inserting the rotary structure into the biological lumen, a step of causing the cutting portion to cut the object inside the biological lumen while the rotary structure is rotated and the non-cutting portion is brought into contact with the biological tissue, and a step of removing the rotary structure from the inside of the biological lumen.

According to the medical device configured as described above, the non-cutting portion is located in the maximum outer diameter portion of the rotary structure. Accordingly, while the rotating cutting portion effectively cuts the object inside the biological lumen, the non-cutting portion can help prevent the biological tissue from being damaged by the cutting portion. Therefore, relative safety can be improved by reducing damage to the biological tissue.

The non-cutting portion may have a first non-cutting portion which is larger than the cutting portion in a radial direction and which is capable of smoothly coming into contact with the biological tissue, and a second non-cutting portion which is located so as to interpose the cutting portion between the first non-cutting portion and the second non-cutting portion along an axial direction. The cutting portion may be located inside a tangential line between the first non-cutting portion and the second non-cutting portion in a cross section along the axial direction. According to the medical device configured as described above, the cutting portion is located inside the tangential line between the first non-cutting portion and the second non-cutting portion in the cross section along the axial direction. Accordingly, while the rotating cutting portion can properly cut the object inside the biological lumen, the relative safety can be improved by causing the first non-cutting portion and the second non-cutting portion to help prevent the cutting portion from coming into contact with the biological tissue and reducing the damage to the biological tissue.

At least one of the first non-cutting portion and the second non-cutting portion may be rotatable relative to the drive shaft. In this manner, friction can be reduced between the first non-cutting portion or the second non-cutting portion, and a wall of the biological lumen, the relative safety can be improved by reducing the damage to the biological tissue.

The medical device may further include an outer sheath which is capable of accommodating the drive shaft so as to be relatively rotatable, which is capable of covering a portion of the cutting portion, and whose outer peripheral surface has at least one of the first non-cutting portion and the second non-cutting portion. In this manner, at least one of the first non-cutting portion and the second non-cutting portion in the outer sheath which is not rotated together with the cutting portion is brought into contact with a living body. Therefore, the living body can be less affected by the cutting portion. Furthermore, at least one of the first non-cutting portion and the second non-cutting portion is not rotated together with the cutting portion. Accordingly, even if the cutting portion comes into contact with the living body, a rotational force is less likely to act on the living body. Therefore, the cutting portion can be held at a desired position.

The outer sheath may be movable relative to the drive shaft along the axial direction. In this manner, cutting conditions can be changed by moving the outer sheath relative to the cutting portion. In a case where the first non-cutting portion or the second non-cutting portion is disposed in the outer sheath, a position of the first non-cutting portion or the second non-cutting portion can be changed relative to the cutting portion, if necessary.

According to the treatment method configured as described above, in the cutting step, the non-cutting portion located in the maximum outer diameter portion of the rotary structure comes into contact with the biological tissue. Accordingly, while the rotating cutting portion effectively cuts the object inside the biological lumen, the non-cutting portion can help prevent the biological tissue from being damaged by the cutting portion. Therefore, the relative safety can be improved by reducing the damage to the biological tissue.

The non-cutting portion may have a first non-cutting portion which is larger than the cutting portion in a radial direction and which is capable of smoothly coming into contact with the biological tissue, and a second non-cutting portion which is located so as to interpose the cutting portion between the first non-cutting portion and the second non-cutting portion along an axial direction. In the cutting step, while maintaining a state where the cutting portion is located inside a tangential line between the first non-cutting portion and the second non-cutting portion in a cross section along the axial direction, the cutting portion may be rotated by the drive shaft so as to cut the object inside the biological lumen. According to the treatment method configured as described above, in the cutting step, the cutting portion is located inside the tangential line between the first non-cutting portion and the second non-cutting portion in the cross section along the axial direction. Accordingly, while the rotating cutting portion cuts the object in the biological lumen, the first non-cutting portion and the second non-cutting portion can prevent the cutting portion from coming into contact with the biological tissue. Therefore, the relative safety can be improved by reducing the damage to the biological tissue.

In the cutting step, the object may be cut while the rotary structure having the cutting portion is inclined inside the biological lumen. In this manner, the object inside the biological lumen can be cut in a wide range. Even if the rotary structure is inclined, the first non-cutting portion and the second non-cutting portion can help prevent the cutting portion from coming into contact with the biological tissue. Therefore, relative safety can be improved.

In the cutting step, a rotation center axis of the rotary structure may be moved so as to swing inside the biological lumen. In this manner, the object inside the biological lumen can be cut in a wide range by the cutting portion. Even if the rotary structure is moved so as to swing, the first non-cutting portion and the second non-cutting portion can help prevent the cutting portion from coming into contact with the biological tissue. Therefore, the relative safety can be improved.

In the cutting step, a proximal portion of an outer sheath which is capable of accommodating the drive shaft and whose distal portion is curved may be rotated so as to adjust a position and inclination of the rotary structure inside the biological lumen. In this manner, the proximal portion of the outer sheath is operated. Accordingly, the position and the inclination of the rotary structure inside the biological lumen can be rather easily adjusted, and depending on a situation, the rotary structure can be brought into a suitable state for cutting the object. Therefore, operability of the medical device can be improved.

In the cutting step, an outer sheath which is capable of accommodating the drive shaft may be moved relative to the rotary structure in the axial direction so as to adjust a position and inclination of the rotary structure inside the biological lumen. In this manner, the proximal portion of the outer sheath is operated. Accordingly, the position and the inclination of the rotary structure inside the biological lumen can be adjusted rather easily, and depending on a situation of the object inside the biological lumen that is being cut, the rotary structure can be brought into a suitable state for cutting the object. Therefore, the operability of the medical device can be improved.

In accordance with an aspect, a medical device is disclosed for cutting an object inside a biological lumen, the medical device comprising: a rotatable drive shaft; a rotary structure that interlocks with a distal side of the drive shaft so as to be rotated by the drive shaft; and the rotary structure having a cutting portion for cutting the object, and a non-cutting portion capable of coming into contact with a biological tissue, and wherein the non-cutting portion is located in a maximum outer diameter portion of the rotary structure.

In accordance with another aspect, a medical device for cutting an object inside a biological lumen, the medical device comprising: a rotatable drive shaft; a rotary structure that interlocks with a distal side of the drive shaft so as to be rotated by the drive shaft, the rotary structure having a cutting portion for cutting the object, and a non-cutting portion capable of coming into contact with a biological tissue; and the non-cutting portion being located in a maximum outer diameter portion of the rotary structure and comprises a plurality of plates arrayed parallel to each other outside the rotary structure in a circumferential direction, and wherein in an axially orthogonal axial cross section, the plurality of plates is formed in an arc shape, and wherein each of the plurality of plates is fixedly attached to an outer peripheral surface of a proximal end portion of the rotary structure.

In accordance with an aspect, a treatment method for cutting an object inside a biological lumen with a medical device, the medical device including a rotatable drive shaft, a rotary structure that interlocks with a distal side of the drive shaft so as to be rotated by the drive shaft, and the rotary structure having a cutting portion for cutting the object, and a non-cutting portion capable of coming into contact with a biological tissue, and wherein the non-cutting portion is located in a maximum outer diameter portion of the rotary structure, the method comprising: inserting the rotary structure into the biological lumen; and causing the cutting portion to cut the object inside the biological lumen while the rotary structure is rotated and the non-cutting portion is brought into contact with the biological tissue.

BRIEF DESCRIPTION OF THE DRAWINGS

FIGS. 3A-3C are plan views illustrating a distal portion of the treatment device according to the first embodiment, and wherein FIG. 3A illustrates a state where the cutting portion is accommodated in an outer sheath, FIG. 3B illustrates a state where the contracted cutting portion protrudes from the outer sheath, and FIG. 3C illustrates a state where the cutting portion protruding from the outer sheath is expanded.

FIGS. 4A-4B are longitudinal sectional views illustrating the distal portion of the treatment device according to the first embodiment, and wherein FIG. 4A illustrates a state where the cutting portion is contracted, and FIG. 4B illustrates a state where the cutting portion is expanded.

FIGS. 6A and 6B are views illustrating the treatment device in an expanded state, and wherein FIG. 6A is a cross-sectional view taken along line VIA-VIA in FIG. 3C, and FIG. 6B is a cross-sectional view taken along line VIB-VIB in FIG. 3C.

FIGS. 8A and 8B are schematic cross-sectional views illustrating an intravascular state when a medical procedure is performed, and wherein FIG. 8A illustrates a state when a guide wire is inserted into a blood vessel, and FIG. 8B illustrates a state when a guiding catheter is inserted into the blood vessel.

FIGS. 9A and 9B are schematic cross-sectional views illustrating an intravascular state when the medical procedure is performed, and wherein FIG. 9A illustrates a state when a support catheter is inserted into a stenosed site, and FIG. 9B illustrates a state when the collecting device is inserted into the blood vessel.

FIGS. 10A and 10B are schematic cross-sectional views illustrating an intravascular state when the medical procedure is performed, and wherein FIG. 10A illustrates a state when a filter portion is expanded, and FIG. 10B illustrates a state where the treatment device is inserted into the blood vessel.

FIGS. 11A and 11B are schematic cross-sectional views illustrating an intravascular state when the medical procedure is performed, and wherein FIG. 11A illustrates a state when the cutting portion and a support portion are exposed in the treatment device, and FIG. 11B illustrates a state when the cutting portion and the support portion are expanded.

FIGS. 12A and 12B are schematic cross-sectional views illustrating an intravascular state when the medical procedure is performed, and wherein FIG. 12A illustrates a state when a stenosed substance is cut by the treatment device, and FIG. 12B illustrates a state where the stenosed substance is cut in a state where a rotary structure is inclined inside the blood vessel.

FIGS. 13A and 13B are schematic cross-sectional views illustrating an intravascular state when the medical procedure is performed, and wherein FIG. 13A illustrates a state where the cutting portion is accommodated in the outer sheath, and FIG. 13B illustrates a state where a debris collected by the filer portion is aspirated by a catheter.

FIGS. 14A and 14B are plan views illustrating a treatment device of a medical device according to a second embodiment, and wherein FIG. 14A illustrates a state where a contracted cutting portion protrudes from an outer sheath, and FIG. 14B illustrates a state where the cutting portion protruding from the outer sheath is expanded.

FIGS. 17A and 17B are plan views illustrating a treatment device of a medical device according to a third embodiment, and wherein FIG. 17A illustrates a state where an expandable portion of an outer sheath is contracted, and FIG. 17B illustrates a state where the expandable portion of the outer sheath is expanded.

FIGS. 18A and 18B are views illustrating the medical device according to the third embodiment, wherein FIG. 18A is a cross-sectional view taken along line XVIIIA-XVIIIA in FIG. 17A, and FIG. 18B is a cross-sectional view taken along line XVIIIB-XVIIIB in FIG. 17B.

FIGS. 19A and 19B are schematic cross-sectional views illustrating an intravascular state when a medical procedure is performed using the medical device according to the third embodiment, wherein FIG. 19A illustrates a state where a stenosed substance is cut by causing a rotary structure to protrude from the outer sheath, and FIG. 19B illustrates a state where the stenosed substance is cut by accommodating a proximal portion of the rotary structure in the outer sheath.

FIGS. 22A and 22B are schematic cross-sectional views illustrating an intravascular state when a medical procedure is performed using the medical device according to the fourth embodiment, wherein FIG. 22A illustrates a state where a stenosed substance is cut by causing a rotary structure to protrude from an outer sheath, and FIG. 22B illustrates a state where the stenosed substance is cut by accommodating a proximal portion of the rotary structure in the outer sheath.

FIGS. 25A-25C are plan views illustrating the medical device according to the fifth embodiment, wherein FIG. 25A illustrates a first modification example, FIG. 25B illustrates a second modification example, and FIG. 25C illustrates a third modification example.

FIGS. 27A and 27B are views illustrating a treatment device of a medical device according to a sixth embodiment, wherein FIG. 27A is a plan view, and FIG. 27B is a cross-sectional view taken along line XXVIIB-XXVIIB in FIG. 27A.

FIGS. 29A and 29B are plan views illustrating a medical device according to a seventh embodiment, wherein FIG. 29A illustrates a first example, and FIG. 29B illustrates a modification example.

FIGS. 34A and 34B are plan views illustrating the treatment device of the medical device according to the tenth embodiment, wherein FIG. 34A illustrates a first state, and FIG. 34B illustrates a second state.

FIGS. 41A and 41B are schematic cross-sectional views illustrating an intravascular state when a medical procedure is performed using the medical device according to the fourteenth embodiment, wherein FIG. 41A illustrates a state where a stenosed substance is cut by a proximal cutting portion exposed from an opening portion of an outer sheath, and FIG. 41B illustrates a state where the stenosed substance is cut by changing a direction of the opening portion of the outer sheath.

FIGS. 44A and 44B are schematic cross-sectional views illustrating an intravascular state when a medical procedure is performed using the medical device according to the fifteenth embodiment, wherein FIG. 44A illustrates a state where a stenosed substance is pressed and cut, and FIG. 44B illustrates a state where the stenosed substance is pulled and cut.

DESCRIPTION OF EMBODIMENTS

Figure 1:
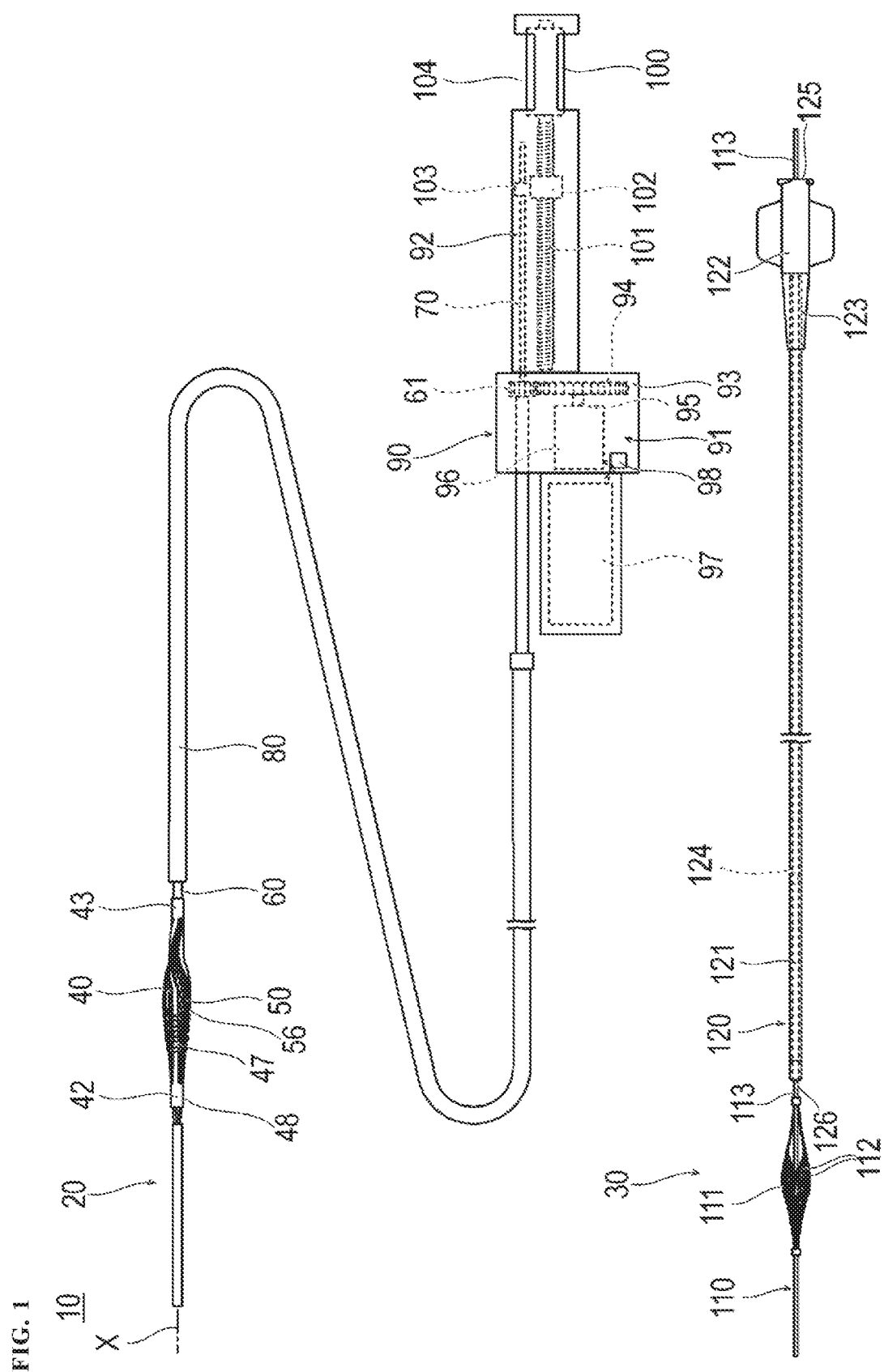
FIG. 1 is a plan view illustrating a state where a cutting portion is contracted in a medical device according to a first embodiment.

Hereinafter, embodiments according to the present disclosure will be described with reference to the drawings. Dimensional proportions in the drawings are exaggerated and different from actual proportions for convenience of description, in some cases.

First Embodiment

A medical device 10 according to a first embodiment of the present disclosure is used for therapy (treatment) for cutting a stenosed site or an occluded site caused by a plaque or a thrombus inside a blood vessel. In the description herein, a side of the device which is inserted into the blood vessel will be referred to as a "distal side", "distal", or "distal end", and a side of an operating hand (i.e., the side operated by an operator) will be referred to as a "proximal side", "proximal", or "proximal end".

As illustrated in FIG. 1, the medical device 10 according to the first embodiment of the present disclosure includes a treatment device 20 for cutting the stenosed site or the occluded site, and a collecting device 30 for collecting a debris scraped off and falling from the stenosed site or the occluded site.

Figure 2:
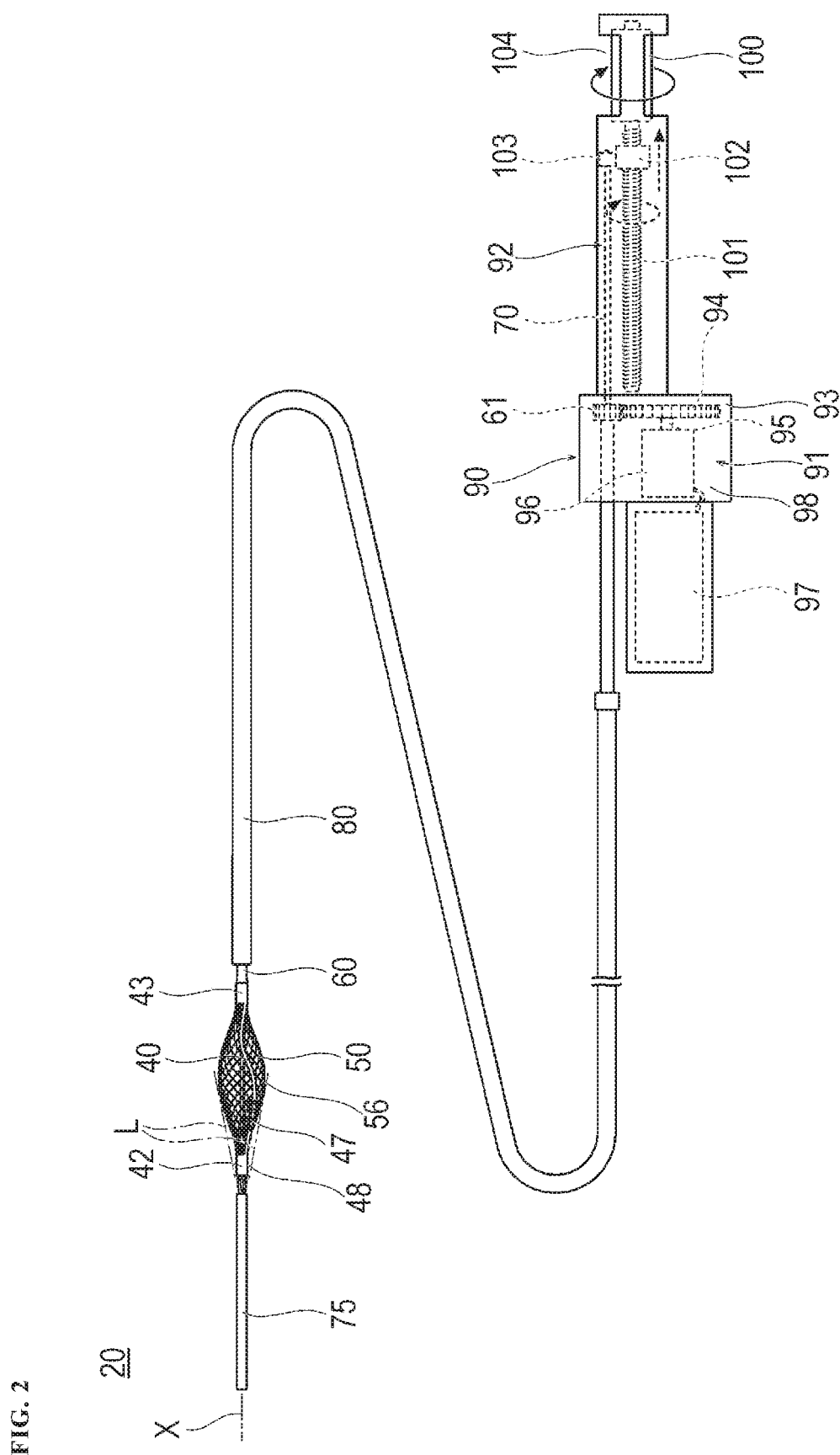
FIG. 2 is a plan view illustrating a state where the cutting portion is expanded in a treatment device according to the first embodiment.
Figure 3:
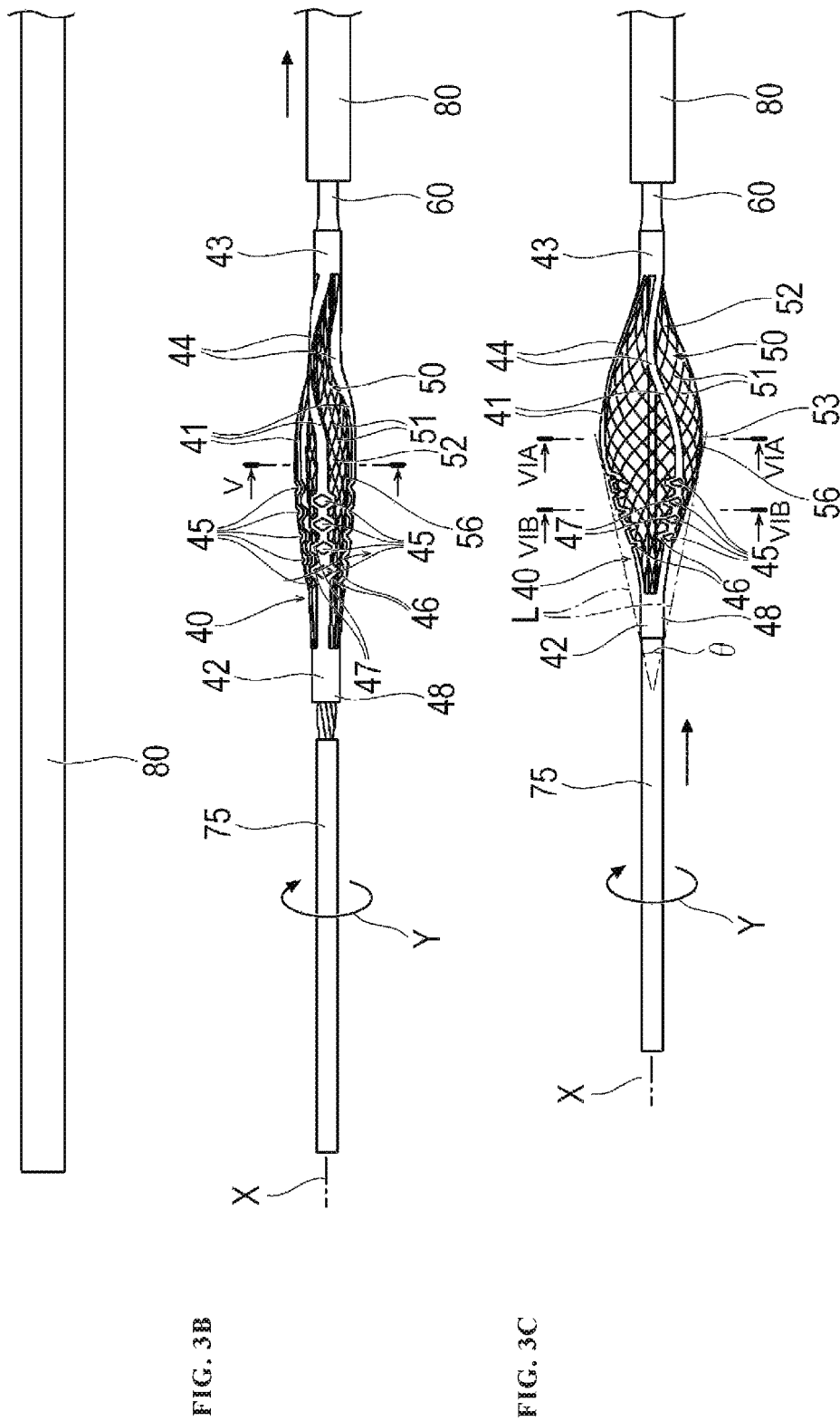
Figure 4:
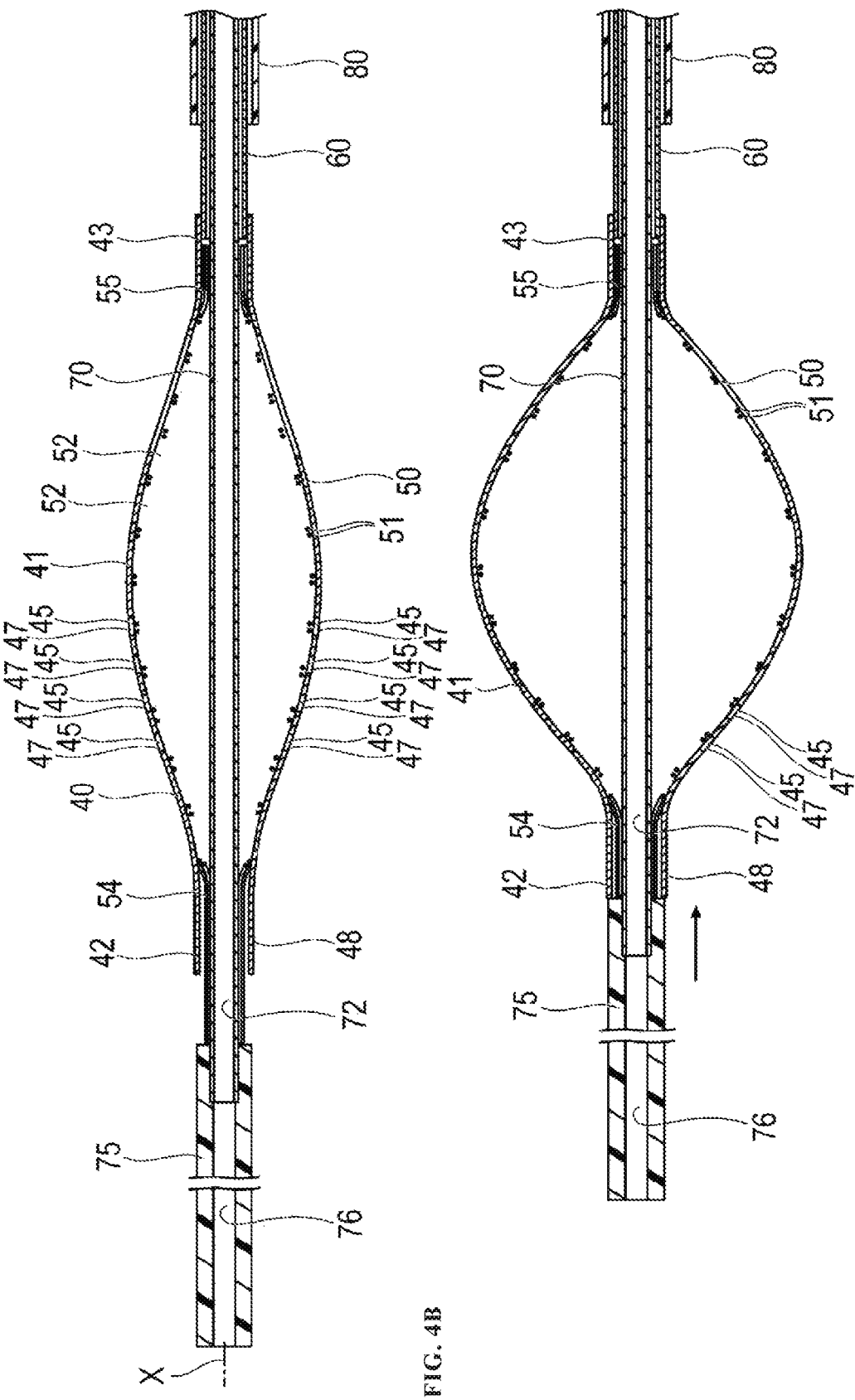
Figure 5:
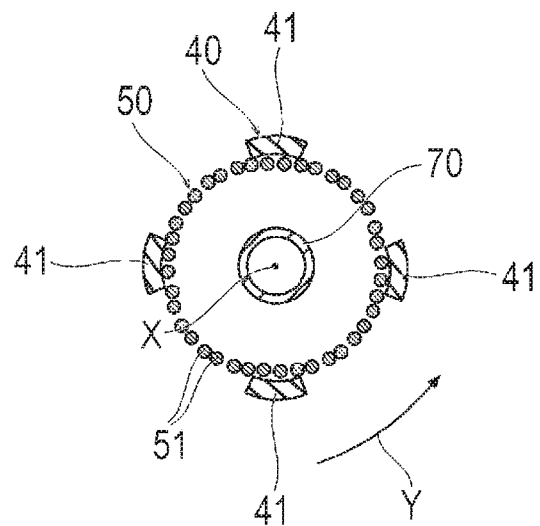
FIG. 5 is a cross-sectional view taken along line V-V in FIG. 3B.

As illustrated in FIGS. 1 and 2, the treatment device 20 includes a rotary structure 40 capable of expanding and contracting outward in a radial direction, a support portion 50 for supporting the rotary structure 40, a drive shaft 60 for rotating the rotary structure 40, a linear motion shaft 70 for adjusting a deformation amount of the rotary structure 40, a distal tube 75 interlocking with a distal side of the linear motion shaft 70, an outer sheath 80 capable of accommodating the rotary structure 40, and an operation unit 90 disposed on the hand side (i.e., proximal side) for operation.

As illustrated in FIGS. 3 to 6B, the rotary structure 40 includes at least one (four in the present embodiment) strut 41 extending along a rotation axis X of the drive shaft 60, a tubular distal end portion 42 formed integrally with the strut 41 on a distal side of all of the struts 41, and a tubular proximal end portion 43 formed integrally with the strut 41 on the proximal side of all of the struts 41. Without being fixed to the support portion 50 and the linear motion shaft 70, the tubular distal end portion 42 is movable relative to the support portion 50 and the linear motion shaft 70 in an axial direction. The linear motion shaft 70 moves relative to the rotary structure 40 in a proximal direction so that the tubular distal end portion 42 comes into contact with a proximal portion of the distal tube 75 interlocking (i.e., connecting or engaging) with the linear motion shaft 70. The tubular distal end portion 42 and the tubular proximal end portion 43 are moved closer to each other in a substantially linearly contracted state (refer to FIGS. 3B, 4A, and 5). In this manner, the strut 41 is deformed so as to be bent outward in a radial direction, and can be brought into an expanded state (refer to FIGS. 3C, 4B, and 6).

The proximal side of the strut 41 has an inclined portion 44 which is curved so as to be inclined relative to the rotation axis X in a contracted state. The distal side of the strut 41 has a plurality of opening portions 45 penetrating the inner peripheral surface from the outer peripheral surface. The strut 41 has a wide portion 46 which is relatively wider in a circumferential direction (rotation direction Y) than a portion adjacent to the wide portion 46, and an opening portion 45 is formed in each wide portion 46. The plurality of (four or five in the present embodiment) opening portion 45 are formed along an extending direction of the strut 41. An inner edge portion of the opening portion 45 functions as a cutting portion 47, which is a cutting edge for cutting the stenosed site or the occluded site. A position for forming the cutting portion 47 of the strut 41 is located closer to the distal side than a portion where the outer diameter of the strut 41 is maximum (substantially central portion along the rotation axis X) in an expanded state. It is preferable that an edge portion of the strut 41, other than an inner edge portion, which forms the cutting edge of the cutting portion 47, is subjected to chamfering.

In the strut 41, four opening portions 45 and five opening portions 45 are alternately arranged in the circumferential direction. Therefore, when the rotary structure 40 is cut out from one tubular body, for example, by means of laser processing or machining, the four opening portions 45 and the five opening portions 45 can be alternately shifted and arranged, and the opening portion 45 can obtain a proper width. In addition, the cutting portions 47 of the strut 41 which are adjacent to each other in the circumferential direction are shifted and arranged, thereby helping prevent a predetermined portion from being unevenly cut off. Accordingly, the stenosed site or the occluded site can be effectively cut.

Figure 6A:
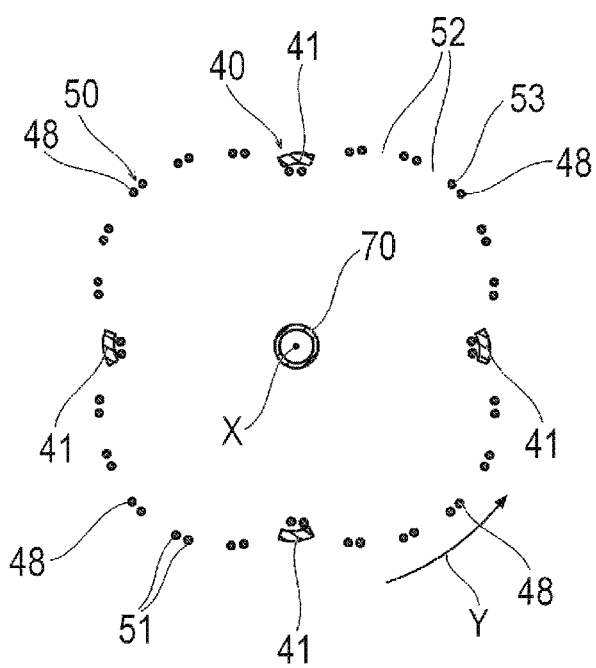
Figure 6B:
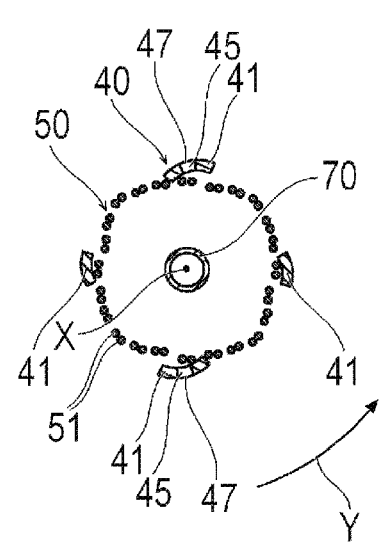

If the strut 41 is brought into an expanded state, an outer peripheral surface of a portion having the cutting portion 47 is deformed so as to be inclined inward in the radial direction on the side in the rotation direction Y (refer to FIG. 6B). Therefore, when the strut 41 is rotated in an extended state, a side inclined inward in the radial direction of the strut 41 first comes into smooth contact with a contact target smoothly. In this manner, excessive damage to a biological tissue can be reduced. In addition, the strut 41 is formed by being cut out from a tubular body having a diameter smaller than a diameter in an expanded state. Accordingly, the radius of curvature of the outer peripheral surface of the strut 41 is smaller than a distance from the rotation axis X to the outer peripheral surface of the strut 41 in the expanded state. Therefore, the edge portion of the strut 41 is much less likely to come into contact with the contact target. Accordingly, the excessive damage to the biological tissue can be further reduced.

The rotary structure 40 material, for example, may preferably be a shape memory alloy or stainless steel, which is provided with a shape memory effect or super-elasticity by means of heat treatment. The shape memory alloy can be a Ni—Ti system, a Cu—Al—Ni system, and a Cu—Zn—Al system, or a combination of the shape memory alloys, and a shape memory alloy is preferably used for the material of the rotary structure 40.

The support portion 50 is located so as to support the rotary structure 40 on the inside in the radial direction of the rotary structure 40. The support portion 50 can be a plurality of wire rods 51, for example, the plurality of wire rods 51 can be braided. In this manner, the support portion 50 is formed in a tubular shape having a gap 52 between the wire rods 51. In a distal side portion 54 of the support portion 50, the plurality of wire rods 51 are assembled to each other into a tubular shape. Without being fixed to an inner surface of the distal side portion 54 of the rotary structure 40, the distal side portion 54 is fixed to outer peripheral surface of the linear motion shaft 70 (refer to FIGS. 4A and 4B). In a proximal side portion 55 of the support portion 50, the plurality of wire rods 51 are assembled to each other into a tubular shape. The proximal side portion 55 is fixed to the inner peripheral surface of the proximal end portion 43 of the strut 41.

In the support portion 50, the distal end portion 42 and the proximal end portion 43 are moved close to each other in a contraction state (refer to FIGS. 3B and 4A) of the support portion 50 in a tubular shape having substantially a uniform outer diameter. In this manner, the central portion of the support portion 50 can be brought into an expanded state (refer to FIGS. 3C and 4B) after being deformed so as to be bent outward in the radial direction.

In the expanded state, a maximum expandable portion 53 whose outer diameter is largest in the support portion 50 protrudes outward in the radial direction between the struts 41 so as to increase a gap (or space) between the struts 41 in the expanded state (refer to FIG. 6A). Therefore, in the expanded state, a portion which is likely to come into contact with the biological tissue by spreading most outward of the strut 41 in the expanded state is located inside the maximum expandable portion 53 of the support portion 50 in the radial direction. In this manner, a normal biological tissue can be prevented from being damaged by the edge portion of the strut 41.

Then, a portion in the vicinity of the cutting edge 47 of the strut 41 has a short gap (or space) from the rotation axis X (diameter is small), and has the wide portion 46. Accordingly, the gap between the struts 41 is relatively narrow. Therefore, the support portion 50 located in the vicinity of the cutting edge 47 is prevented from protruding from between the struts 41 outward in the radial direction. Accordingly, without being hindered by the support portion 50, the cutting edge 47 can be brought into the contact target (refer to FIG. 6B).

As illustrated in FIG. 3C, the substantially central portion in the axial direction of the support portion 50 has a first non-cutting portion 56 which can come into relatively smooth contact with the biological tissue without cutting the biological tissue in a state where the rotary structure 40 and the support portion 50 are expanded. The first non-cutting portion 56 includes substantially the central portion of the support portion 50. In addition, the distal end portion 42 of the rotary structure 40 has a second non-cutting portion 48 which can come into relatively smooth contact with the biological tissue without cutting the biological tissue in a state where the rotary structure 40 is expanded. Then, in a state where the rotary structure 40 and the support portion 50 are expanded, the cutting portion 47 is located inside a tangential line L between the first non-cutting portion 56 and the second non-cutting portion 48 in a cross section along the axial direction.

Although not particularly limited, it is preferable, for example, that an angle θ formed by two tangential lines L located opposite to each other at 180 degrees is equal to or smaller than 90 degrees. When the angle θ is equal to or smaller than 90 degrees, compared to a case where the angle θ exceeds 90 degrees, a shape sharply protruding to the distal side is obtained. Accordingly, it is possible to efficiently and quickly cut the object inside the living body without applying a strong pushing load, and safety can be relatively ensured by the first non-cutting portion 56 and the second non-cutting portion 48.

In accordance with an exemplary embodiment, it is preferable that the wire rod 51 has a rigidity lower than that of the strut 41 and the wire rod 51 has a corner portion with curvature in a cross section so as not to damage the biological tissue with which the wire rod 51 comes into contact. In accordance with an exemplary embodiment, it is more preferable that the cross section of the wire rod 51 has a circular shape.

The outer diameter of the wire rod 51 can be appropriately selected depending on a material or application conditions of the wire rod 51. For example, the outer diameter of 0.05 mm to 0.15 mm may be selected.

The wire rod 51 material is preferably a flexible material. For example, the wire rod 51 material is preferably a shape memory alloy for which a shape memory effect or super-elasticity is provided by means of heat treatment, stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide. For example, the shape memory alloy is preferably a Ni—Ti system, a Cu—Al—Ni system, and a Cu—Zn—Al system, or a combination of the shape memory alloys. For example, a structure obtained by combining a plurality of materials to each other includes a structure obtained by coating the core wire made of Pt coated with a Ni—Ti alloy to provide a contrasting property, or a structure obtained by performing gold plating on the core wire made of the Ni—Ti alloy.

In accordance with an exemplary embodiment, for example, some of the plurality of wire rods 51 can include an X-ray contrast material. In this manner, a position and an expanded diameter of the support portion 50 and the rotary structure 40 can be precisely recognized under X-ray fluoroscopy, thereby facilitating a medical procedure. For example, as the X-ray contrast material, gold, platinum, a platinum-iridium alloy, silver, stainless steel, molybdenum, tungsten, tantalum, palladium, or an alloy of the material is preferably used. In addition, instead of the support portion 50, a portion of the rotary structure 40 may be formed of the X-ray contrast material. For example, the inner peripheral surface of the rotary structure 40 may be coated with the X-ray contrast material by means of plating. In this manner, the position and the expanded diameter of the support portion 50 and the rotary structure 40 can be precisely recognized under the X-ray fluoroscopy, thereby facilitating the medical procedure.

The inner diameter in a contracted state of the rotary structure 40 can be appropriately selected in accordance with the inner diameter of the biological lumen to be applied. For example, the inner diameter of the rotary structure 40 can be 0.9 mm to 1.6 mm. As an example, the inner diameter of the rotary structure 40 can be 1.4 mm. The outer diameter in a contracted state of the rotary structure 40 can be appropriately selected in accordance with the inner diameter of the biological lumen to be applied. For example, the outer diameter of the rotary structure 40 can be 1.1 mm to 1.8 mm. As an example, the outer diameter of the rotary structure 40 can be 1.7 mm. The length along the rotation axis X of the rotary structure 40 can be appropriately selected in accordance with the length of the biological lumen to be applied. For example, the length of the rotary structure 40 can be 10 mm to 30 mm. As an example, the length of the rotary structure 40 can be 20 mm.

The maximum outer diameter in an expanded state of the rotary structure 40 can be appropriately selected in accordance with the inner diameter of the biological lumen to be applied. For example, the maximum outer diameter of the rotary structure 40 can be 3.0 mm to 8.0 mm. As an example, the maximum outer diameter of the rotary structure can be 7.0 mm.

The length of the maximum expandable portion 53 (first non-cutting portion 56) of the support portion 50 in an expanded state, which protrudes outward in the radial direction from the strut 41, can be appropriately set. For example, the length of the maximum expandable portion 53 can be 0.05 mm to 0.5 mm. As an example, the length of the maximum expandable portion 53 can be 0.2 mm.

As illustrated in FIGS. 1 to 4, the drive shaft 60 is formed in a tubular shape. The distal side of the drive shaft 60 is fixed to the proximal end portion 43 of the rotary structure 40, and a driven gear 61 is fixed to the proximal side of the drive shaft 60. The proximal portion of the drive shaft 60 rotatably interlocks with a casing 91 of the operation unit 90.

The drive shaft 60 is preferably flexible, and moreover, has a characteristic in that rotation power acting from the proximal side can be transmitted to the distal side. For example, the drive shaft 60 is a tubular body having a shape of a multilayer coil such as a three-layer coil in which the coils are alternately wound in rightward, leftward, and rightward directions, and those in which a reinforcement member such as a wire rod is incorporated in a polyolefin such as polyethylene and polypropylene, polyester such as polyamide and polyethylene terephthalate, a fluorine-based polymer such as ETFE, polyether ether ketone (PEEK), polyimide, or a combination of polyolefin, polyester, and/or a fluorine-based polymer.

The inner diameter of the drive shaft 60 can be appropriately selected. For example, the inner diameter of the drive shaft 60 can be 0.7 mm to 1.4 mm. As an example, the inner diameter of the drive shaft can be 1.2 mm. The outer diameter of the drive shaft 60 can be appropriately selected. For example, the outer diameter of the drive shaft 60 can be 0.8 mm to 1.5 mm. As an example, the inner diameter of the drive shaft 60 can be 1.35 mm.

The linear motion shaft 70 is a tubular body movable relative to the drive shaft 60 in the direction of the rotation axis X in order to expand and contract the rotary structure 40 and the support portion 50, and penetrates the drive shaft 60, the rotary structure 40, and the support portion 50. The distal side of the linear motion shaft 70 is fixed to the distal side portion 54 of the wire rod 51, and the proximal side of the linear motion shaft 70 is connected to a movement mechanism 92 which linearly moves the linear motion shaft 70 along the rotation axis X. The linear motion shaft 70 internally has a lumen 72 into which a guide wire can be inserted.

The linear motion shaft 70 material is preferably a flexible material. For example, the linear motion shaft 70 material can be a shape memory alloy for which a shape memory effect or super-elasticity is provided by means of heat treatment, stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide. For example, the shape memory alloy is preferably a Ni—Ti system, a Cu—Al—Ni system, and a Cu—Zn—Al system, or a combination of the shape memory alloys. In addition, the linear motion shaft 70 may be formed of a plurality of materials, and the reinforcement member such as the wire rod may be incorporated in the plurality of materials of the linear motion shaft 70.

The inner diameter of the linear motion shaft 70 can be appropriately selected. For example, the inner diameter of the linear motion shaft 70 can be 0.5 mm to 1.2 mm. As an example, the inner diameter of the linear motion shaft 70 can be 0.95 mm. The outer diameter of the linear motion shaft 70 can be appropriately selected. For example, the outer diameter of the linear motion shaft 70 can be 0.6 mm to 1.3 mm. As an example, the outer diameter of linear motion shaft can be 1.05 mm.

The outer sheath 80 is a tubular body covering the outer side of the drive shaft 60, and is movable and rotatable relative to the drive shaft 60 in the direction along the rotation axis X. The outer sheath 80 can be operated by gripping the proximal portion, and the outer sheath 80 is moved to the distal side. In this manner, the rotary structure 40 and the support portion 50 in a contracted state can be accommodated inside the outer sheath 80. If the outer sheath 80 is moved to the proximal side, the rotary structure 40 and the support portion 50 can be exposed outward.

The outer sheath 80 material is not particularly limited. However, for example, the outer sheath 80 material can preferably be polyolefin such as polyethylene and polypropylene, polyester such as polyamide and polyethylene terephthalate, a fluorine-based polymer such as ETFE, polyether ether ketone (PEEK), or polyimide. In addition, the outer sheath 80 may be formed of a plurality of materials, and the reinforcement member such as the wire rod may be incorporated in the plurality of materials of the outer sheath 80.

The inner diameter of the outer sheath 80 can be appropriately selected. For example, the inner diameter is of the outer sheath 80 can be 1.2 mm to 1.9 mm. As an example, the inner diameter of the outer sheath can be 1.8 mm. The outer diameter of the outer sheath 80 can be appropriately selected. For example, the outer diameter of the outer sheath 80 can be 1.3 mm to 2.0 mm. As an example, the outer diameter of the outer sheath 80 can be 2.0 mm.

The distal tube 75 is fixed to the distal side of the linear motion shaft 70. The distal tube 75 internally has a lumen 76, and the lumen 76 communicates with the lumen 72 of the linear motion shaft 70.

The distal tube 75 material is not particularly limited. However, for example, the distal tube 75 material is preferably a polyolefin such as polyethylene, polypropylene, ethylene-propylene copolymer, ethylene-vinyl acetate copolymer, polyvinyl chloride, polystyrene, polyamide, polyimide, or a combination of polyolefins.

As illustrated in FIGS. 1 and 2, the operation unit 90 includes the casing 91, a drive mechanism 93 which applies a rotational force to the drive shaft 60, and the movement mechanism 92 which moves the linear motion shaft 70 along the rotation axis X.

The drive mechanism 93 includes a driving gear 94 which meshes with the driven gear 61, a motor 96 serving as a driving source provided with a rotary shaft 95 to which the driving gear 94 is fixed, a battery 97 which supplies power to the motor 96, and a switch 98 which controls the motor 96 to be driven. The switch 98 is turned on to rotate the rotary shaft 95 of the motor 96. In this manner, the driven gear 61 meshing with the driving gear 94 is rotated, and the drive shaft 60 is rotated. If the drive shaft 60 is rotated, the rotary structure 40, the support portion 50, and the distal tube 75 which are fixed to the distal side of the drive shaft 60 are rotated.

The movement mechanism 92 includes a dial 100 which can be rotated by an operator with a finger, a rotatable feed screw 101 which coaxially interlocks with the dial 100, a linear slide 102 linearly movable by the feed screw 101, and a bearing portion 103 fixed to the linear slide 102 to rotatably hold the linear motion shaft 70.

The dial 100 is rotatably held inside the casing 91. The outer peripheral surface of the dial 100 is exposed from an opening portion 104 formed in the casing 91. The dial 100 can be rotated by operating the outer peripheral surface with the finger. The feed screw 101 is rotatably held inside the casing 91. The linear slide 102 has a female screw to which the feed screw 101 is screwed. The linear slide 102 is not rotatable relative to the casing 91, and is linearly movable along the rotation axis X. It is preferable that the bearing portion 103 fixed to the linear slide 102 is a thrust bearing capable of receiving a thrust force in order to apply a moving force to the linear motion shaft 70 in response to the movement of the linear slide 102.

Figure 7:
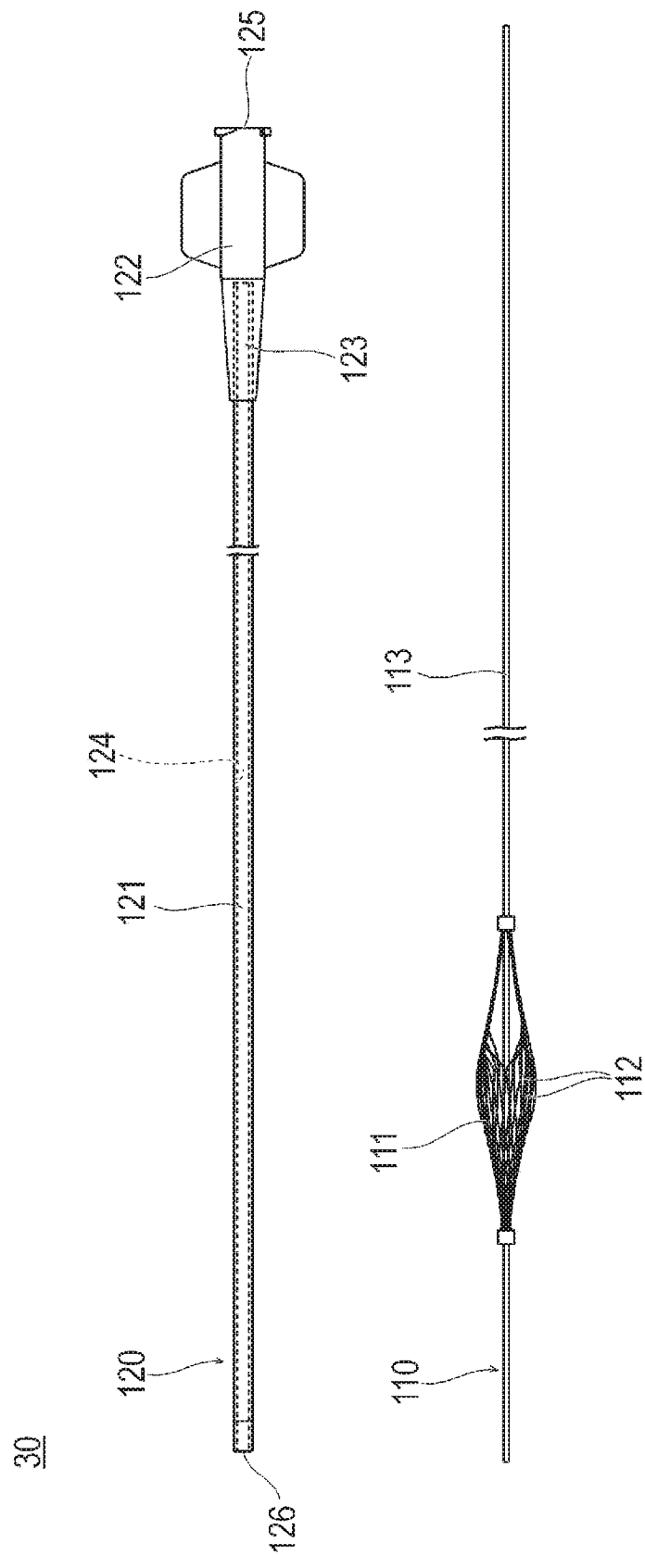
FIG. 7 is a plan view illustrating a collecting device.

As illustrated in FIGS. 1 and 7, the collecting device 30 includes a filter instrument 110 having a function as a filter, and a sheath 120 capable of accommodating the filter instrument 110.

The filter instrument 110 includes a filter portion 111 obtained by braiding a plurality of wires 112, and an elongated shaft portion 113 interlocking with the filter portion 111 after penetrating the filter portion 111.

The filter portion 111 is contracted by being accommodated inside the sheath 120, and can be expanded due to a self-expanding force by being released from the sheath 120. In the filter portion 111, the distal side having a closed basket shape interlocks with the shaft portion 113, and the proximal side interlocks with the shaft portion 113 after the plurality of wires 112 are twisted.

The outer diameter of the wire 112 can be appropriately selected depending on a material and applications of the wire 112. For example, the outer diameter of the wire 112 can be 20 µm to 100 µm. As an example, the outer diameter of the wire 112 can be 40 µm.

The wire 112 material is preferably a flexible material. For example, the wire 112 material is preferably a shape memory alloy for which a shape memory effect or super-elasticity, which is provided by means of heat treatment, stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide. For example, the shape memory alloy can be a Ni—Ti system, a Cu—Al—Ni system, and a Cu—Zn—Al system, or a combination of shape memory alloys. For example, a structure obtained by combining a plurality of materials to each other includes a structure obtained by coating the core wire made of Pt coated with a Ni—Ti alloy to provide a contrasting property, or a structure obtained by performing gold plating on the core wire made of the Ni—Ti alloy.

The shaft portion 113 material is not particularly limited. However, for example, the shaft portion 113 material can preferably be stainless steel or a shape memory alloy.

The sheath 120 includes a tubular body 121, a hub 122, and an anti-kink protector 123. The tubular body 121 includes a lumen 124 capable of accommodating the filter instrument 110, and is open in a tubular body opening portion 126 formed in the distal side portion. The hub 122 is fixed to the proximal side portion of the tubular body 121, and includes a hub opening portion 125 which communicates with the lumen 124. The anti-kink protector 123 is a flexible member for covering an interlock portion between the tubular body 121 and the hub 122, and suppresses kink of the tubular body 121.

The tubular body 121 material is not particularly limited. However, for example, the tubular body 121 material is preferably a polyolefin such as polyethylene, polypropylene, ethylene-propylene copolymer, ethylene-vinyl acetate copolymer, polyvinyl chloride, polystyrene, polyamide, polyimide, or a combination of polyolefins.

Next, a method of using the medical device 10 according to the present embodiment will be described by exemplifying a case of cutting a stenosed substance inside a blood vessel.

Figure 8A:
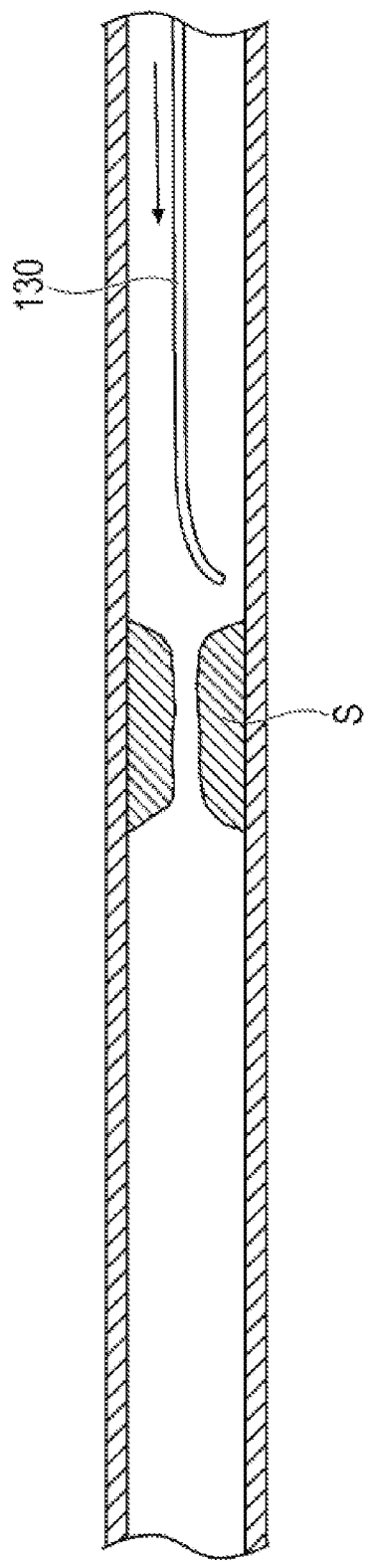
Figure 8B:
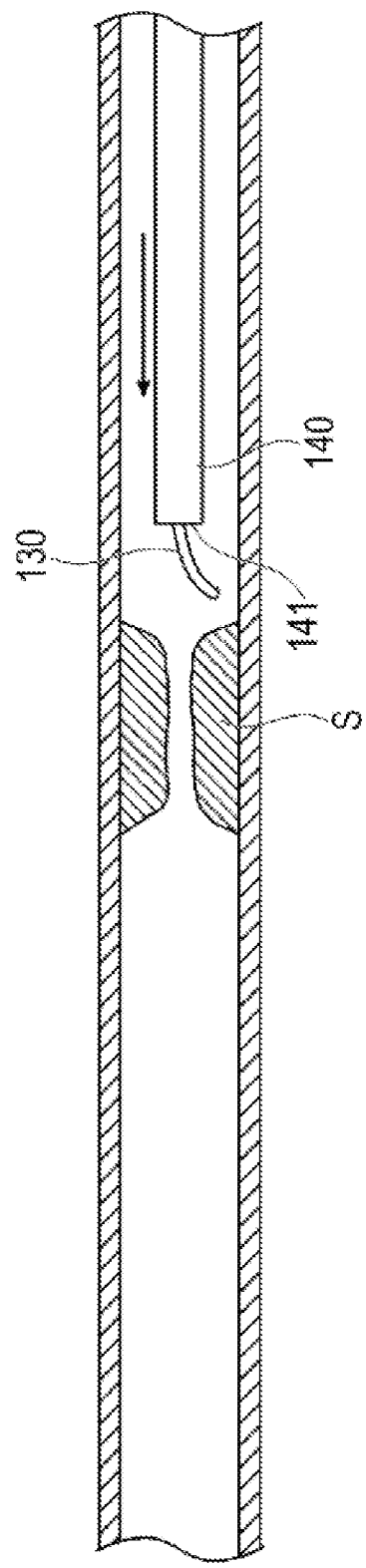

First, an introducer sheath (not illustrated) is percutaneously inserted into the blood vessel on an upstream side (proximal side) from a stenosed site S of the blood vessel, and a guide wire 130 is inserted into the blood vessel via the introducer sheath. Next, the guide wire 130 is pushed forward so as to reach the proximal side of the stenosed site S as illustrated in FIG. 8A. Thereafter, the proximal side portion of the guide wire 130 located outside the body is inserted into a catheter opening portion 141 on the distal side of a guiding catheter 140. As illustrated in FIG. 8B, the guiding catheter 140 is inserted into the blood vessel along the guide wire 130 so as to reach the proximal side of the stenosed site S.

Next, the proximal side portion of the guide wire 130 located outside the body is inserted into a catheter opening portion 151 on the distal side of a support catheter 150, and the support catheter 150 is pushed forward to the proximal side of the stenosed site S. Thereafter, as illustrated in FIG. 9A, the support catheter 150 and the guide wire 130 are caused to reach the distal side from the stenosed site S. Thereafter, in a state where the support catheter 150 is left behind inside the blood vessel, the guide wire 130 is removed.

Next, the collecting device 30 in which the filter instrument 110 is accommodated inside the sheath 120 is prepared. The filter portion 111 is located at a position close to the distal side portion of the tubular body 121 of the sheath 120, and a shape of the filter portion 111 is restrained in a contracted state. Next, as illustrated in FIG. 9B, the collecting device 30 is inserted into the blood vessel via the support catheter 150 so as to reach the distal side from the stenosed site S. Thereafter, the support catheter 150 is removed.

Next, the sheath 120 is moved to the proximal side relative to the filter instrument 110, and the filter portion 111 is caused to protrude to the distal side from the tubular body 121. In the manner, as illustrated in FIG. 10A, the filter portion 111 is brought into an expanded state due to a self-restoring force, and the outer peripheral portion of the filter portion 111 having a basket shape comes into contact with an inner wall surface of the blood vessel. In this case, the filter portion 111 is open toward the stenosed site S located on the upstream side (proximal side). Thereafter, the filter instrument 110 is left behind, and the sheath 120 is removed.

Next, the rotary structure 40 and the support portion 50 are contracted, and the treatment device 20 in a state of being accommodated inside the outer sheath 80 is prepared. The proximal side portion of the shaft portion 113 is inserted into the distal side opening portion of the distal tube 75. As illustrated in FIG. 10B, the proximal side portion of the shaft portion 113 is caused to reach the inside of the blood vessel via the guiding catheter 140. Next, as illustrated in FIG. 11A, the outer sheath 80 is moved to the proximal side, and the rotary structure 40 and the support portion 50 are exposed inside the blood vessel. In this state, the rotary structure 40 and the support portion 50 are in a contracted state. Thereafter, as illustrated in FIG. 2, if the dial 100 is rotated, the feed screw 101 is rotated so that the linear slide 102 moves to the proximal side. The linear motion shaft 70 interlocking (i.e., connecting) with the linear slide 102 moves to the proximal side. If the linear motion shaft 70 moves to the proximal side, the distal end portion 42 and the proximal end portion 43 of the rotary structure 40 move close to each other. As illustrated in FIG. 11B, the central portion of the support portion 50 is brought into an expanded state after being deformed so as to be bent outward in the radial direction. If the central portion of the support portion 50 is bent outward in the radial direction, the strut 41 located outside the support portion 50 is expanded after being pushed outward in the radial direction by the support portion 50. In this case, in at least an initial expanding stage, the distal end portion 42 of the cutting portion 47 is not fixed to the support portion 50 and the linear motion shaft 70. Accordingly, no force acts in the axial direction between the distal end portion 42 and the proximal end portion 43. The cutting portion 47 is expanded by a force acting outward in the radial direction which is received from the support portion 50. Therefore, a gap (or space) is less likely to be generated between the strut 41 and the wire rod 51. Then, each size of the rotary structure 40 and the support portion 50 can be optionally adjusted using the rotation amount of the dial 100. In this way, compared to a case of performing the cutting by using the rotary body having a polishing material adhering to an outer surface of a balloon whose inflated diameter can be regulated, the expanded size of the rotary structure 40 can be optionally adjusted to a desired size. Therefore, the cutting can be effectively performed. In a state where the rotary structure 40 and the support portion 50 are expanded, the cutting portion 47 is located inside the tangential line L between the first non-cutting portion 56 and the second non-cutting portion 48 in a cross section along the axial direction.

Next, if the switch 98 of the operation unit 90 is turned on, a driving force of the motor 96 is transmitted from the driving gear 94 to the driven gear 61, and the drive shaft 60 interlocking with the driven gear 61 is rotated. The rotary structure 40 and the support portion 50 which interlock with the drive shaft 60 are rotated. If the rotary structure 40 and the support portion 50 are rotated, the linear motion shaft 70 interlocking with both of these on the distal side is also rotated. The proximal portion of the linear motion shaft 70 is supported by the bearing portion 103. Accordingly, even if the proximal portion of the linear motion shaft 70 is rotated, it is possible to maintain an expanded state of the rotary structure 40 and the support portion 50.

Next, in a state where the rotary structure 40 and the support portion 50 are rotated, the treatment device 20 is pushed forward as illustrated in FIG. 12A. In this manner, the cutting edge 47 formed in the rotary structure 40 comes into contact with the stenosed site S, and the stenosed substance is cut into a debris D so as to flow to the distal side (downstream side). The debris D flowing to the distal side enters the inside of the filter portion 111 located on the distal side, and is collected and filtered by the filter portion 111. In this manner, the debris D can be prevented from flowing to a peripheral blood vessel, and a new stenosed site can be prevented from appearing in the peripheral blood vessel.

Then, when the stenosed site S is cut, the first non-cutting portion 56 of the support portion 50 protrudes outward in the radial direction between the struts 41. Accordingly, even if the first non-cutting portion 56 comes into contact with the biological tissue, the edge portion of the strut 41 does not come into contact with a normal biological tissue.

In addition, as illustrated in FIG. 12B, for example, in a case where the stenosed site S is unevenly formed or in a case where the blood vessel is curved, the rotary structure 40 is pushed forward. Consequently, the rotary structure 40 is inclined toward the blood vessel by receiving the force from the stenosed site S or the vascular wall, thereby causing a possibility that the cutting portion 47 may move close to the biological tissue. However, the cutting portion 47 is located inside the tangential line L between the first non-cutting portion 56 and the second non-cutting portion 48. Accordingly, before the cutting portion 47 comes into contact with the biological tissue, the first non-cutting portion 56 and the second non-cutting portion 48 come into contact with the biological tissue. Therefore, even if the rotary structure 40 is inclined, the cutting portion 47 is less likely to come into contact with the biological tissue. Therefore, damage to the normal biological tissue can be prevented, and relative safety can be improved. In addition, even if the rotary structure 40 is inclined, the cutting portion 47 is less likely to come into contact with the biological tissue. Accordingly, the drive shaft 60 is curved by pushing the rotary structure 40 forward so that the rotary structure 40 is intentionally inclined relative to the blood vessel. In this manner, the stenosed site S can also be cut.

In addition, the strut 41 is deformed so that the outer peripheral surface of the portion having the cutting portion 47 is inclined inward in the radial direction on the side in the rotation direction Y (refer to FIG. 6B), the side inclined inward in the radial direction of the strut 41 first comes into smooth contact with the contact target such as the stenosed site S and the biological tissue. Accordingly, it is possible to reduce excessive damage to the biological tissue. In addition, the strut 41 is cut out from the tubular body having the diameter smaller than the diameter in an expanded state. Accordingly, the radius of curvature of the outer peripheral surface of the strut 41 is smaller than the distance from the rotation axis X to the outer peripheral surface of the strut 41 in the expanded state. Therefore, the edge portion of the strut 41 is less likely to come into contact with the object. Therefore, it is possible to reduce the excessive damage to the biological tissue.

In addition, the support portion 50 is disposed inside the strut 41. Accordingly, the fallen hard debris D is less likely to be interposed between the struts 41. The strut 41 is not rolled up outward, and thus, the strut 41 can be prevented from being damaged or broken.

In addition, the strut 41 having the cutting portion 47 is supported by the support portion 50 so as to increase a radial force (force acting in the radial direction). Accordingly, regardless of the expandable and contractible structure, relatively high cutting performance can be achieved. In addition, the gap (or space) between the struts 41 is supplemented by the support portion 50. Accordingly, the cross section as a whole is allowed to have substantially circular shape by the strut 41 and the support portion 50. Therefore, the rotary structure 40 is centrally located at a proper position. In addition, a portion of the debris D cut by the cutting edge 47 of the strut 41 can be collected into the support portion 50.

After the stenosed substance is completely cut, the switch 98 is turned off so as to stop the rotation of the drive shaft 60. Next, if the dial 100 is rotated in a direction opposite to a direction when the rotary structure 40 and the support portion 50 are expanded, as illustrated in FIG. 1, the feed screw 101 is rotated, and the linear slide 102 moves to the distal side. The linear motion shaft 70 interlocking with the linear slide 102 moves to the distal side. If the linear motion shaft 70 moves to the distal side, the distal end portion 42 of the rotary structure 40 moves so as to be separated from the proximal end portion 43, and the rotary structure 40 and the support portion 50 are brought into a state of being contracted inward in the radial direction. Thereafter, the outer sheath 80 is moved to the distal side. As illustrated in FIG. 13A, and the rotary structure 40 and the support portion 50 are accommodated inside the outer sheath 80, and the treatment device 20 is removed via the guiding catheter 140.

Next, the proximal side portion of the shaft portion 113 is inserted into the tubular body opening portion 126 of the sheath 120 (aspirating catheter). As illustrated in FIG. 13B, the sheath 120 is inserted into the blood vessel via the guiding catheter 140. In this state, a Y-connector (not illustrated) is connected so as to communicate with the hub opening portion 125 of the sheath 120, and a syringe is connected to an opening portion into which the shaft portion 113 of the Y-connector is not inserted. Thereafter, if an aspirating force is applied by pulling a plunger of the syringe, negative pressure is generated inside the lumen 124 extending from the distal side to the proximal side. The debris D inside the filter portion 111 is fetched into the lumen 124 from the tubular body opening portion 126. When the debris D is aspirated by the syringe, the debris D can be effectively aspirated by moving the tubular body 121 forward and rearward, if necessary. In this way, the debris D inside the filter portion 111 is partially or entirely aspirated and fetched into the lumen 124, thereby bringing the filter portion 111 into a state where the filter portion 111 is likely to be contracted. An instrument (aspirating catheter) for aspirating the debris D may be a catheter different from the sheath 120. In addition, the instrument for applying the aspirating force is not limited to the syringe. For example, the instrument may be a pump.

Next, if the sheath 120 is moved relative to the distal side of the shaft portion 113, the filter portion 111 is pulled by the shaft portion 113 so as to move into the lumen 124 of the tubular body 121. Thereafter, the filter instrument 110 is removed together with the sheath 120, the guiding catheter 140 and the introducer sheath are removed, and the medical procedure is completed. The filter instrument 110 may not be accommodated in the sheath 120, and may be directly accommodated inside the guiding catheter 140 without using the sheath 120. In this case, the debris D may not be aspirated and removed.

As described above, the medical device 10 according to the first embodiment is a device for cutting the object inside the biological lumen, and includes the rotatable drive shaft 60, the rotatable cutting portion 47 interlocking with the distal side of the drive shaft 60, the first non-cutting portion 56 that is larger than the cutting portion 47 in the radial direction, and that can come into smooth contact with the biological tissue, and the second non-cutting portion 48 that is located so as to interpose the cutting portion 47 between the first non-cutting portion 56 and the second non-cutting portion 48 along the axial direction, and that can come into smooth contact with the biological tissue. The cutting portion 47 is located inside the tangential line L between the first non-cutting portion 56 and the second non-cutting portion 48 in the cross section along the axial direction. According to the medical device 10 configured as described above, the cutting portion 47 is located inside the tangential line L between the first non-cutting portion 56 and the second non-cutting portion 48 in the cross-section along the axial direction. Accordingly, while the rotating cutting portion 47 properly cuts the object inside the biological lumen, the first non-cutting portion 56 and the second non-cutting portion 48 help prevent the cutting portion 47 from coming into contact with the biological tissue. Therefore, relative safety can be improved by reducing damage to the biological tissue.

In addition, the first non-cutting portion 56 is expandable outward in the radial direction. Accordingly, in a state where the first non-cutting portion 56 protruding in the radial direction is contracted, the first non-cutting portion 56 can be transported into the biological lumen. In this manner, the influence on the living body can be reduced, and the medical device 10 can be inserted into the biological lumen having a smaller diameter. Therefore, the medical device 10 is more widely applicable.

In addition, according to the present disclosure, there is also provided the treatment method for cutting the object inside the biological lumen. The treatment method for cutting the object inside the biological lumen by using the above-described medical device 10 includes a step of inserting the cutting portion 47, the first non-cutting portion 56, and the second non-cutting portion 48 into the biological lumen, a step of cutting the object inside the biological lumen by causing the drive shaft 60 to rotate the cutting portion 47 while maintaining a state where the cutting portion 47 is located inside the tangential line L between the first non-cutting portion 56 and the second non-cutting portion 48 in the cross section along the axial direction, and a step of removing the cutting portion 47, the first non-cutting portion 56, and the second non-cutting portion 48 from the inside of the biological lumen. According to the treatment method, in the cutting step, the cutting portion 47 is located inside the tangential line L between the first non-cutting portion 56 and the second non-cutting portion 48 in the cross section along the axial direction. Accordingly, while the rotating cutting portion 47 cuts the object inside the biological lumen, the first non-cutting portion 56 and the second non-cutting portion 48 prevent the cutting portion 47 from coming into contact with the biological tissue. Therefore, the safety can be improved by reducing the damage to the biological tissue.

In addition, in the cutting step, the object can be cut while the rotary structure 40 having the cutting portion 47 is inclined inside the biological lumen. In this manner, the object inside the biological lumen can be cut in a wide range. Even if the rotary structure 40 is inclined, the first non-cutting portion 56 and the second non-cutting portion 48 can prevent the cutting portion 47 from coming into contact with the biological tissue. Therefore, the relative safety of the medical device 10 and treatment method can be improved.

Second Embodiment

A medical device 160 according to a second embodiment of the present disclosure is different from that according to the first embodiment only in that the first non-cutting portion is provided outside the rotary structure 40. The same reference numerals will be given to elements having functions which are the same as those according to the first embodiment, and description of the reference number, elements, and functions will be omitted.

Figure 14A:
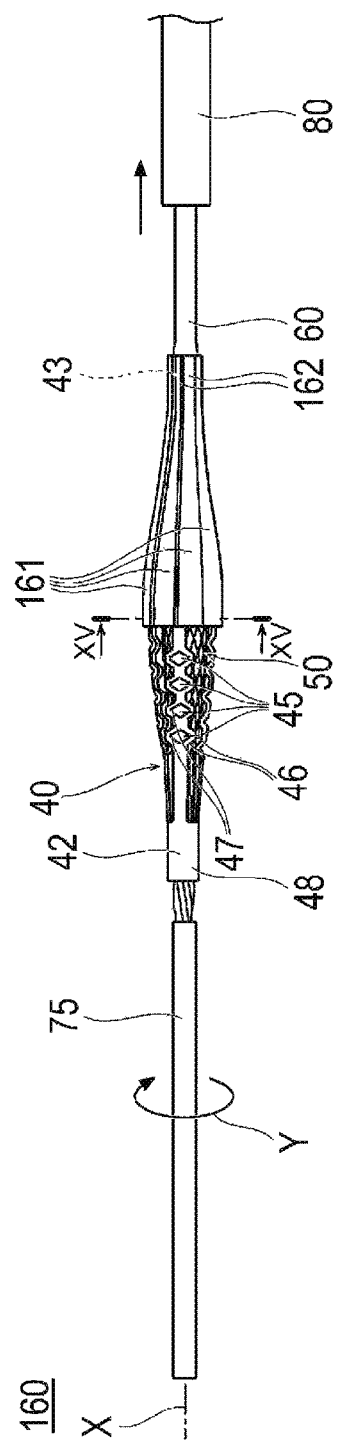
Figure 14B:
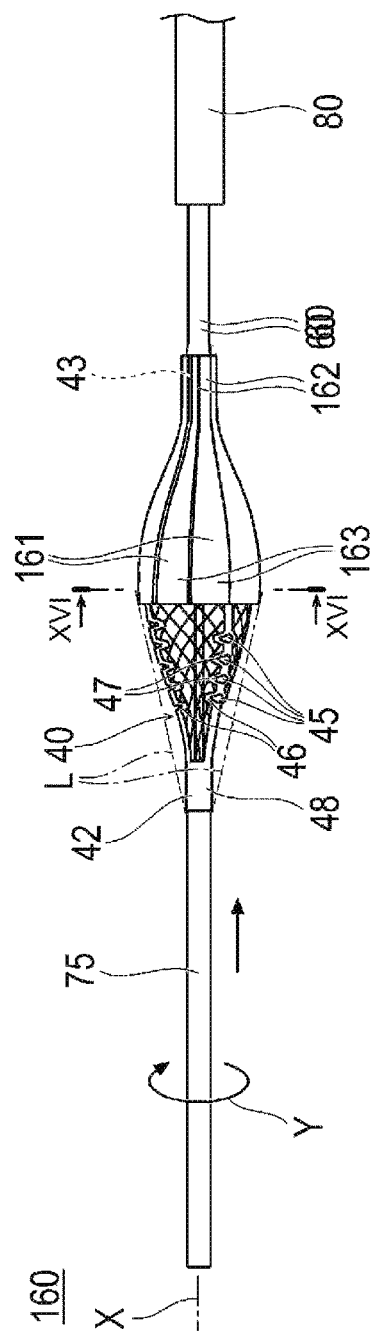
Figure 15:
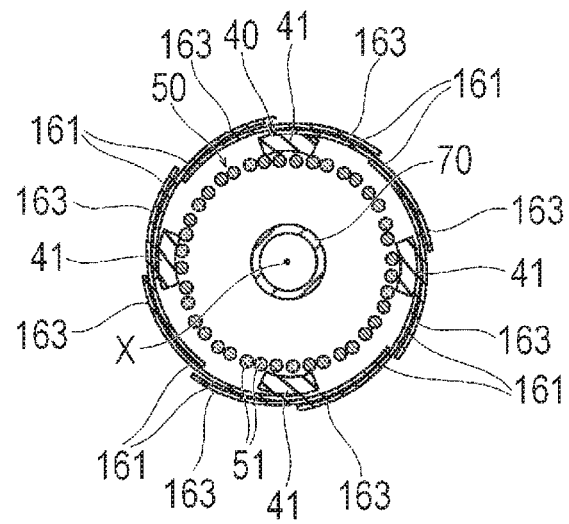
FIG. 15 is a cross-sectional view taken along line XV-XV in FIG. 14A.
Figure 16:
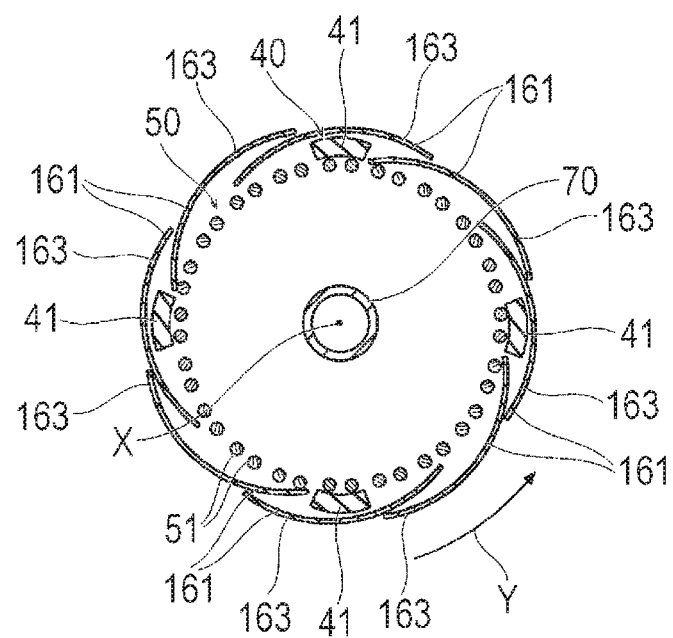
FIG. 16 is a cross-sectional view taken along line XVI-XVI in FIG. 14B.

As illustrated in FIG. 14A, in the medical device 160 according to the second embodiment, a plurality of plates 161 are arrayed parallel to each other outside the rotary structure 40 in the circumferential direction. Each of the plates 161 is fixedly attached to the outer peripheral surface of the proximal end portion 43 of the rotary structure 40. In an axially orthogonal axial cross section, the plurality of plates 161 is formed in an arc shape as illustrated in FIG. 15, and the plurality of plates is arrayed parallel to each other in the circumferential direction, while some plates 161 overlap each other. Each of the plates 161 is fixed only in a plate proximal portion 162 in contact with the proximal end portion 43. A portion on the distal side can be bent outward in the radial direction by using the plate proximal portion 162 as a fixed end. Since the portion on the distal side is bent, each of the plates 161 is slidable so that an area of the overlapping portion is changed. Accordingly, if the rotary structure 40 and the support portion 50 are expanded, as illustrated in FIGS. 14B and 16, while the overlapping area between the plates 161 decreases, the tubular body configured to include the plurality of plates 161 is expanded in a funnel shape. In addition, if the rotary structure 40 and the support portion 50 are contracted, as illustrated in FIGS. 14A and 15, while the overlapping area between the plates 161 increases, the tubular body configured to include the plurality of plates 161 is contracted. In each of the plates 161, the distal portion surrounds the largest outer diameter portion of the rotary structure 40, and a first non-cutting portion 163 is formed on the outer surface of the distal portion. An orientation in which the plates 161 overlap each other is set to an orientation in which a stepped portion of the plates 161 comes into smooth contact with the biological tissue so as not to cut the biological tissue, when cutting portion 47 cuts the object by rotating the drive shaft 60. Furthermore, the radius of curvature of the arc of the plate 161 is smaller than the radius of the expanded rotary structure 40. Accordingly, the stepped portion of the plates 161 does not come into contact with the biological tissue.

A material of the plate 161 is preferably a flexible material. For example, the material of the plate 161 is preferably a shape memory alloy for which a shape memory effect or super-elasticity, which is provided by means of heat treatment, stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide.

When the object inside the biological lumen is cut using the medical device 160 according to the second embodiment, the cutting portion is located inside the tangential line L between the first non-cutting portion 163 and the second non-cutting portion 48 in the cross section along the axial direction. Accordingly, while the rotating cutting portion 47 properly cuts the object inside the biological lumen, the first non-cutting portion 163 and the second non-cutting portion 48 prevent the cutting portion 47 from coming into contact with the biological tissue. Therefore, the relative safety of the medical device and treatment method can be improved by reducing the damage to the biological tissue.

Third Embodiment

A medical device 170 according to a third embodiment of the present disclosure is different from that according to the first embodiment only in that an expandable portion is formed in a distal portion of an outer sheath capable of accommodating the rotary structure 40. The same reference numerals will be given to elements having functions which are the same as those according to the first embodiment, and description of the reference number, elements, and functions will be omitted.

Figure 17A:
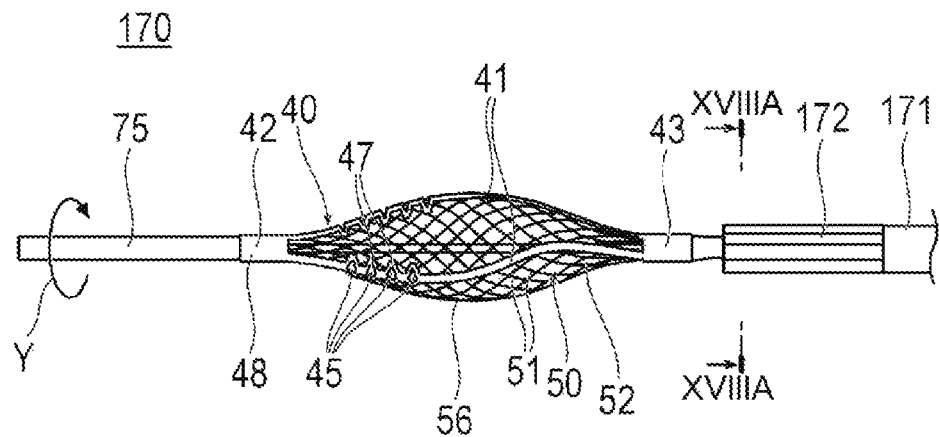
Figure 17B:
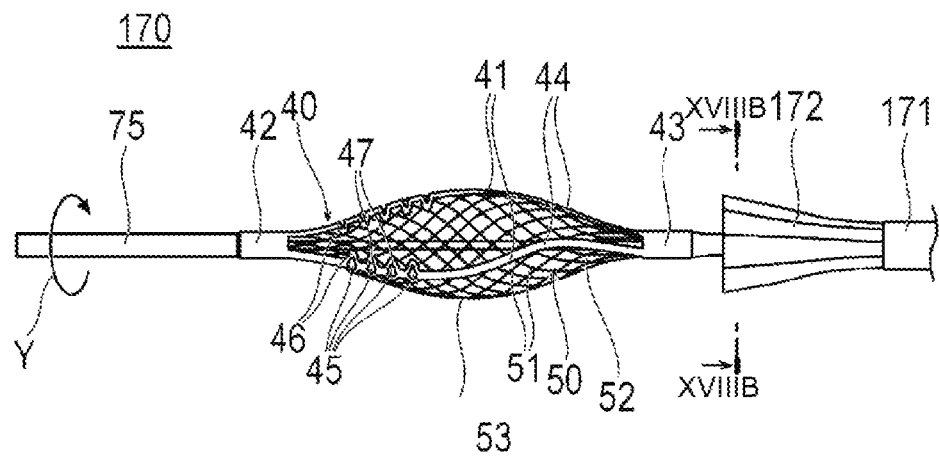
Figure 18A:
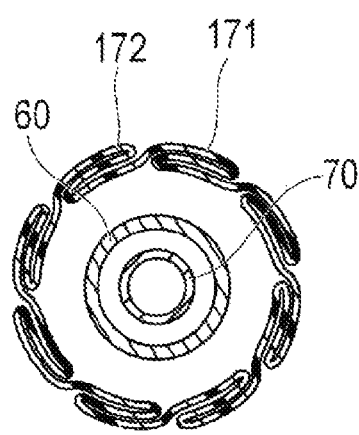
Figure 18B:
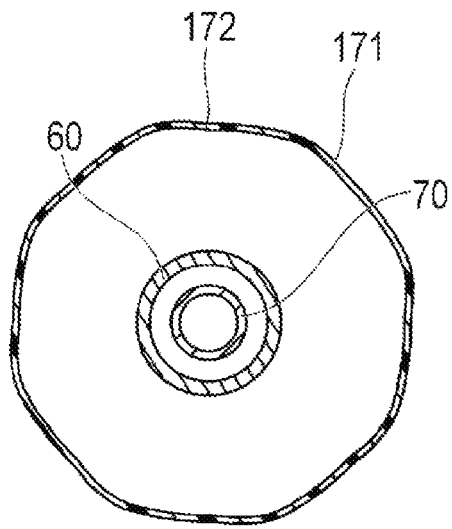

As illustrated in FIGS. 17A, 17B, 18A, and 18B, in the medical device 170 according to the third embodiment, a distal portion of an outer sheath 171 has an expandable portion 172 which is formed to be expandable in a flared shape while being folded back in the circumferential direction. As illustrated in FIGS. 17A and 18A, the expandable portion 172 is folded and contracted in a state where no external force is applied. As illustrated in FIGS. 17B and 18B, when a force is received from the inside in the radial direction, the folded portion spreads, and the expandable portion 172 is expandable so as to increase the inner diameter.

The expandable portion 172 material is not particularly limited. However, for example, the expandable portion 172 material can be preferably be a polyolefin such as polyethylene, polypropylene, ethylene-propylene copolymer, ethylene-vinyl acetate copolymer, polyvinyl chloride, polystyrene, polyamide, polyimide, or a combination of polyolefins.

Figures 19A, 19B:
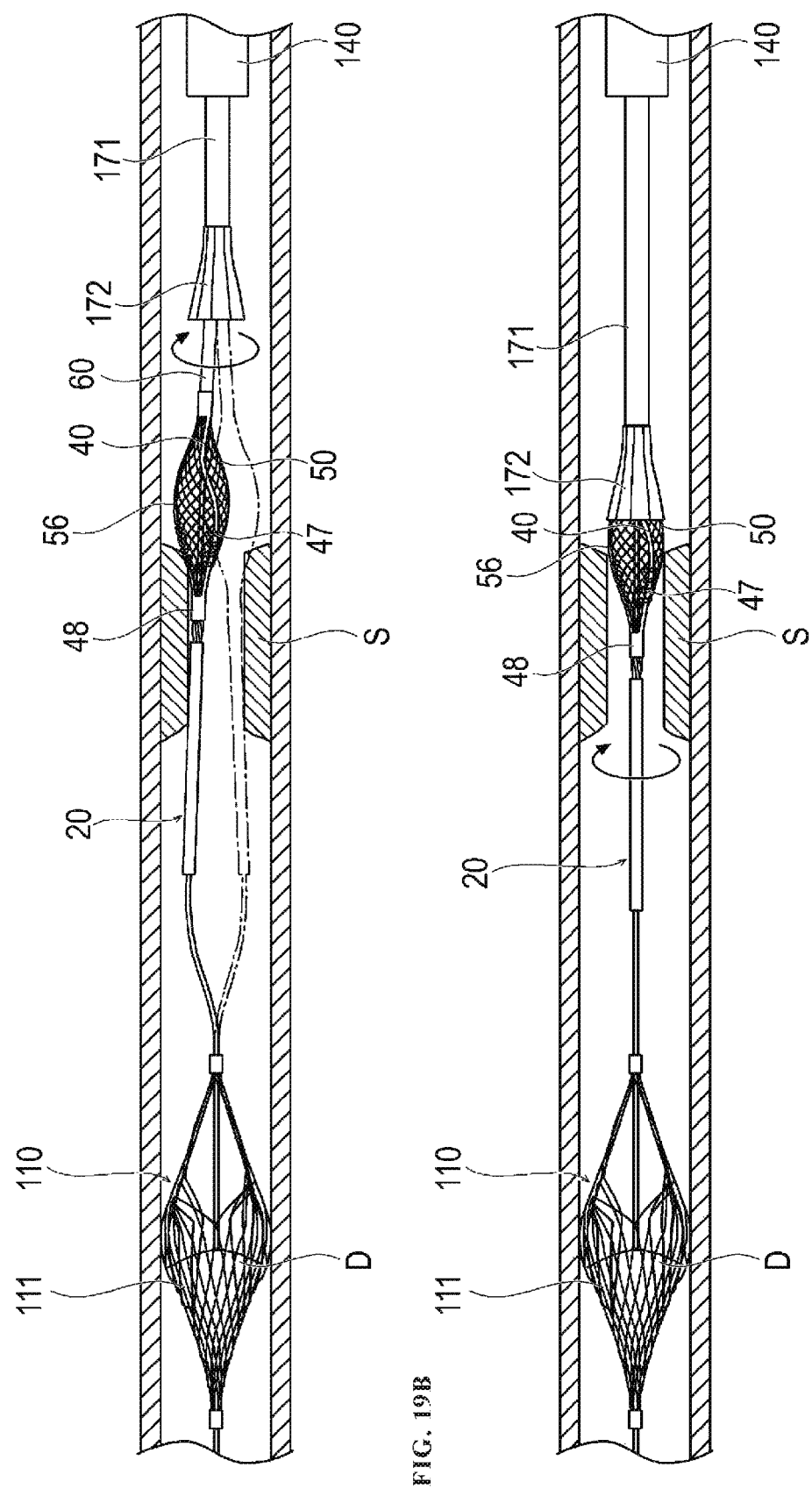

When the stenosed site S inside the biological lumen is cut using the medical device 170 according to the third embodiment, the rotary structure 40 and the support portion 50 can be expanded by being protruded to the distal side of the outer sheath 171. If the drive shaft 60 is rotated in this state, the expandable portion 172 of the outer sheath 171 can be rather easily expanded as illustrated in FIG. 19A. Accordingly, the drive shaft 60 which can be flexibly bent can be rather easily bent, thereby allowing the rotary structure 40 and the support portion 50 to be rotated so as to swing. Therefore, while a wide cutting range is secured by the swinging of the rotary structure 40, the first non-cutting portion 56 and the second non-cutting portion 48 help prevent the cutting portion 47 from coming into contact with the biological tissue. Therefore, the relative safety of the medical device and treatment method can be improved by reducing the damage to the biological tissue.

In addition, as illustrated in FIG. 19B, the proximal portion of the rotary structure 40 and the support portion 50 in an expanded state can be covered with the expandable portion 172 which is expanded. If the drive shaft 60 is rotated in this state, the outer sheath 171 can easily adjust the rotation of the rotary structure 40 and the support portion 50 so as not to swing. Accordingly, a state suitable for the cutting can be achieved in accordance with a situation of the object inside the biological lumen that is being cut. Furthermore, the first non-cutting portion 56 is covered with the expandable portion 172 which is expanded. Accordingly, the expandable portion 172 can also function as the first non-cutting portion. In this case, the expandable portion 172 is not rotationally driven by the drive shaft 60. Accordingly, the damage to the biological tissue can be reduced.

Figure 20:
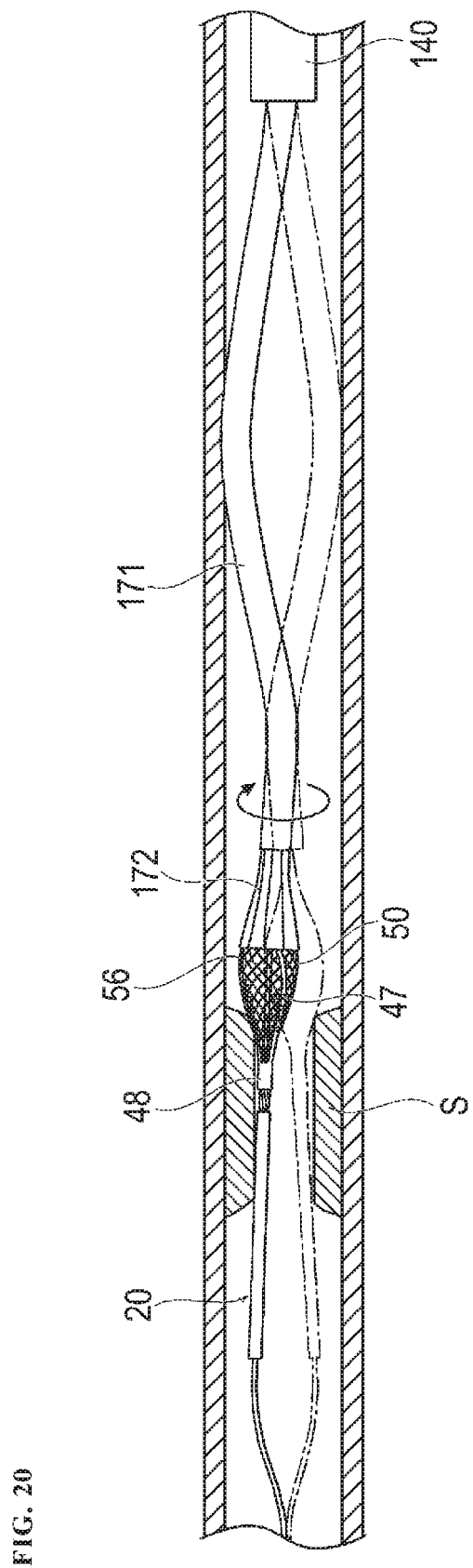
FIG. 20 is a schematic cross-sectional view illustrating a state when the stenosed substance is cut while a direction of the rotary structure is adjusted using the medical device according to the third embodiment.

In addition, as illustrated in FIG. 20, if a curved portion is formed in the distal portion of the outer sheath 171, the proximal portion of the outer sheath 171 is operated and rotated outside the body. In this manner, a position and an angle of the rotary structure 40 having the cutting portion 47 can be adjusted. Accordingly, a state suitable for the cutting can be achieved in accordance with the situation of the object inside the biological lumen that is being cut.

As described above, the medical device 170 according to the third embodiment can change the rotary structure 40 having the cutting portion 47 and rotated by the drive shaft 60 into a swingable state and a state of preventing the swing. In this manner, the medical device 170 can change the state of the rotary structure 40 in accordance with a situation of the object inside the biological lumen that is being cut, and a state suitable for the cutting can be achieved in accordance with the situation of the object inside the biological lumen that is being cut.

In addition, the medical device 170 has the outer sheath 171 which can accommodate the drive shaft 60 so as to be relatively rotatable and whose inner diameter of the distal portion is expandable. Therefore, the medical device 170 expands the distal portion of the outer sheath 171, thereby enabling the drive shaft 60 to swing. In addition, the medical device 170 causes the distal portion of the outer sheath 171 to accommodate at least a portion of the rotary structure 40 having the cutting portion 47, and adjusts the swinging of the rotary structure 40. Accordingly, a state suitable for the cutting can be achieved in accordance with the situation of the object inside the biological lumen that is being cut.

In addition, according to the treatment method for cutting the object inside the biological lumen by using the medical device 170 according to the third embodiment, in the cutting step, the proximal portion of the outer sheath 171 which can accommodate the drive shaft 60 and whose distal portion is curved is rotated on the operating hand side. In this manner, it is possible to adjust a position and inclination of the rotary structure 40 inside the biological lumen. In this manner, the proximal portion of the outer sheath 171 is operated. Accordingly, the position and the inclination of the rotary structure 40 inside the biological lumen can be rather easily adjusted. Therefore, a state suitable for the cutting can be achieved in accordance with the situation of the object inside the biological lumen that is being cut, and operability of the medical device can be improved.

In addition, in the cutting step, the outer sheath 171 which can accommodate the drive shaft 60 is moved relative to the rotary structure 40 in the axial direction. In this manner, it is possible to adjust the position and the inclination of the rotary structure 40 inside the biological lumen. In this manner, the proximal portion of the outer sheath 171 is operated. Accordingly, the position and the inclination of the rotary structure 40 inside the biological lumen can be easily adjusted. Therefore, a state suitable for the cutting can be achieved in accordance with the situation of the object inside the biological lumen that is being cut, and operability of the medical device can be improved.

Fourth Embodiment

A medical device 180 according to a fourth embodiment of the present disclosure is different from that according to the third embodiment only in that a weight is attached to the rotary structure 40. The same reference numerals will be given to elements having functions which are the same as those according to the first and third embodiments, and description of the reference number, elements, and functions will be omitted.

Figure 21:
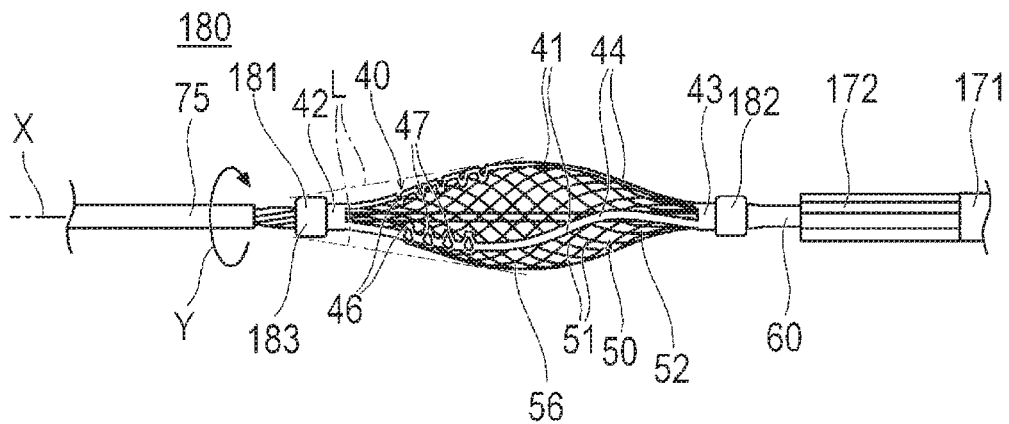
FIG. 21 is a plan view illustrating a treatment device of a medical device according to a fourth embodiment.

In the medical device according to the fourth embodiment, as illustrated in FIG. 21, a distal side weight 181 is attached to the distal end portion 42 of the rotary structure 40, and a proximal side weight 182 is attached to the proximal end portion 43. A second non-cutting portion 183 is formed on the outer peripheral surface of the distal side weight 181. The cutting portion 47 is located inside the tangential line L between the first non-cutting portion 56 and the second non-cutting portion 183 in the cross section along an axial direction X. The weight balance of the distal side weight 181 and the proximal side weight 182 is not biased in the circumferential direction, but may be biased. In a case where the weight balance of the distal side weight 181 and the proximal side weight 182 is biased in the circumferential direction, the center of gravity is eccentric from the central axis. The distal side weight 181 and the proximal side weight 182 are fixed so as not to be rotatable relative to the rotary structure 40, but may be fixed so as to be rotatable by using a bearing.

Figure 22A:
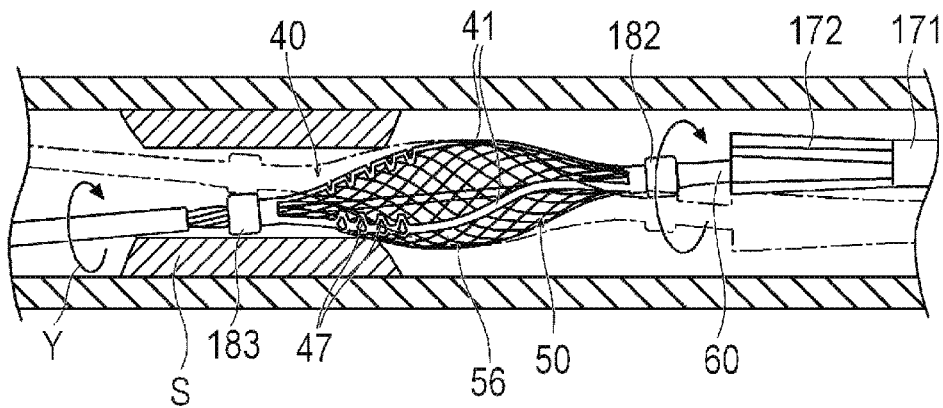

When the object inside the biological lumen is cut using the medical device 180 according to the fourth embodiment, the distal side weight 181 and the proximal side weight 182 are disposed in the rotary structure 40. Accordingly, in a state where the rotary structure 40 protrudes from the outer sheath 171, as illustrated in FIG. 22A, the rotary structure 40 is likely to be vibrated so as to swing (i.e., move from side to side). Therefore, while a wide cutting range is secured by the swinging (i.e., moving from side to side) of the rotary structure 40, the first non-cutting portion 56 and the second non-cutting portion 183 prevent the cutting portion 47 from coming into contact with the biological tissue. Therefore, the relative safety of the medical device and treatment method can be improved by reducing the damage to the biological tissue.

Figure 22B:
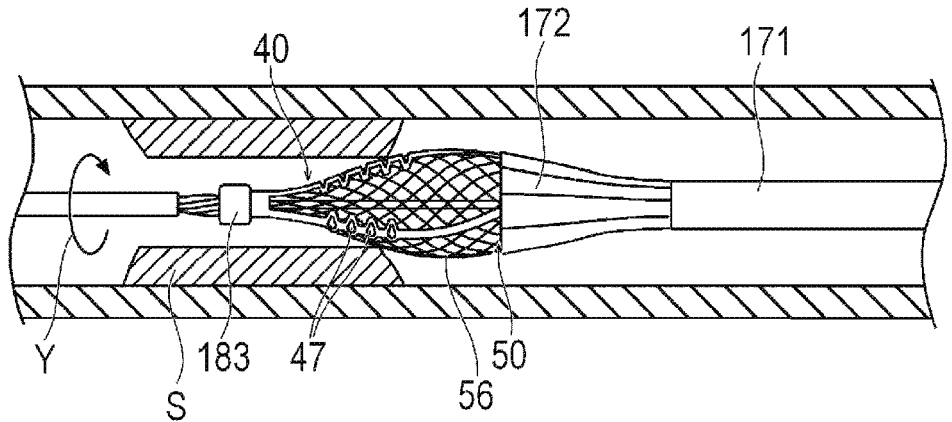

In addition, as illustrated in FIG. 22B, an expandable portion 172 of the outer sheath 171 is expanded, and the proximal portion of the rotary structure 40 and the support portion 50 in an expanded state is covered with the expandable portion 172. In this manner, a state where the swinging is likely to be performed by providing the distal side weight 181 and the proximal side weight 182 can be switched to a state where the swinging is less likely to be performed.

In addition, depending on the rotation speed of the drive shaft 60, the vibration of the rotary structure 40 can be adjusted so as to adjust a degree of the cutting performed by the cutting portion 47. For example, in a case where mass of a portion including the rotary structure 40 supported by the drive shaft 60 is set to m (kg) and a spring constant of the drive shaft 60 is set to k (N/m), critical speed (natural frequency) fc (Hz) of the portion including the rotary structure 40 supported by the drive shaft 60 is calculated as an approximate value by the following equation (i.e., Equation 1). A gyro effect acting on the rotary structure 40 or the influence of blood will be omitted.

Equation 1

$$f_c = 1/(2\pi) \cdot \sqrt{k/m}$$ Equation (1)

A rotating structure is rotated around the central axis of the structure at low rotation speed lower than the critical speed. Accordingly, the center of gravity turns outward in the rotation axis X. If the rotation speed approaches the critical speed, the vibration increases. If the rotation speed exceeds the critical speed, the center of gravity is located inside the central axis, and the center of gravity approaches the rotation center. Therefore, the structure approaches a state where the structure is rotated around the center of gravity. Therefore, the position of the center of gravity which can be set in advance and the rotation speed of the drive shaft 60 are utilized. In this manner, a cutting state is adjusted by using a change in the vibration of the rotary structure 40 including the cutting portion 47. Accordingly, a state suitable for the cutting can be achieved in accordance with a situation of the object inside the biological lumen that is being cut. In order to minimize the vibration as much as possible in this way, it is preferable to rotate the rotary structure 40 within a range not exceeding the critical speed. However, in order to facilitate the cutting performed by the cutting portion 47, it is also possible to rotate the rotary structure 40 at speed equal to or higher than the critical speed.

As described above, in the medical device 180 according to the fourth embodiment, the weight balance of the rotary structure 40 having the cutting portion 47 and rotated by the drive shaft 60 can be biased in the circumferential direction. In this manner, the rotary structure 40 can be vibrated so as to swing, and the cutting can be performed in a wide range.

In addition, the second non-cutting portion 183 can be rotated relative to the drive shaft 60. In this manner, friction can be reduced between the second non-cutting portion 183 and the wall of the biological lumen, and the safety can be improved by reducing the damage to the biological tissue.

In addition, according to the treatment method for cutting the object inside the biological lumen by using the medical device 180 according to the fourth embodiment, in the cutting step, the rotary structure 40 whose weight balance is biased in the circumferential direction is rotated. In this manner, the vibration of the rotary structure 40 can be induced. In this manner, the cutting portion 47 can cut the object in a wide range inside the biological lumen. Even if the rotary structure 40 is vibrated, the first non-cutting portion 56 and the second non-cutting portion 183 can prevent the cutting portion 47 from coming into contact with the biological tissue. Therefore, the relative safety of the medical device and treatment method can be improved.

In addition, in the cutting step, the position and the inclination of the rotary structure 40 inside the biological lumen can be adjusted by changing the rotation speed of the rotary structure 40 having the cutting portion 47. In this manner, the position and the inclination of the rotary structure 40 inside the biological lumen can be easily adjusted by changing the rotation speed. Therefore, a state suitable for the cutting can be achieved in accordance with a situation of the object inside the biological lumen that is being cut, and operability of the medical device can be improved.

Fifth Embodiment

Figure 23:
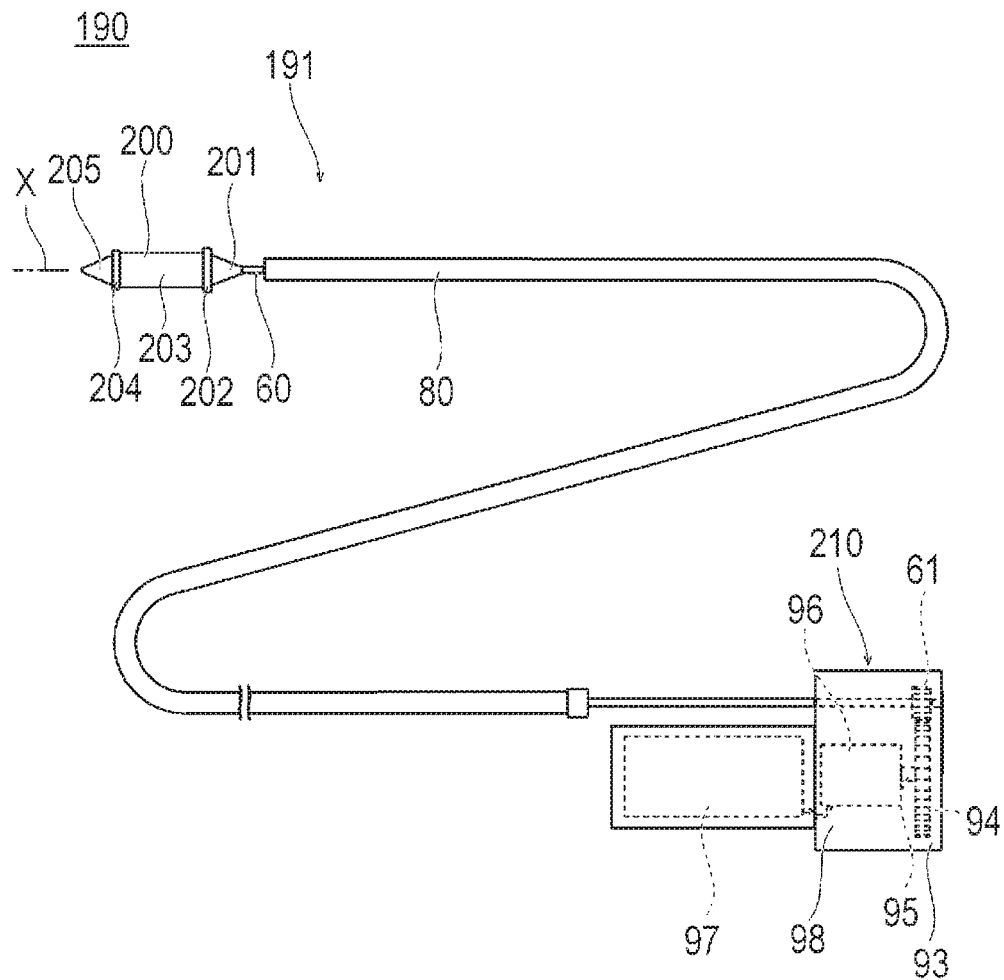
FIG. 23 is a plan view illustrating a treatment device of a medical device according to a fifth embodiment.

A medical device 190 according to a fifth embodiment of the present disclosure is different from that according to the first embodiment in the following points. As illustrated in FIG. 23, a structure of the rotary structure disposed in the treatment device is different. In the structure, the rotary structure is not expanded or contracted. Therefore, there is no linear motion shaft, and the movement mechanism for operating the linear motion shaft is not disposed in the operation unit. The same reference numerals will be given to elements having functions which are the same as those according to the first embodiment, and description of the reference number, elements, and functions will be omitted.

Figure 24:
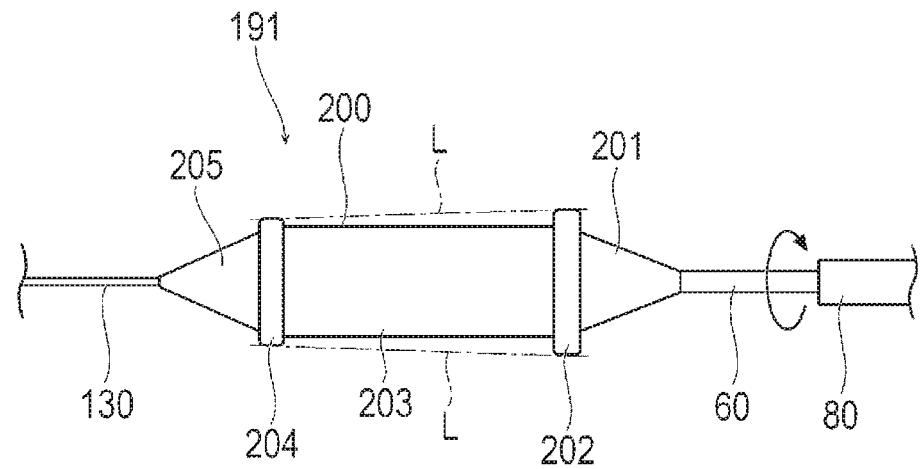
FIG. 24 is a plan view illustrating a distal portion of the treatment device according to a fifth embodiment.

As illustrated in FIGS. 23 and 24, a treatment device 191 includes a rotatable rotary structure 200, the drive shaft 60 for rotating the rotary structure 200, the outer sheath 80 capable of accommodating the rotary structure 200, and an operation unit 210 disposed on the hand side for operation.

The rotary structure 200 includes a proximal tapered portion 201 interlocking with the drive shaft 60, a first non-cutting portion 202 disposed on the distal side of the proximal tapered portion 201, a cutting portion 203 disposed on the distal side of the first non-cutting portion 202, a second non-cutting portion 204 disposed on the distal side of the cutting portion 203, and a distal tapered portion 205 disposed on the distal side of the second non-cutting portion 204. The rotary structure 200 internally has a guide wire lumen with which the lumen of the drive shaft 60 communicates and into which the guide wire can be inserted.

The first non-cutting portion 202 has the largest outer diameter in the rotary structure 200, and the outer peripheral surface is formed in a relatively smooth and annular shape. Subsequent to the first non-cutting portion 202, the second non-cutting portion 204 has the second largest outer diameter in the rotary structure 200, and the outer peripheral surface is formed in a relatively smooth and annular shape. The cutting portion 203 is formed in a cylindrical shape between the first non-cutting portion 202 and the second non-cutting portion 204, and the outer diameter is constant in the axial direction.

Figure 25A:
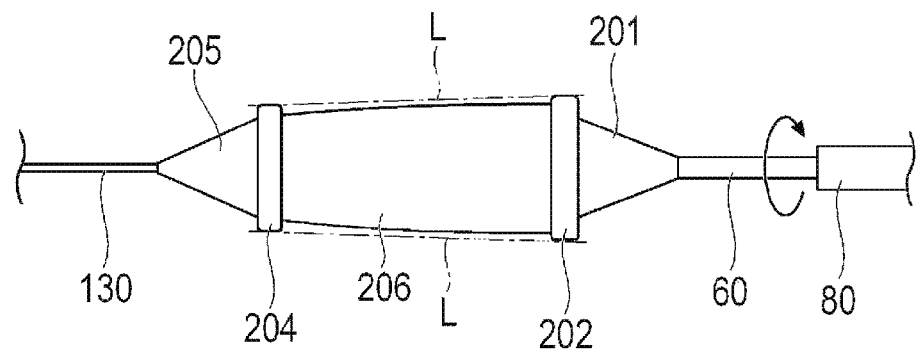
Figure 25B:
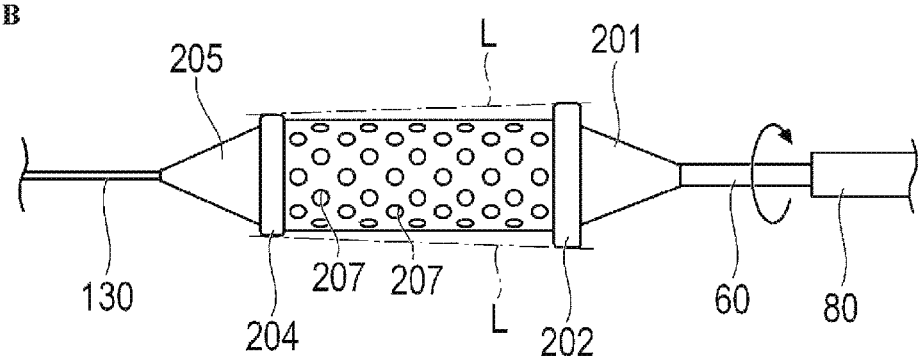
Figure 25C:
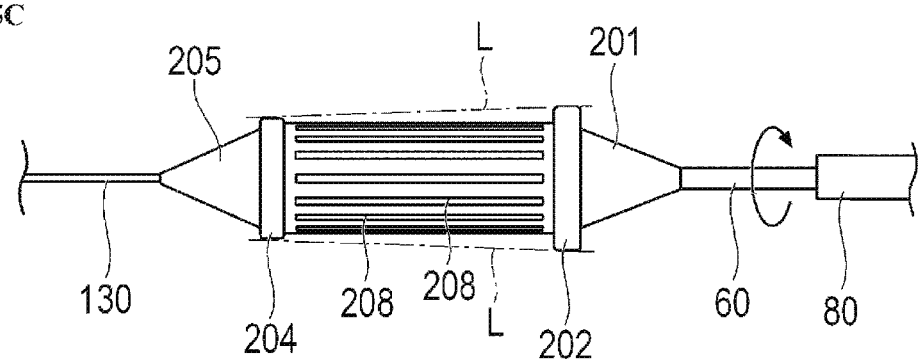

The respective outer diameters of the first non-cutting portion 202 and the second non-cutting portion 204 may be the same as each other, or the outer diameter of the second non-cutting portion 204 may be larger than the outer diameter of the first non-cutting portion 202. In addition, if the cutting portion 203 is located inside the tangential line L between the first non-cutting portion 202 and the second non-cutting portion 204, the outer diameter may not be constant in the axial direction. Therefore, for example, as in a first modification example illustrated in FIG. 25A, a cutting portion 206 may be formed in a tapered shape whose outer diameter increases toward the proximal side, or the cutting portion 206 may protrude so that the central portion bulges in a cross section along the axial direction. The cutting portion 206 is located inside the tangential line L between the first non-cutting portion 202 and the second non-cutting portion 204 in the cross section along the axial direction of the rotary structure 200. A polishing material, for example, a diamond particle adheres to the outer surface of the cutting portion 206. Alternatively, as in a second modification example illustrated in FIG. 25B, a cutting portion 207 may be a cutting edge formed in the edge portion of a plurality of opening portions formed in a cylindrical portion. Alternatively, as in a third modification example illustrated in FIG. 25C, a cutting portion 208 may be a cutting edge formed in the edge portion of a plurality of slits formed in the cylindrical portion.

For example, the rotary structure 200 material can be preferably be stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide.

As illustrated in FIG. 23, the operation unit 210 includes the drive mechanism 93 for applying a rotational force to the drive shaft 60.

Figure 26:
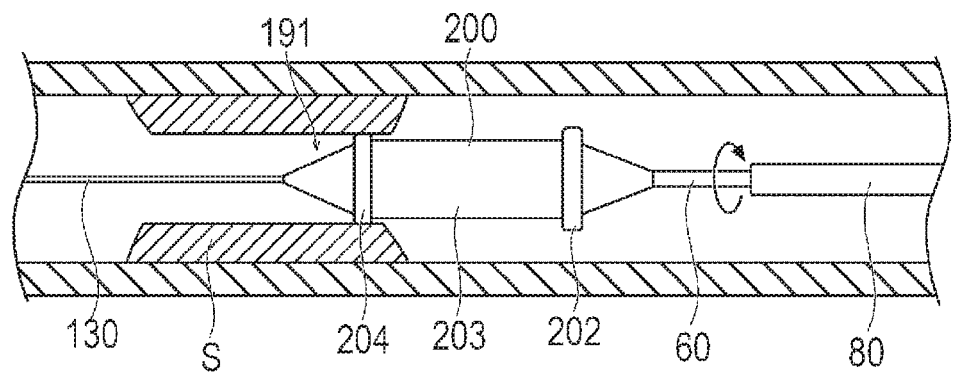
FIG. 26 is a schematic cross-sectional view illustrating an intravascular state when a medical procedure is performed using the medical device according to the fifth embodiment.

When the object inside the biological lumen is cut using the medical device 190 according to the fifth embodiment, the treatment device 191 is inserted into the blood vessel via the guiding catheter 140. Thereafter, as illustrated in FIG. 26, the rotary structure 200 is exposed inside the blood vessel. Thereafter, the drive shaft 60 is rotated so as to rotate the rotary structure 200. If the rotary structure 200 is moved forward, the cutting portion 203 comes into contact with the stenosed site S so as to cut the stenosed site S. In this case, the first non-cutting portion 202 and the second non-cutting portion 204 help prevent the cutting portion 203 from coming into contact with the biological tissue. Therefore, the damage to the biological tissue is prevented, and the safety of the medical device and treatment method can be improved. In addition, the outer diameter of the second non-cutting portion 204 is smaller than the outer diameter of the first non-cutting portion 202. Accordingly, the rotary structure 200 is likely to be pushed forward to the stenosed site S.

Sixth Embodiment

A medical device 210 according to a sixth embodiment of the present disclosure is different from that according to the fifth embodiment only in that each structure of the first non-cutting portion and the second non-cutting portion is different. The same reference numerals will be given to elements having functions which are the same as those according to the first and fifth embodiments, and description of the reference number, elements, and functions will be omitted.

Figure 27A:
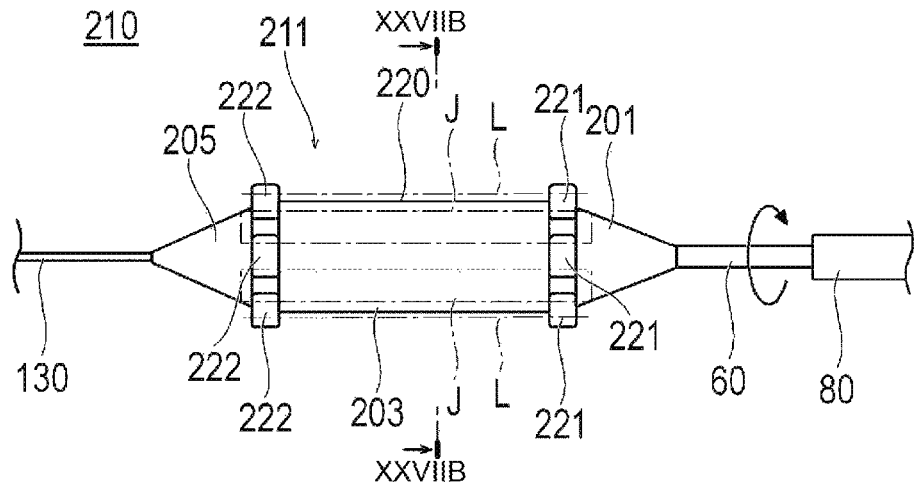
Figure 27B:
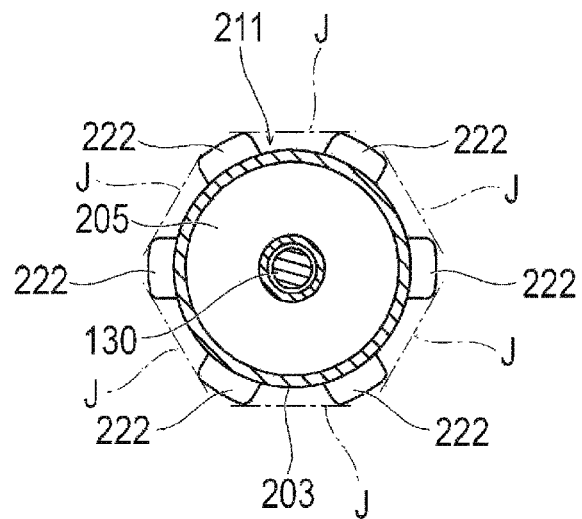

As illustrated in FIG. 27, in a treatment device 211 of the medical device 210 according to the sixth embodiment, a first non-cutting portion 221 and a second non-cutting portion 222 which are disposed in a rotary structure 220 are arranged by being divided in the circumferential direction. In each portion where the first non-cutting portion 221 is divided in the circumferential direction, an end portion in the circumferential direction is formed using a smooth curved surface so as not to damage the biological tissue when rotated. In addition, in each portion where the second non-cutting portion 222 is divided in the circumferential direction, an end portion in the circumferential direction is also formed using a smooth curved surface so as not to damage the biological tissue when rotated.

When the object inside the biological lumen is cut using the medical device 210 according to the sixth embodiment, the cutting portion 203 is located on the inside of the tangential line L between the first non-cutting portion 221 and the second non-cutting portion 222 in the cross section along the axial direction. Accordingly, while the rotating cutting portion 203 properly cuts the object inside the biological lumen, the first non-cutting portion 221 and the second non-cutting portion 222 help prevent the cutting portion 203 from coming into contact with the biological tissue. Therefore, the relative safety of the medical device and treatment method can be improved by reducing the damage to the biological tissue.

In addition, the first non-cutting portion 221 and the second non-cutting portion 222 are divided in the circumferential direction. Accordingly, in a cross section in the axial direction at a position where the first non-cutting portion 221 and the second non-cutting portion 222 are not present, the cutting portion 203 is located inside a contact surface J where the first non-cutting portion 221 and the second non-cutting portion 222 which are adjacent to each other are in contact with each other. Therefore, even if the first non-cutting portion 221 and the second non-cutting portion 222 are divided and arranged, the first non-cutting portion 221 and the second non-cutting portion 222 can help prevent the cutting portion 203 from coming into contact with the biological tissue.

Figure 28:
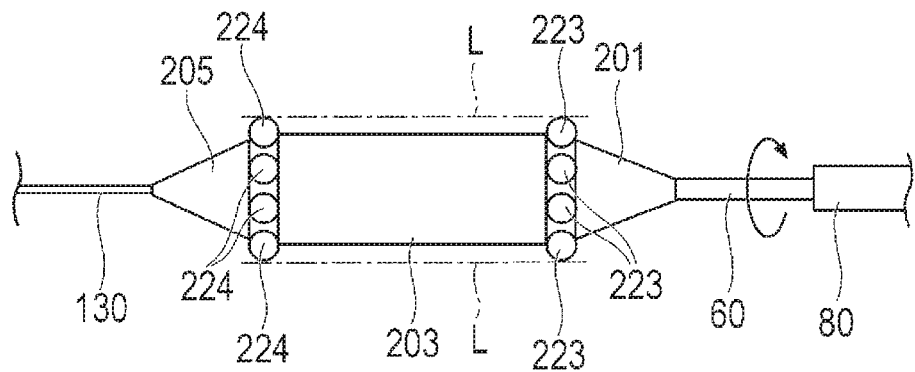
FIG. 28 is a plan view illustrating a modification example of the medical device according to the sixth embodiment.

Each shape of the first non-cutting portion and the second non-cutting portion is not particularly limited. For example, as in a modification example illustrated in FIG. 28, each divided portion in the circumferential direction of the first non-cutting portion 223 and the second non-cutting portion 224 may have a spherical shape.

Seventh Embodiment

A medical device 230 according to a seventh embodiment of the present disclosure is different from that according to the fifth embodiment in that the cutting portion is disposed on both sides of the distal side and the proximal side of the first non-cutting portion. The same reference numerals will be given to elements having functions which are the same as those according to the first and fifth embodiments, and description of the reference number, elements, and functions will be omitted.

Figure 29A:
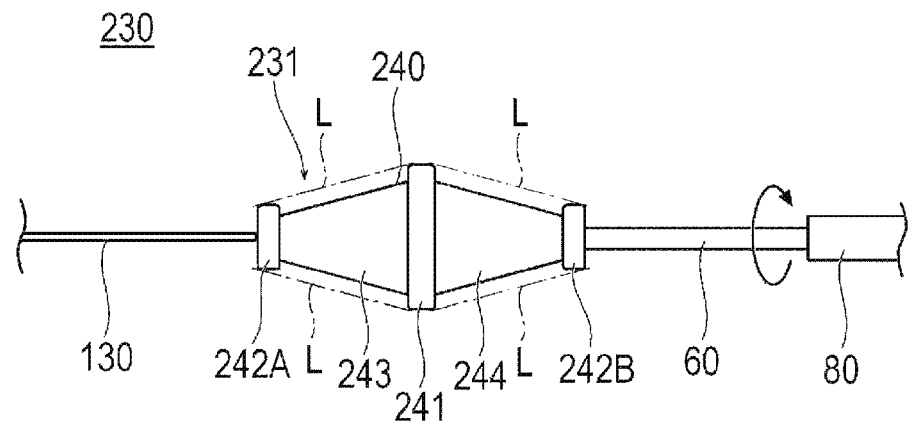

As illustrated in FIG. 29A, in a treatment device 231 of the medical device 230 according to the seventh embodiment, a distal cutting portion 243 (cutting portion) is disposed on the distal side of a first non-cutting portion 241 having a rotary structure 240, and a proximal cutting portion 244 (cutting portion) is disposed on the proximal side of the first non-cutting portion 241. Then, a second non-cutting portion 242A is disposed on the distal side of the distal cutting portion 243, and the other second non-cutting portion 242B is disposed on the proximal side of the proximal cutting portion 244. The two second non-cutting portions 242A and 242B are formed so as to have a smaller outer diameter than that of the first non-cutting portion 241.

The distal cutting portion 243 is formed in a tapered shape so that the diameter decreases toward the distal side, and the proximal cutting portion 244 is formed in a tapered shape so that the diameter decreases toward the proximal side. A polishing material, for example, a diamond particle adheres to the outer surface of the distal cutting portion 243 and the proximal cutting portion 244. The distal cutting portion 243 is located inside the tangential line L between the first non-cutting portion 241 in the cross section along the axial direction and the second non-cutting portion 242 on the distal side. In addition, the proximal cutting portion 244 is located inside the tangential line L between the first non-cutting portion 241 in the cross section along the axial direction and the second non-cutting portion 242 on the proximal side.

When the object inside the biological lumen is cut using the medical device 230 according to the seventh embodiment, the distal cutting portion 243 and the proximal cutting portion 244 are located inside the tangential line L between the first non-cutting portion 241 and the second non-cutting portion 242 in the cross section along the axial direction. Accordingly, in both cases where the rotary structure 240 is pushed forward and where the rotary structure 240 is pulled back, the rotating distal cutting portion 243 and the rotating proximal cutting portion 244 can effectively cut the object inside the biological lumen. Furthermore, the first non-cutting portion 241 and the second non-cutting portion 242 help prevent the distal cutting portion 243 and the proximal cutting portion 244 from coming into contact with the biological tissue. Therefore, the relative safety of the medical device and treatment method can be improved by reducing the damage to the biological tissue.

As described above, in the medical device 230 according to the seventh embodiment, the second non-cutting portions 242A and 242B are disposed on both the distal side and the proximal side of the first non-cutting portion 241, the cutting portions 243 and 244 are disposed on both sides between the first non-cutting portion 241 and the second non-cutting portion 242A on the distal side and between the first non-cutting portion 241 and the second non-cutting portion 242B on the proximal side. In this manner, the medical device 230 can cut the object by using the distal cutting portion 243 and the proximal cutting portion 244 which are located on the distal side and the proximal side of the first non-cutting portion 241. Therefore, cutting efficiency can be improved. In addition, the distal cutting portion 243 is formed in a tapered shape so that the diameter decreases toward the distal side. Accordingly, when the treatment device 231 is pushed forward to the distal side, the object can be effectively cut by the distal cutting portion 243. In addition, the proximal cutting portion 244 is formed in a tapered shape so that the diameter decreases toward the proximal side. Accordingly, when the treatment device 231 is pulled back to the proximal side, the object can be effectively cut by the proximal cutting portion 244.

Figure 29B:
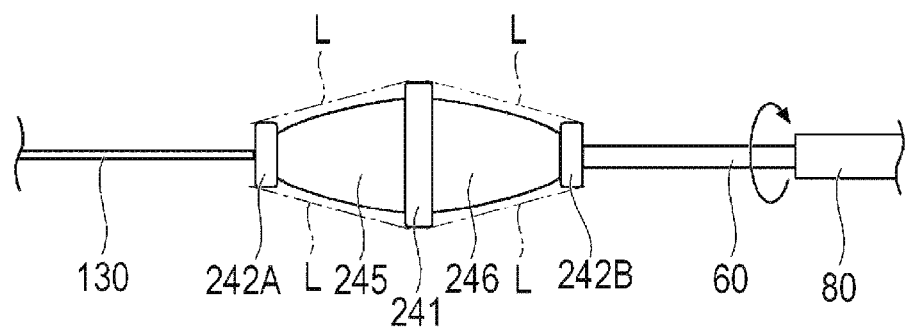

Each form of the distal cutting portion and the proximal cutting portion is not particularly limited. For example, as in a modification example illustrated in FIG. 29B, the distal cutting portion 245 and the proximal cutting portion 246 may protrude so that the central portion bulges in the cross section in the axial direction.

Eighth Embodiment

A medical device 250 according to an eighth embodiment of the present disclosure is different from that according to the fifth embodiment only in that a structure of the rotary structure is different. The same reference numerals will be given to elements having functions which are the same as those according to the first and fifth embodiments, and description of the reference number, elements, and functions will be omitted.

Figure 30:
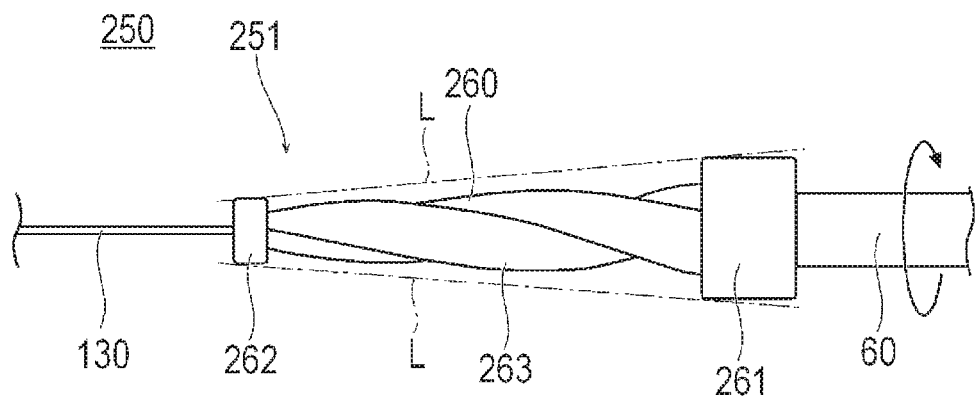
FIG. 30 is a plan view illustrating a treatment device of a medical device according to an eighth embodiment.

In a treatment device 251 of the medical device 250 according to the eighth embodiment, a drill-shaped cutting portion 263 having a spiral cutting edge is formed between a first non-cutting portion 261 and a second non-cutting portion 262 which are disposed in a rotary structure 260 as illustrated in FIG. 30. The outer diameter of the first non-cutting portion 261 is larger than the outer diameter of the second non-cutting portion 262. The cutting portion 263 is formed so that the outer diameter decreases toward the distal side. The cutting portion 263 is located inside the tangential line L between the first non-cutting portion 261 and the second non-cutting portion 262 in the cross-section along the axial direction.

For example, the rotary structure 260 material is preferably stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide.

When the object inside the biological lumen is cut using the medical device 250 according to the eighth embodiment, the cutting portion 263 is located inside the tangential line L between the first non-cutting portion 261 and the second non-cutting portion 262 in the cross section along the axial direction. Accordingly, while the rotating cutting portion 263 properly cuts the object inside the biological lumen, the first non-cutting portion 261 and the second non-cutting portion 262 help prevent the cutting portion 263 from coming into contact with the biological tissue. Therefore, the safety of the medical device and treatment method can be improved by reducing the damage to the biological tissue.

Ninth Embodiment

A medical device 270 according to a ninth embodiment of the present disclosure is different from that according to the fifth embodiment only in that a structure of the rotary structure is different. The same reference numerals will be given to elements having functions which are the same as those according to the first and fifth embodiments, and description of the reference number, elements, and functions will be omitted.

Figure 31:
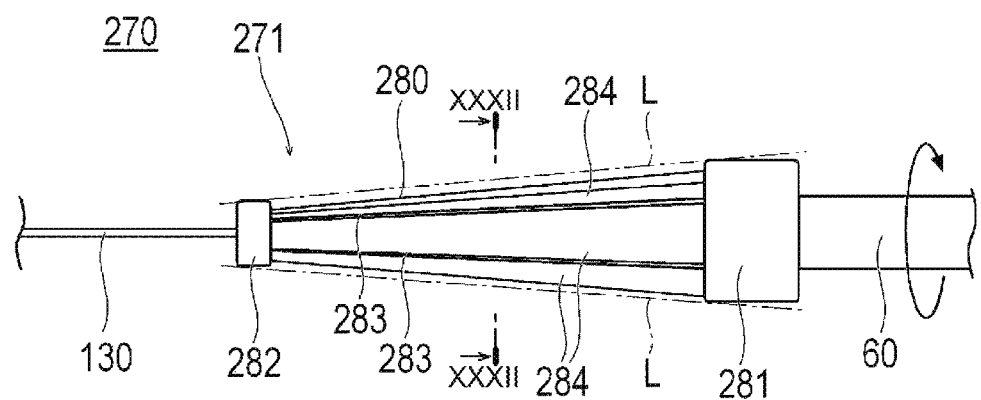
FIG. 31 is a plan view illustrating a treatment device of a medical device according to a ninth embodiment.
Figure 32:
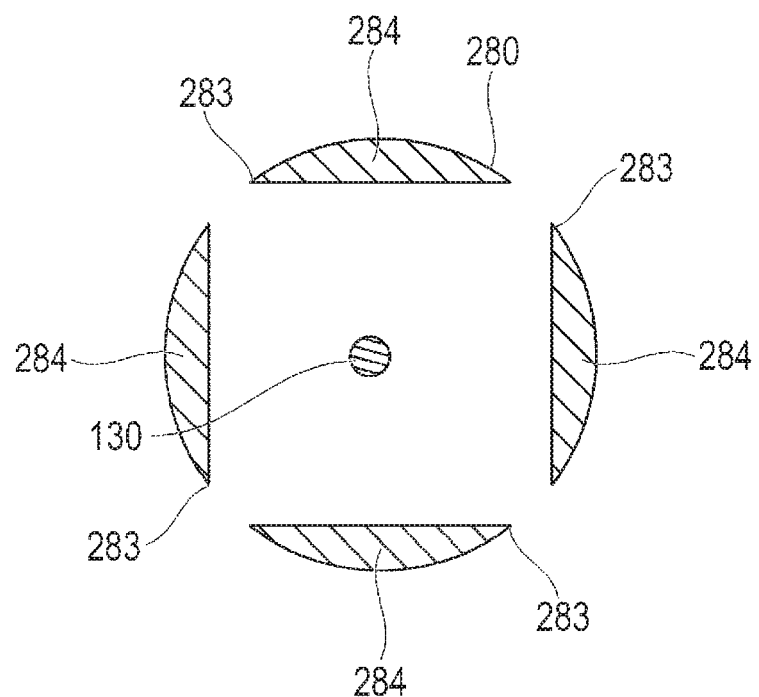
FIG. 32 is a cross-sectional view taken along line XXXII-XXXII in FIG. 31.

As illustrated in FIGS. 31 and 32, a treatment device 271 of the medical device 270 according to the ninth embodiment has a plurality of (four in the present embodiment) plate-shaped cutting members 284 between a first non-cutting portion 281 and a second non-cutting portion 282 which are disposed in a rotary structure 280. The cutting members 284 are arranged parallel to each other with an interval between each of the cutting members 284 in the circumferential direction. A cutting edge in the end portion in the circumferential direction of the respective cutting members 284 forms the cutting portion 283. As a whole, the plurality of cutting members 284 is formed in a tubular shape whose outer diameter decreases toward the distal side. The cutting portion 283 is located inside the tangential line L between the first non-cutting portion 281 and the second non-cutting portion 282 in the cross section along the axial direction.

For example, the rotary structure 280 material is preferably stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide.

When the object inside the biological lumen is cut using the medical device 270 according to the ninth embodiment, the cutting portion 283 is located inside the tangential line L between the first non-cutting portion 281 and the second non-cutting portion 282 in the cross section along the axial direction. Accordingly, while the rotating cutting portion 283 properly cuts the object inside the biological lumen, the first non-cutting portion 281 and the second non-cutting portion 282 help prevent the cutting portion 283 from coming into contact with the biological tissue. Therefore, the relative safety of the medical device and treatment method can be improved by reducing the damage to the biological tissue.

In addition, a gap (or space) is formed between the cutting portions 283. Accordingly, the cut debris can be discharged out of the body by aspirating the debris from the proximal side via the guide wire lumen.

Tenth Embodiment

A medical device 290 according to a tenth embodiment of the present disclosure is different from that according to the ninth embodiment only in that a weight is added to the rotary structure 280. The same reference numerals will be given to elements having functions which are the same as those according to the first and ninth embodiments, and description of the reference number, elements, and functions will be omitted.

Figure 33:
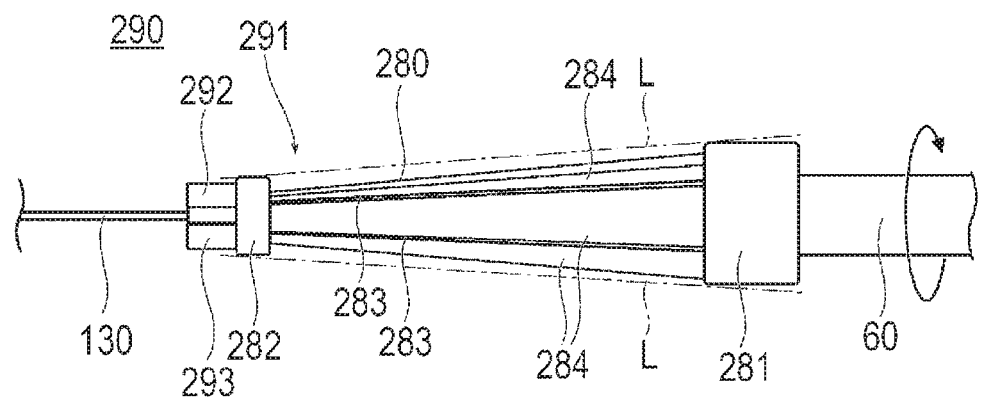
FIG. 33 is a plan view illustrating a treatment device of a medical device according to a tenth embodiment.
Figures 34A, 34B:
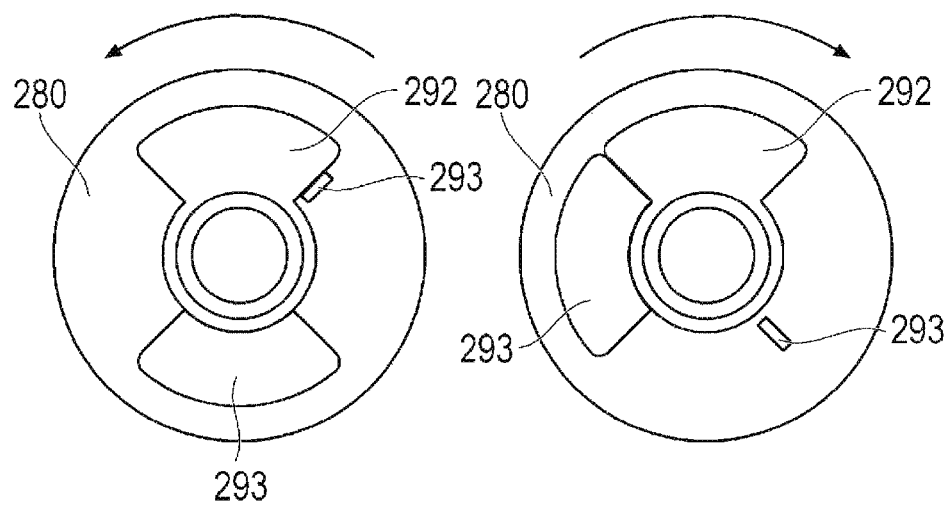

As illustrated in FIG. 33, in a treatment device 291 of the medical device 290 according to the tenth embodiment, the distal portion of a rotary structure 280 is provided with a stationary weight 293 located by being fixed to the rotary structure 280, and a rotary weight 292 located so as to rotatable relative to the stationary weight 293. The weight balance of the stationary weight 293 is biased toward one side in the circumferential direction. The rotary weight 292 is rotated toward one side relative to the stationary weight 293. Accordingly, as illustrated in FIG. 34A, the rotary weight 292 comes into contact with a stopper 293, and is brought into a first state where the weight balance is biased in a direction opposite to the stationary weight 293. The rotary weight 292 is rotated toward the other side relative to the stationary weight 293. Accordingly, as illustrated in FIG. 34B, the rotary weight 292 comes into contact with the stationary weight 293, and is brought into a second state where the weight balance is not located opposite to the stationary weight 293.

For example, the stationary weight 293 material and the rotary weight 292 material are preferably stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide.

When the object inside the biological lumen is cut using the medical device 290 according to the tenth embodiment, if the drive shaft 60 is rotated to one side and the cutting is performed by the cutting portion 283, the rotary weight 292 is rotated relative to the stationary weight 293 after receiving of an external force from the vascular wall or the blood. Accordingly, as illustrated in FIG. 34A, the rotary weight 292 comes into contact with the stopper 293, and is brought into the first state. In this case, the stationary weight 293 and the rotary weight 292 are located at positions in the opposite direction, and the weight balance of the stationary weight 293 and the rotary weight 292 is satisfactorily established, thereby helping prevent the vibration of the rotary structure 280.

Next, if the drive shaft 60 is rotated to the opposite side and the cutting is performed by the cutting portion 283, the rotary weight 292 is rotated relative to the stationary weight 293 after receiving the external force from the vascular wall or the blood. Accordingly, as illustrated in FIG. 34B, the rotary weight 292 comes into contact with the stationary weight 293, and is brought into the second state. In this case, the stationary weight 293 and the rotary weight 292 are not located at the positions in the opposite direction, and are brought into a state where the weight balance to which the stationary weight 293 and the rotary weight 292 are added is biased. Accordingly, the swinging of the rotary structure 280 is induced, thereby enabling the rotary structure 280 to cut the object in a wide range inside the biological lumen.

As described above, in a treatment method for cutting the object inside the biological lumen by using the medical device 290 according to the tenth embodiment, in cutting step, the weight balance of the rotary structure 280 in the circumferential direction is changed. In this manner, the position and the inclination of the rotary structure 280 can be adjusted inside the biological lumen. In this manner, the position and the inclination of the rotary structure 280 inside the biological lumen and the inclination can be rather easily adjusted by changing the weight balance. Therefore, a state suitable for the cutting can be achieved in accordance with a situation of the object inside the biological lumen that is being cut, and operability of the medical device can be improved.

Eleventh Embodiment

A medical device 300 according to an eleventh embodiment of the present disclosure is different from that according to the ninth embodiment only in that a weight is added to the rotary structure 280. The same reference numerals will be given to elements having functions which are the same as those according to the first and ninth embodiments, and description of the reference number, elements, and functions will be omitted.

Figure 35:
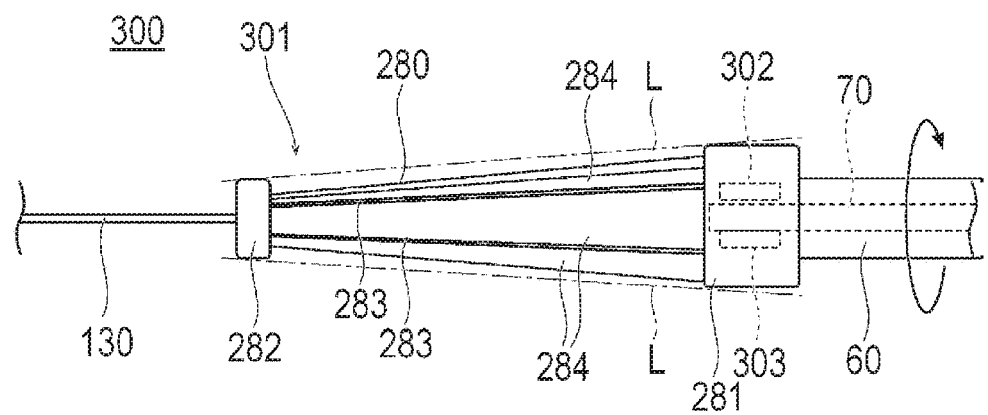
FIG. 35 is a plan view illustrating a first state of a treatment device of a medical device according to an eleventh embodiment.

As illustrated in FIG. 35, in a treatment device 301 of the medical device 300 according to the eleventh embodiment, the rotary structure 280 internally has a stationary weight 302 located by being fixed to the rotary structure 280, and a moving weight 303 which is movable relative to the stationary weight 302 in the axial direction. The weight balance of the stationary weight 302 is biased to one side in the circumferential direction. The moving weight 303 is fixed to the linear motion shaft 70 which can be moved in the axial direction by the hand operation, and can be brought into the first state where the weight balance is biased in the direction opposite to the stationary weight 302. In addition, the moving weight 303 is moved in the axial direction by the linear motion shaft 70. In this manner, as illustrated in FIG. 36, the moving weight 303 is moved toward the distal side or the proximal side relative to the stationary weight 302 in the axial direction, and can be brought into the second state.

For example, the stationary weight 302 material and the moving weight 303 material are preferably stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide.

When the object inside the biological lumen is cut using the medical device 300 according to the eleventh embodiment, if the linear motion shaft 70 is operated and the cutting is performed as the first state by the cutting portion 283, the stationary weight 302 and the moving weight 303 are located at the positions in the opposite direction. As illustrated in FIG. 35, the weight balance of the stationary weight 302 and the moving weight 303 is satisfactorily established, thereby helping prevent the vibration of the rotary structure 280.

Figure 36:
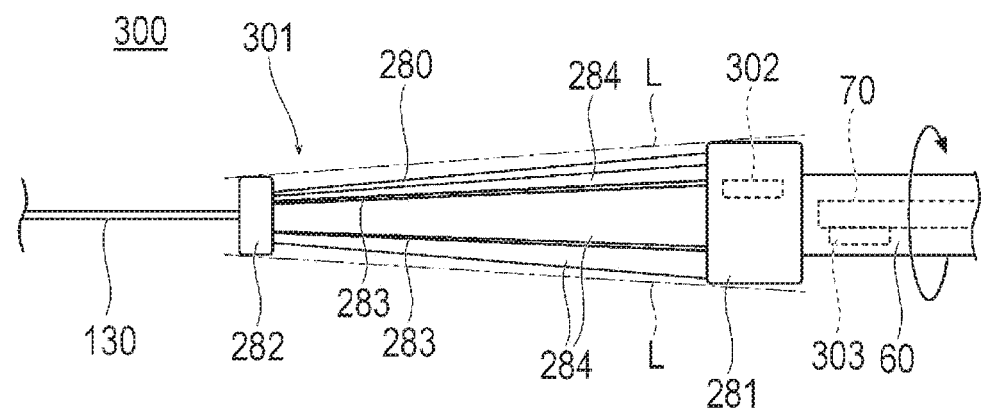
FIG. 36 is a plan view illustrating a second state of the treatment device of the medical device according to the eleventh embodiment.

Next, if the linear motion shaft 70 is operated and the cutting is performed as the second state by the cutting portion 283, as illustrated in FIG. 36, the respective positions of the stationary weight 302 and the moving weight 303 in the axial direction are different from each other. The stationary weight 302 and the moving weight 303 are brought into a state where the weight balance to which the stationary weight 302 and the moving weight 303 are added is biased. Accordingly, the swinging of the rotary structure 280 is induced, thereby enabling the rotary structure 280 to cut the object in a wide range inside the biological lumen.

Twelfth Embodiment

Figure 37:
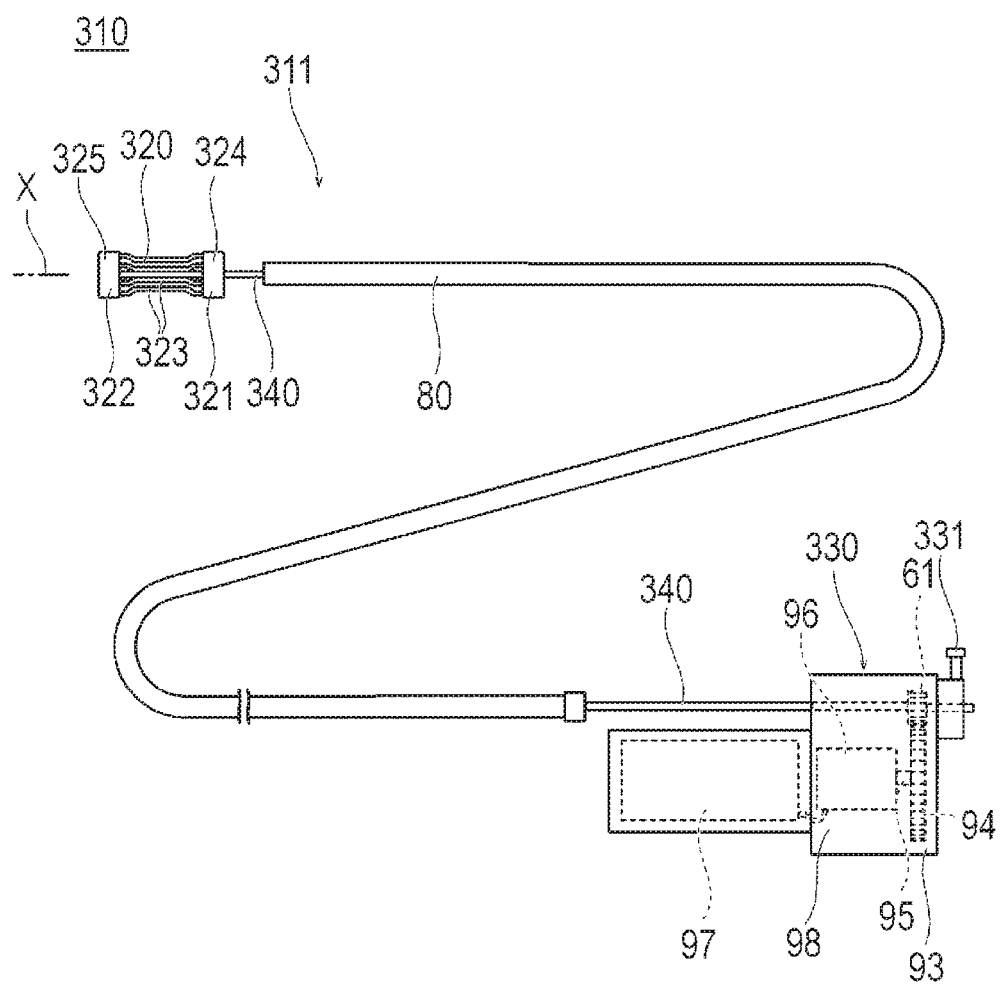
FIG. 37 is a plan view illustrating a treatment device of a medical device according to a twelfth embodiment.
Figure 38:
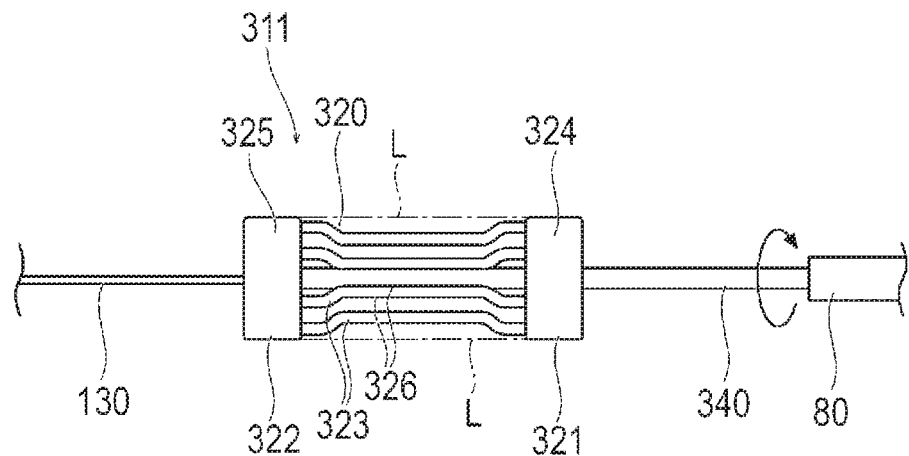
FIG. 38 is a plan view illustrating a distal portion of the treatment device according to the twelfth embodiment.

A medical device 310 according to a twelfth embodiment of the present disclosure is different from that according to the fifth embodiment in that the rotary structure is expanded and contracted by a balloon as illustrated in FIGS. 37 and 38. The same reference numerals will be given to elements having functions which are the same as those according to the first and fifth embodiments, and description of the reference number, elements, and functions will be omitted.

A treatment device 311 of the medical device 310 according to the twelfth embodiment includes a rotatable rotary structure 320, a drive shaft 340 for rotating the rotary structure 320, an outer sheath 80 capable of accommodating the rotary structure 320, and an operation unit 330 disposed on the hand side (proximal) for operation.

The rotary structure 320 includes a proximal side balloon 321, a distal side balloon 322 separated from the proximal side balloon 321 and disposed on the distal side, and a plurality of beam-shaped cutting members 323 arranged between the proximal side balloon 321 and the distal side balloon 322. The proximal side balloon 321 and the distal side balloon 322 are internally hollow, are inflated in the radial direction by a fluid flowing into the proximal side balloon 321 and the distal side balloon 322, and are deflated in the radial direction by discharging the fluid. The drive shaft 340 has a coaxial double tube structure. A lumen between two tubes is an inflating lumen which communicates with the proximal side balloon 321 and the distal side balloon 322. The inflating lumen circulates the fluid in order to inflate or deflate the proximal side balloon 321 and the distal side balloon 322. The lumen closest to the inner side of the drive shaft 340 is the guide wire lumen into which the guide wire can be inserted. A first non-cutting portion 324 is formed on the outer peripheral surface of the proximal side balloon 321, and a second non-cutting portion 325 is formed on the outer peripheral surface of the distal side balloon 322. The proximal side balloon 321 and the distal side balloon 322 have the same outer diameter, but may have mutually different outer diameters.

In the cutting member 323, the distal side portion is fixed to the proximal side of the distal side balloon 322, and the proximal side portion is fixed to the distal side of the proximal side balloon 321. The plurality of cutting members 323 are arranged parallel to each other with an interval between each of the plurality of cutting members 323 in the circumferential direction, and an edge (cutting edge) of the end portion of each cutting member 323 in the circumferential direction configures a cutting portion 326. The cutting portion 326 is located inside the tangential line L between the first non-cutting portion 324 and the second non-cutting portion 325 in the cross-section along the axial direction. If the proximal side balloon 321 and the distal side balloon 322 are inflated, the cutting member 323 moves so that a gap (or space) is widened in the circumferential direction and the outer diameter increases as a whole. In addition, if the proximal side balloon 321 and the distal side balloon 322 are deflated, the cutting member 323 moves so that the gap is narrowed in the circumferential direction and the outer diameter decreases as a whole. The cutting member 323 is formed so that the central portion is recessed in the cross section in the axial direction. However, the shape is not limited as long as the cutting portion 326 is located inside the tangential line L in a state where the proximal side balloon 321 and the distal side balloon 322 are inflated.

The cutting member 323 material is not particularly limited. However, for example, the cutting member 323 material is preferably stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide.

The proximal side balloon 321 material and the distal side balloon 322 material, for example, are preferably a polyolefin such as polyethylene, polypropylene, polybutene, ethylene-propylene copolymer, ethylene-vinyl acetate copolymer, ionomer, or a mixture of two or more of these materials, thermoplastic resin such as soft polychlorinated vinyl resin, polyamide, polyamide elastomer, polyester, polyester elastomer, polyurethane, and fluorine resin, silicone rubber, or latex rubber.

The operation unit 330 is provided with a port 331 on the proximal side of the drive mechanism 93 which applies a rotational force to the drive shaft 340. The port 331 rotatably accommodates the end portion of the rotating drive shaft 340, and communicates with the inflating lumen of the drive shaft 340. The port 331 can be connected to a syringe accommodating an inflating fluid such as saline (saline solution) and a contrast agent.

When the object inside the biological lumen is cut using the medical device 310 according to the twelfth embodiment, the treatment device 311 is inserted into the blood vessel in a state where the proximal side balloon 321 and the distal side balloon 322 are deflated, and is pushed forward to reach a desired position. Thereafter, the syringe for accommodating the inflating fluid is connected to the port 331 so as to supply the inflating fluid. In this manner, the inflating fluid flows into the proximal side balloon 321 and the distal side balloon 322 through the inflating lumen, and the proximal side balloon 321 and the distal side balloon 322 are inflated. In this manner, the gap is widened in the circumferential direction of the cutting member 323, and the cutting member 323 moves so that the diameter increases as a whole. Thereafter, if the drive shaft 340 is rotated, the cutting portion 326 of the rotary structure 320 is rotated so as to cut the object inside the biological lumen. In this case, the cutting portion 326 is located inside the tangential line L between the first non-cutting portion 324 and the second non-cutting portion 325. Accordingly, the first non-cutting portion 324 and the second non-cutting portion 325 help prevent the cutting portion 326 from coming into contact with the biological tissue. Therefore, the relative safety of the medical device and treatment method can be improved. After the object inside the biological lumen is cut, the fluid inside the proximal side balloon 321 and the distal side balloon 322 is discharged via the inflating lumen. In this manner, the proximal side balloon 321 and the distal side balloon 322 are deflated, and the cutting member 323 moves so that the diameter decreases as a whole. In this manner, the treatment device 311 can be smoothly removed from the blood vessel.

As described above, in the medical device 310 according to the twelfth embodiment, the first non-cutting portion 324 and the second non-cutting portion 325 are arranged in the proximal side balloon 321 and the distal side balloon 322 which can be inflated and deflated in the radial direction by causing the fluid to flow into and flow out from the proximal side balloon 321 and the distal side balloon 322. In this manner, the proximal side balloon 321 and the distal side balloon 322 are deflated. Accordingly, the medical device 310 is rather easily moved into a narrow lumen. In addition, the proximal side balloon 321 and the distal side balloon 322 are inflated so as to increase the diameter of the cutting portion 326. Accordingly, the cutting portion 326 can be set to have a desired size for the cutting.

Thirteenth Embodiment

Figure 39:
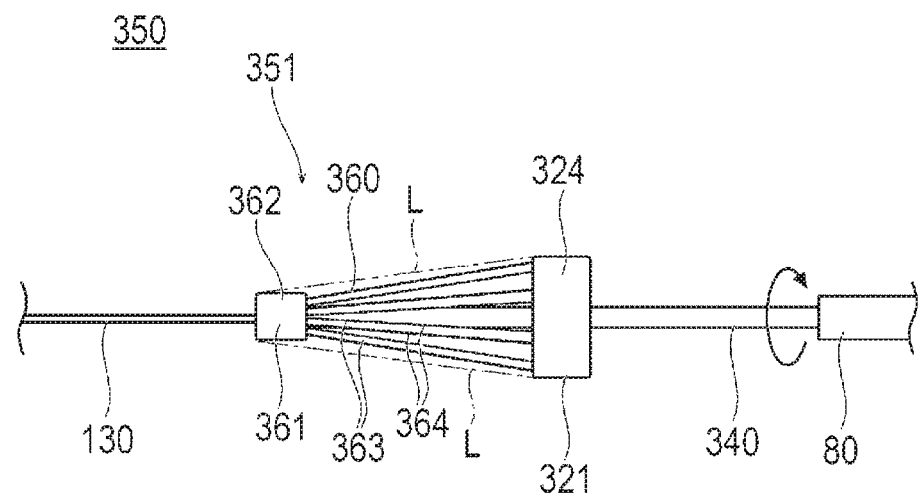
FIG. 39 is a plan view illustrating a treatment device of a medical device according to a thirteenth embodiment.

A medical device 350 according to a thirteenth embodiment of the present disclosure is different from that according to the twelfth embodiment in that only the proximal portion of the rotary structure is expanded and contracted by the balloon as illustrated in FIG. 39. The same reference numerals will be given to elements having functions which are the same as those according to the first and twelfth embodiments, and description of the reference number, elements, and functions will be omitted.

A treatment device 351 of the medical device 350 according to the thirteenth embodiment includes a rotatable rotary structure 360, a drive shaft 340 for rotating the rotary structure 360, the outer sheath 80 capable of accommodating the rotary structure 320, and the operation unit 330 (refer to FIG. 37) disposed on the hand side (proximal side) for operation.

The rotary structure 360 includes the proximal side balloon 321, a tubular body 361 which is not the balloon separated from the proximal side balloon 321 and disposed on the distal side, and a plurality of beam-shaped cutting members 363 arranged between the proximal side balloon 321 and the tubular body 361. The proximal side balloon 321 is internally hollow, is inflated in the radial direction by the fluid flowing into the proximal side balloon 321, and is deflated in the radial direction by discharging the fluid. The drive shaft 340 has a coaxial double tube structure. A lumen between two tubes is an inflating lumen which communicates with the proximal side balloon 321. The inflating lumen circulates the fluid in order to inflate or deflate the proximal side balloon 321. The first non-cutting portion 324 is formed on the outer peripheral surface of the proximal side balloon 321, and the second non-cutting portion 362 is formed on the outer peripheral surface of the tubular body 361. The outer diameter of the inflated proximal side balloon 321 is larger than the outer diameter of the tubular body 361.

In the cutting member 363, the distal side portion is fixed to the proximal side of the tubular body 361, and the proximal side portion is fixed to the distal side of the proximal side balloon 321. The plurality of cutting members 363 are arranged parallel to each other with an interval between each of the plurality of cutting members 363 in the circumferential direction, and an edge (cutting edge) of the end portion of each cutting member 363 in the circumferential direction forms a cutting portion 364. The cutting portion 364 is located inside the tangential line L between the first non-cutting portion 324 and the second non-cutting portion 362 and in the cross section along the axial direction. If the proximal side balloon 321 is inflated, the cutting member 363 moves so that a gap is widened in the circumferential direction and the outer diameter increases as a whole. In addition, if the proximal side balloon 321 is deflated, the cutting member 323 moves so that the gap (or space) is narrowed in the circumferential direction and the outer diameter decreases as a whole.

The cutting member 363 material is not particularly limited. However, for example, the cutting member 363 material is preferably stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide.

When the object inside the biological lumen is cut using the medical device 350 according to the thirteenth embodiment, the treatment device 351 is inserted into the blood vessel in a state where the proximal side balloon 321 is deflated, and is pushed forward to reach a desired position. Thereafter, the syringe for accommodating the inflating fluid is connected to the port 331 (refer to FIG. 37) so as to supply the inflating fluid. In this manner, the inflating fluid flows into the proximal side balloon 321 through the inflating lumen, and the proximal side balloon 321 is inflated. If the proximal side balloon 321 is inflated, the gap is widened in the circumferential direction in the proximal portion of the cutting member 363, and the cutting member 363 moves so that the diameter decreases in a circular cone whose distal side is narrow as a whole. Thereafter, if the drive shaft 340 is rotated, the cutting portion 364 of the rotary structure 360 is rotated, and the object inside the biological lumen can be cut. In this case, the cutting portion 64 is located inside the tangential line L between the first non-cutting portion 324 and the second non-cutting portion 362. Accordingly, the first non-cutting portion 324 and the second non-cutting portion 362 help prevent the cutting portion 364 from coming into contact with the biological tissue. Therefore, the relative safety of the medical device 350 can be improved. Furthermore, the cutting portion 364 is formed in a tapered shape so that the diameter decreases toward the distal side. Accordingly, when the treatment device 351 is pushed forward to the distal side, the object can be effectively cut by the cutting portion 364.

After the object inside the biological lumen is cut, the proximal side balloon 321 is deflated by discharging the fluid inside the proximal side balloon 321 via the inflating lumen, and the cutting member 363 is moved so that the diameter decreases as a whole. In this manner, the treatment device 351 is removed from the blood vessel.

As described above, in the medical device 350 according to the thirteenth embodiment, the first non-cutting portion 324 is located in the proximal side balloon 321 which can be inflated and deflated in the radial direction by causing the fluid to flow into and flow out from the proximal side balloon 321. In this manner, the proximal side balloon 321 is deflated. Accordingly, the medical device 350 can be moved rather easily into a narrow lumen. In addition, the proximal side balloon 321 is inflated so as to increase the diameter of the cutting portion 364. Accordingly, the cutting portion 364 can be set to have a desired size for the cutting.

Fourteenth Embodiment

Figure 40:
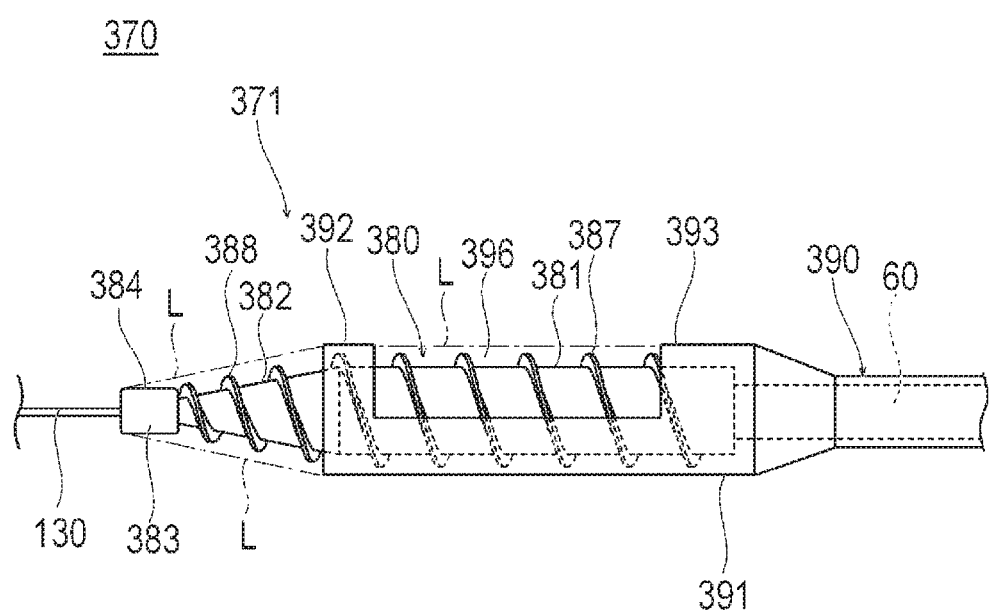
FIG. 40 is a plan view illustrating a treatment device of a medical device according to a fourteenth embodiment.

A medical device 370 according to a fourteenth embodiment of the present disclosure is different from that according to the fifth embodiment in that each structure of a rotary structure 380 and an outer sheath 390 is different as illustrated in FIG. 40. The same reference numerals will be given to elements having functions which are the same as those according to the first and fifth embodiments, and description of the reference number, elements, and functions will be omitted.

A treatment device 371 of the medical device 370 according to the fourteenth embodiment includes a rotatable rotary structure 380, the drive shaft 60 for rotating the rotary structure 380, an outer sheath 80 capable of accommodating the rotary structure 380, and the operation unit 210 (refer to FIG. 23) disposed on the hand side (proximal side) for operation.

The rotary structure 380 includes a cylindrical portion 381 having a cylindrical shape, a tapered portion 382 whose diameter decreases from the distal portion of the cylindrical portion 381 toward the distal side, and a tubular body 383 located on the distal side of the tapered portion 382. A second non-cutting portion 384 is formed on the outer peripheral surface of the tubular body 383.

The cylindrical portion 381 has a constant outer diameter, and a proximal cutting portion 387 (cutting portion) serving as a spiral cutting edge is formed on the outer peripheral surface. In the tapered portion 382, a distal cutting portion 388 (cutting portion) serving as a spiral cutting edge is formed on the outer peripheral surface.

The rotary structure 380 material is not particularly limited. However, for example, the rotary structure 380 material is preferably stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide.

An accommodation unit 391 having a larger outer diameter and inner diameter than the proximal side is formed in an end portion on the distal side of the outer sheath 390. The accommodation unit 391 can accommodate the proximal cutting portion 387 of the rotary structure 380. The outer sheath 390 is movable relative to the drive shaft 60 and the rotary structure 380 in the axial direction. A first non-cutting portion 392 is formed on the outer peripheral surface of the distal portion of the accommodation unit 391, and a second non-cutting portion 393 is formed closer to the proximal side than the first non-cutting portion 392 of the accommodation unit 391. An opening portion 396 penetrating from the outer peripheral surface to the inner peripheral surface is formed between the first non-cutting portion 392 and the second non-cutting portion 393 of the accommodation unit 391. The opening portion 396 is formed at an angle smaller than 360 degrees in the circumferential direction.

Figure 41A:
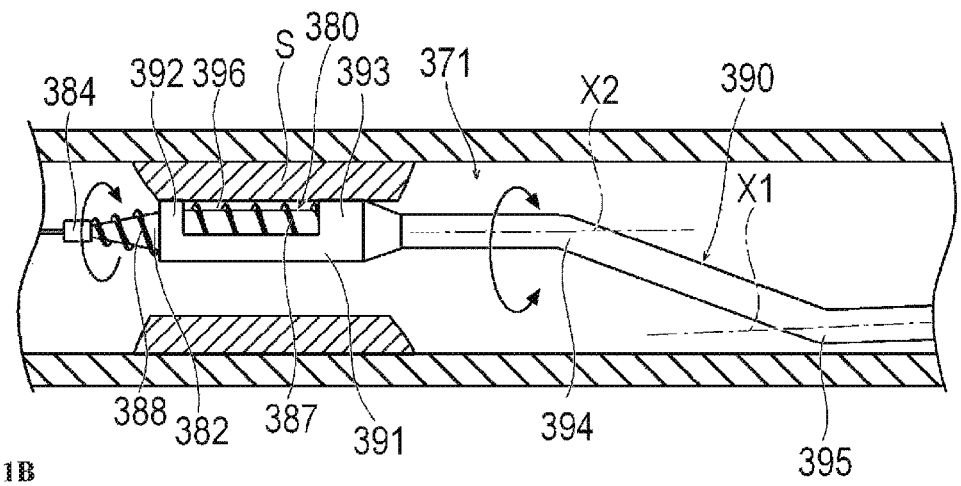

As illustrated in FIG. 41A, in the outer sheath 390, a first curved portion 394 is formed closer to the proximal side than the accommodation unit 391, and a second curved portion 395 is formed closer to the proximal side than the first curved portion 394. The first curved portion 394 and the second curved portion 395 are curved at the same angle in opposite directions. Therefore, a central axis X1 in a portion closer to the proximal side than the second curved portion 395 of the outer sheath 390 and a central axis X2 in a portion closer to the distal side than the first curved portion 394 of the outer sheath 390 are separated from each other while being substantially parallel to each other. The opening portion 396 of the accommodation unit 391 is formed on a side opposite to a side where the central axis X2 is located with respect to the central axis X1.

In a state where the accommodation unit 391 of the outer sheath 390 accommodates the proximal cutting portion 387, the proximal cutting portion 387 exposed from the opening portion 396 is located inside the tangential line L between the first non-cutting portion 392 and the second non-cutting portion 393 in the cross section along the axial direction. In addition, the distal cutting portion 388 is located inside than the tangential line L between the first non-cutting portion 392 and the second non-cutting portion 384 of the rotary structure 380 in the cross section along the axial direction.

The outer sheath 390 material is not particularly limited. However, for example, the outer sheath 390 material is preferably a polyolefin such as polyethylene and polypropylene, polyester such as polyamide and polyethylene terephthalate, a fluorine-based polymer such as ETFE, polyether ether ketone (PEEK), or polyimide. In addition, the outer sheath 390 may be formed of a plurality of materials, and the reinforcement member such as the wire rod may be incorporated in the plurality of materials of the outer sheath 390.

When the stenosed site S inside the blood vessel is cut using the medical device 370 according to the fourteenth embodiment, the treatment device 371 is inserted into the blood vessel and the proximal cutting portion 387 is accommodated in the accommodation unit 391 of the outer sheath 390. If the drive shaft 60 is rotated in this state, as illustrated in FIG. 41A, the proximal cutting portion 387 and the distal cutting portion 388 of the rotary structure 380 are rotated, and the stenosed site S inside the biological lumen can be cut. In this case, the distal cutting portion 388 is located inside the tangential line L between the first non-cutting portion 392 and the second non-cutting portion 384. Accordingly, the distal cutting portion 388 is prevented from coming into contact with the biological tissue. Therefore, the relative safety of the medical device and treatment method can be improved. In addition, the distal cutting portion 388 is formed in the tapered portion 382 whose diameter decreases toward the distal side. Accordingly, the rotary structure 380 is pushed forward to the distal side, the stenosed site S can be effectively cut.

Figure 41B:
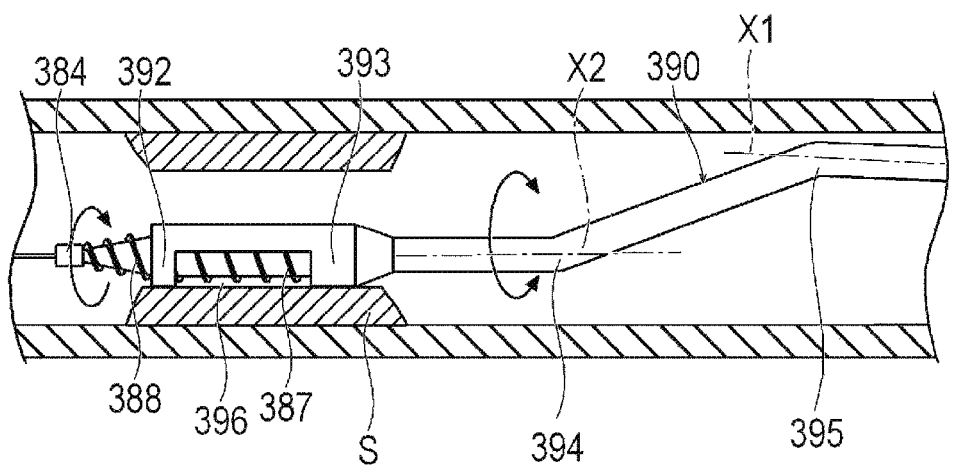

In addition, the proximal cutting portion 387 exposed from the opening portion 396 is located inside the tangential line L between the first non-cutting portion 392 and the second non-cutting portion 393. Accordingly, the proximal cutting portion 387 is prevented from coming into contact with the biological tissue. Therefore, the relative safety of the medical device and treatment method can be improved. In addition, the opening portion 396 is formed in a range equal to or smaller than 360 degrees in the circumferential direction. Accordingly, it is possible to limit the range in the circumferential direction which is to be cut by the proximal cutting portion 387. Therefore, a position to be cut by the proximal cutting portion 387 can be set to a suitable position in accordance with a situation of the object inside the biological lumen that is being cut. In addition, the opening portion 396 is formed on the side opposite to the side where the central axis X1 is located with respect to the central axis X2. Accordingly, the opening portion 396 moves close to the biological tissue, and the stenosed site S can be effectively cut by the proximal cutting portion 387. In addition, the outer sheath 390 is rotated around the central axis X1. In this manner, as illustrated in FIG. 41B, the opening portion 396 can be moved close to the biological tissue at the other position in the circumferential direction. In this way, while the outer sheath 390 is rotated, the cutting is performed by the proximal cutting portion 387. In this manner, the stenosed site S can be cut throughout the entire circumference, or can be partially cut. When the cutting is performed, the syringe can interlock with the proximal side of the outer sheath 390. In this manner, the cut object can be aspirated using the lumen of the outer sheath 390. In addition, the outer sheath 390 is moved closer to the proximal side than the rotary structure 380. In this manner, without accommodating the proximal cutting portion 387 in the accommodation unit 391, the stenosed site S can be cut by the proximal cutting portion 387.

As described above, the medical device 370 according to the fourteenth embodiment has the outer sheath 390 which can accommodate the drive shaft 60 so as to be relatively rotatable, which can cover a portion of the proximal cutting portion 387, and whose outer peripheral surface has at least one of the first non-cutting portion 392 and the second non-cutting portion 393 (both of these in the present embodiment). In this manner, the proximal cutting portion 387 is prevented from coming into contact with the biological tissue. Therefore, the relative safety of the medical device and treatment method can be improved by reducing the damage to the biological tissue. Furthermore, the first non-cutting portion 392 and the second non-cutting portion 393 are not rotated together with the proximal cutting portion 387. Accordingly, even if the first non-cutting portion 392 and the second non-cutting portion 393 come into contact with the biological tissue, a rotational force is less likely to act on the biological tissue. Therefore, a position of the proximal cutting portion 387 can be held at a desired position, and the cutting can be performed at the desired position.

In addition, the outer sheath 390 is movable relative to the drive shaft 60 along the axial direction. In this manner, the outer sheath 390 is moved relative to the proximal cutting portion 387 and the distal cutting portion 388. Accordingly, cutting conditions can be freely changed, and a state suitable for the cutting can be achieved in accordance with a situation of the object inside the biological lumen that is being cut. In a case where the first non-cutting portion 392 and the second non-cutting portion 393 are disposed in the outer sheath 390, the positions of the first non-cutting portion 392 and the second non-cutting portion 393 can be freely changed relative to the proximal cutting portion 387 and the distal cutting portion 388, and a state suitable for the cutting can be achieved in accordance with a situation of the object inside the biological lumen that is being cut.

In addition, in the outer sheath 390, the first non-cutting portion 392 and the second non-cutting portion 393 are arranged on the outer peripheral surface. The outer sheath 390 has the opening portion 396 which is located between the first non-cutting portion 392 and the second non-cutting portion 393, which penetrates from the outer peripheral surface to the inner peripheral surface in the range equal to or smaller than 360 degrees in the circumferential direction, and which exposes proximal cutting portion 387 accommodated in the outer sheath 390. In this manner, a position of the opening portion 396 of the outer sheath 390 is adjusted. Accordingly, it is possible to adjust the cutting position used by the proximal cutting portion 387 via the opening portion 396.

Fifteenth Embodiment

Figure 42:
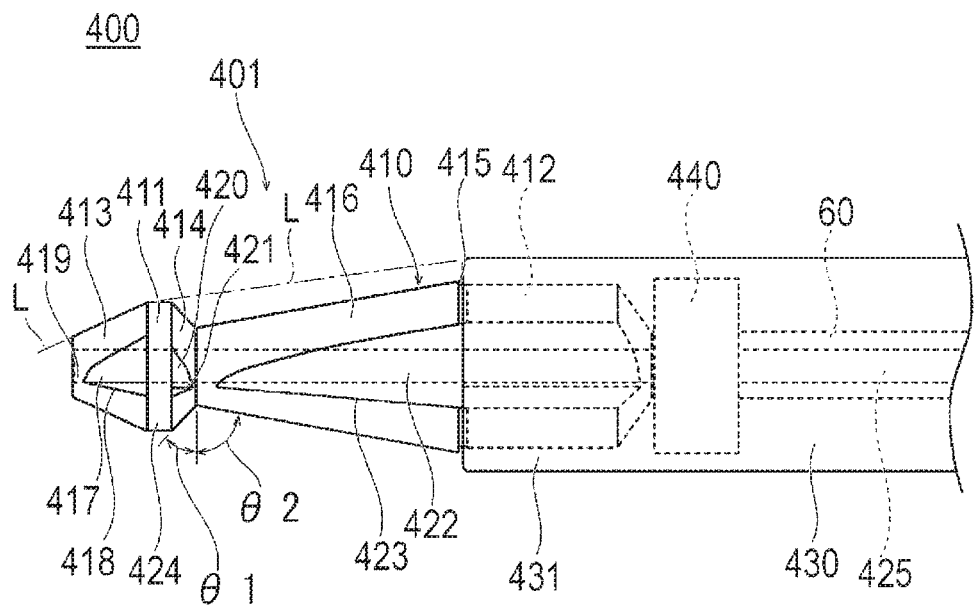
FIG. 42 is a plan view illustrating a treatment device of a medical device according to a fifteenth embodiment.
Figure 43:
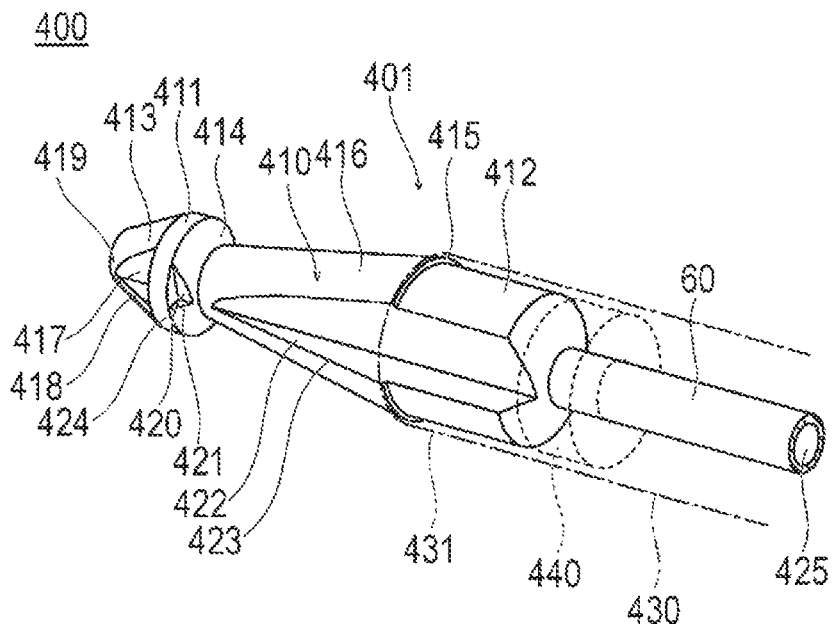
FIG. 43 is a perspective view illustrating the treatment device of the medical device according to the fifteenth embodiment.

A medical device 400 according to a fifteenth embodiment of the present disclosure is different from that according to the fifth embodiment in that a structure of the rotary structure 410 is different as illustrated in FIGS. 42 and 43. The same reference numerals will be given to elements having functions which are the same as those according to the first and fifth embodiments, and description of the reference number, elements, and functions will be omitted.

A treatment device 401 of the medical device 400 according to the fifteenth embodiment includes a rotatable rotary structure 410, the drive shaft 60 for rotating the rotary structure 410, an outer sheath 430 capable of accommodating the rotary structure 410, a bearing 440, and the operation unit 210 (refer to FIG. 23) disposed on the hand side for operation. The rotary structure 410 and the drive shaft 60 internally have a guide wire lumen 425.

The rotary structure 410 has a first cylindrical portion 411 having a cylindrical shape, and a second cylindrical portion 412 located closer to the proximal side than the first cylindrical portion 411. Furthermore, the rotary structure 410 has a first tapered portion 413 whose diameter decreases from the first cylindrical portion 411 toward the distal side, a second tapered portion 414 whose diameter decreases from the first cylindrical portion 411 toward the proximal side, a stepped portion 415 whose diameter increases in a stepped shape on the distal side of the second cylindrical portion 412, and a third tapered portion 416 whose diameter decreases from the stepped portion 415 toward the distal side. The first cylindrical portion 411 has a first non-cutting portion 424 disposed on the outer peripheral surface. The first tapered portion 413 has a first cutout portion 417 cut in a V-shape in an axially orthogonal cross section in a portion in the circumferential direction, and a first cutting portion 418 serving as a cutting edge is disposed in the edge portion of the first cutout portion 417. Only one first cutout portion 417 may be disposed in the circumferential direction, or two or more first cutout portions 417 may be disposed. In the first tapered portion 413, a second non-cutting portion 419 having no first cutout portion 417 in the circumferential direction is disposed on the outer peripheral surface of the distal side end portion. The second tapered portion 414 has a second cutout portion 420 cut in a V-shape in an axially orthogonal cross section in a portion in the circumferential direction, and a second cutting portion 421 serving as a cutting edge is disposed in the edge portion of the second cutout portion 420. Only one second cutout portion 420 may be disposed in the circumferential direction, or two or more second cutout portions 420 may be disposed. The third tapered portion 416 has a third cutout portion 422 cut in a V-shape in an axially orthogonal cross section in a portion in the circumferential direction, and a third cutting portion 423 serving as a cutting edge is disposed in the edge portion of the third cutout portion 422. Only one third cutout portion 422 may be disposed in the circumferential direction, or two or more third cutout portions 422 may be disposed. The third cutout portion 422 and the third cutting portion 423 are also continuously formed in the stepped portion 415 and the second cylindrical portion 412.

The second tapered portion 414 and the third tapered portion 416 interlock with each other so that the outer peripheral surface has a V-shape in a longitudinal section passing through the central axis. An angle θ1 of the second tapered portion 414 with respect to the axially orthogonal cross section is equal to or smaller than an angle θ2 of the third tapered portion 416 with respect to the axially orthogonal cross section. Therefore, the third cutting portion 423 of the third tapered portion 416 is disposed in a wider range than the second cutting portion 421 of the second tapered portion 414. The third cutting portion 423 of the third tapered portion 416 mainly cuts the object when the treatment device 401 is pushed forward, and the second cutting portion 421 of the second tapered portion 414 mainly cuts the object when the treatment device 401 is pulled back. Normally, compared to when the treatment device 401 is pulled back, when the treatment device 401 is pushed forward, much more objects need to be cut. Accordingly, a shape suitable for the cutting can be obtained by setting the angle θ1 to be equal to or smaller than the angle θ2.

The rotary structure 410 material is not particularly limited. However, for example, the rotary structure 410 material is preferably stainless steel, Ta, Ti, Pt, Au, W, polyolefin such as polyethylene and polypropylene, polyester such as polyamide and polyethylene terephthalate, a fluorine-based polymer such as ETFE, polyether ether ketone (PEEK), or polyimide.

The outer sheath 430 rotatably accommodates the second cylindrical portion 412 of the rotary structure 410 in the distal side end portion. The second non-cutting portion 431 is disposed on the outer peripheral surface on the distal side of the outer sheath 430.

The outer sheath 430 material is not particularly limited. However, for example, the outer sheath material can be a polyolefin such as polyethylene and polypropylene, polyester such as polyamide and polyethylene terephthalate, a fluorine-based polymer such as ETFE, polyether ether ketone (PEEK), or polyimide. In addition, the outer sheath 430 may be formed of a plurality of materials, and the reinforcement member such as the wire rod may be incorporated in the plurality of materials of the outer sheath 430.

The bearing 440 is located between the outer sheath 430 and the drive shaft 60. Since the bearing 440 is provided, the drive shaft 60 and the rotary structure 410 are smoothly rotatable relative to the outer sheath 430.

The first cutting portion 418 is located inside the tangential line L between the first non-cutting portion 424 and the second non-cutting portion 419. In addition, the second cutting portion 421 and the third cutting portion 423 are located inside the tangential line L between the first non-cutting portion 424 and the second non-cutting portion 431.

Figure 44A:
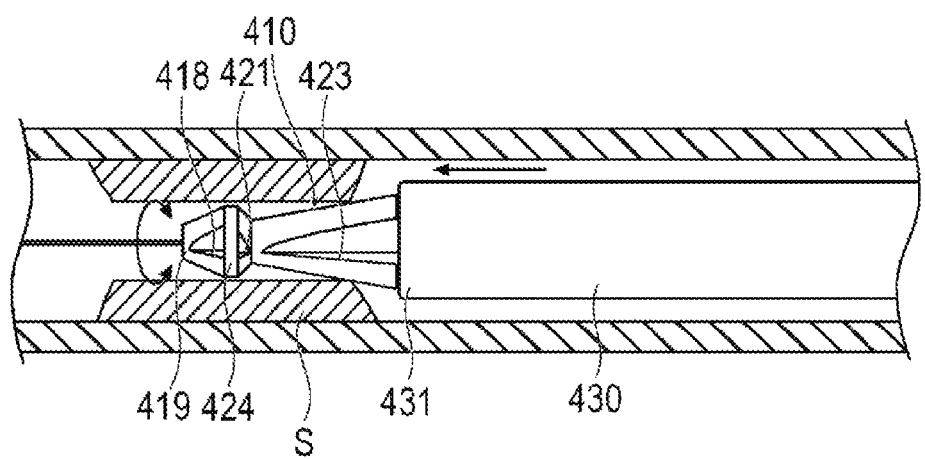

When the stenosed site S inside the blood vessel is cut using the medical device 400 according to the fifteenth embodiment, the treatment device 401 is inserted into the blood vessel. Next, if the drive shaft 60 is rotated, as illustrated in FIG. 44A, the first cutting portion 418, the second cutting portion 421, and the third cutting portion 423 of the rotary structure 410 are rotated, and the stenosed site S inside the biological lumen can be cut. In this case, the first cutting portion 418 is located inside the tangential line L between the first non-cutting portion 424 and the second non-cutting portion 419. Accordingly, the first cutting portion 418 is prevented from coming into contact with the biological tissue. Therefore, the relative safety of the medical device and treatment method can be improved. In addition, the second cutting portion 421 and the third cutting portion 423 are located inside the tangential line L between the first non-cutting portion 424 and the second non-cutting portion 431. Accordingly, the second cutting portion 421 and the third cutting portion 423 can be prevented from coming into contact with the biological tissue. Therefore, the relative safety of the medical device and treatment method can be improved.

Figure 44B:
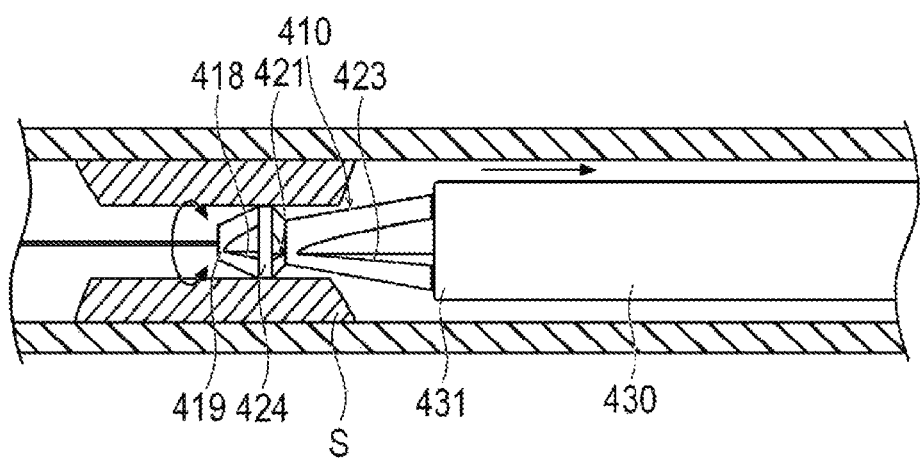

In addition, the first cutting portion 418 and the third cutting portion 423 are formed in the tapered portion whose diameter decreases toward the distal side. Accordingly, when the treatment device 401 is pushed forward to the distal side, the stenosed site S can be effectively cut. Furthermore, the second cutting portion 421 is formed in the tapered portion whose diameter decreases toward the proximal side. Accordingly, when the treatment device 401 is pulled back to the proximal side as illustrated in FIG. 44B, the stenosed site S can be effectively cut.

As described above, between the first non-cutting portion 424 and the second non-cutting portion 431, the medical device 400 according to the fifteenth embodiment has the second cutting portion 421 whose diameter decreases toward the proximal side, and the third cutting portion 423 whose diameter decreases toward the distal side. Therefore, in both the case where the treatment device 401 is pushed forward and the case where the treatment device 401 is pulled back, the second cutting portion 421 and the third cutting portion 423 which are disposed between the first non-cutting portion 424 and the second non-cutting portion 431 can safely and effective cut the object such as the stenosed site S.

Sixteenth Embodiment

Figure 45:
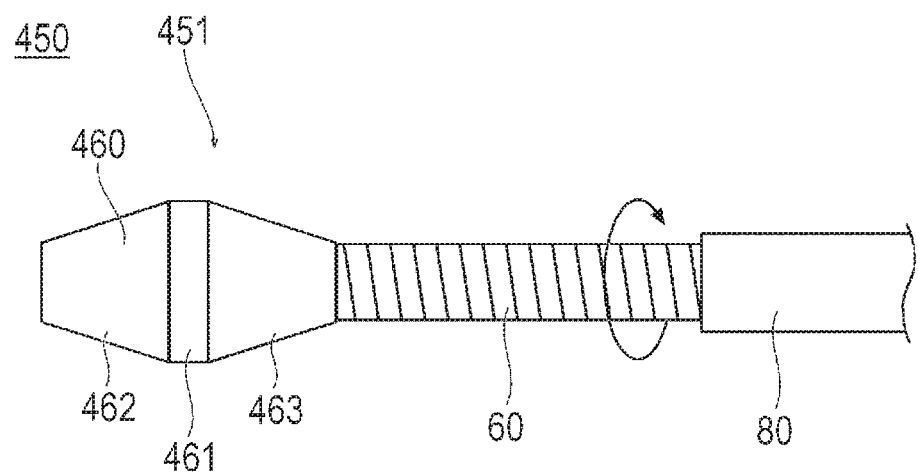
FIG. 45 is a plan view illustrating a treatment device of a medical device according to a sixteenth embodiment.

A medical device 450 according to a sixteenth embodiment of the present disclosure is different from that according to the fifth embodiment in that a structure of the rotary structure 460 is different as illustrated in FIG. 45. The same reference numerals will be given to elements having functions which are the same as those according to the first and fifth embodiments, and description of the of the reference number, elements, and functions will be omitted.

A treatment device 451 of the medical device 450 according to the sixteenth embodiment includes a rotatable rotary structure 460, the drive shaft 60 for rotating the rotary structure 460, the outer sheath 80 capable of rotatably accommodating the drive shaft 60, and the operation unit 210 (refer to FIG. 23) disposed on the hand side for operation. The rotary structure 460 and the drive shaft 60 internally have a guide wire lumen.

The rotary structure 460 has a non-cutting portion 461 having a smooth outer peripheral surface, a first cutting portion 462 located on the distal side of the non-cutting portion 461, and a second cutting portion 463 located on the proximal side of the non-cutting portion 461. The non-cutting portion 461 is the largest outer diameter portion (maximum outer diameter portion) in the rotary structure 460, and the outer peripheral surface is formed in a smooth cylindrical shape. The diameter of the first cutting portion 462 decreases in a tapered shape from the non-cutting portion 461 toward the distal side. The diameter of the second cutting portion 463 decreases in a tapered shape from the non-cutting portion 461 toward the proximal side.

Figure 46:
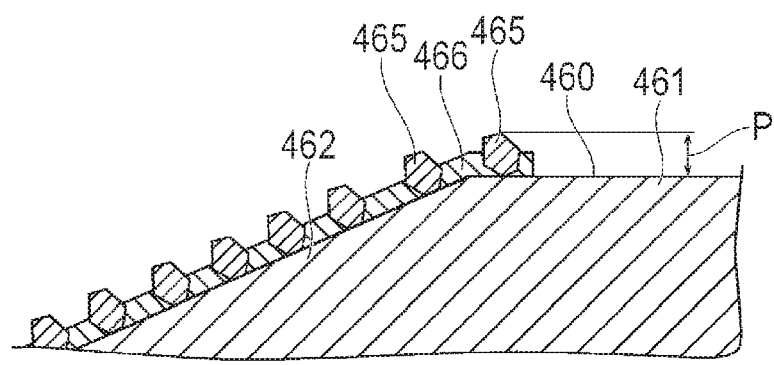
FIG. 46 is an enlarged cross-sectional view of a surface of a rotary structure unit of the medical device according to the sixteenth embodiment.

As illustrated in FIG. 46, a polishing material 465 such as a diamond particle is fixed to each outer surface of the first cutting portion 462 and the second cutting portion 463 by a fixing layer 466 such as a nickel plating layer. Therefore, the fixing layer 466 and an abrasive grain 465 whose outer diameter is larger than that of the non-cutting portion 461 can be present in a portion where the first cutting portion 462 and the second cutting portion 463 are adjacent to the non-cutting portion 461. However, an extremely small amount is provided for the abrasive grain 465 and the fixing layer 466 which have the larger outer diameter than that of the non-cutting portion 461, and a protrusion amount P is also small. Accordingly, both of these contribute to polishing in an extremely limited small range. The protrusion amount P of the abrasive grain 465 and the fixing layer 466 which protrude outward in the radial direction from the non-cutting portion 461 is 100 μm or smaller, for example. It is preferable that the protrusion amount P is 30 μm or smaller, and more preferably 20 μm or smaller. Therefore, the maximum outer diameter portion of the rotary structure unit 460 configured so that the abrasive grain 465 or the fixing layer 466 protrudes beyond the non-cutting portion 461 is substantially the non-cutting portion 461.

Figure 47:
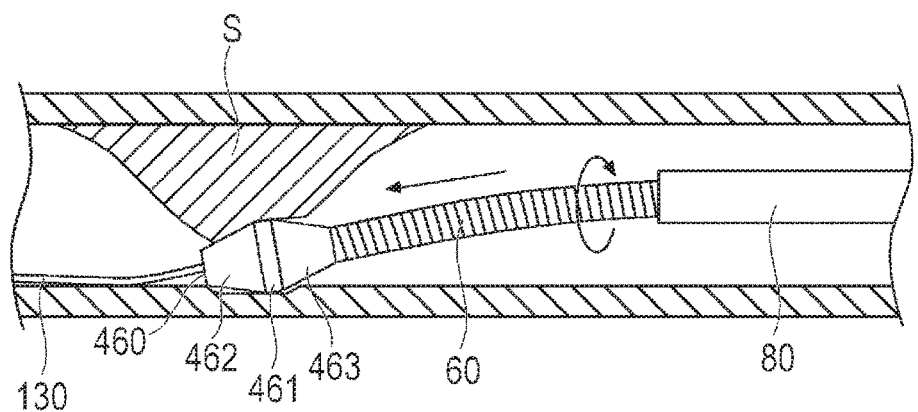
FIG. 47 is a schematic cross-sectional view illustrating an intravascular state when a medical procedure is performed using the medical device according to the sixteenth embodiment.

When the stenosed site S inside the blood vessel is cut using the medical device 450 according to the sixteenth embodiment, the treatment device 451 is inserted into the blood vessel. In a case where the stenosed site S is biased in the circumferential direction of the blood vessel as illustrated in FIG. 47, if the drive shaft 60 is rotated and pushed forward, the first cutting portion 462 of the rotary structure 460 comes into contact with the stenosed site S and blood vessel. Therefore, the first cutting portion 462 cuts not only the stenosed site S but also the blood vessel. However, the non-cutting portion 461 having the largest outer diameter comes into smooth contact with the blood vessel. Accordingly, a possibility of vascular perforation can be reduced by reducing the damage to the blood vessel which is caused by the first cutting portion 462 having the smaller outer diameter than that of the non-cutting portion 461. Thereafter, forward-rearward movement of the rotary structure 460 is repeatedly performed. In this manner, while the non-cutting portion 461 helps prevent the blood vessel from being damaged, the first cutting portion 462 and the second cutting portion 463 can effectively cut the stenosed site S. The diameter of the first cutting portion 462 decreases toward the distal side. Accordingly, when the treatment device 451 is pushed forward to the distal side, the stenosed site S can be effectively cut. The diameter of the second cutting portion 462 decreases toward the proximal side. Accordingly, when the treatment device 451 is pulled back to the proximal side, the stenosed site S can be effectively cut.

As described above, the medical device 450 according to the sixteenth embodiment is a device for cutting the object inside the biological lumen, and includes the rotatable drive shaft 60, and the rotary structure 460 interlocking with the distal side of the drive shaft 60 and rotated by the drive shaft 60. The rotary structure 460 has the first cutting portion 462 and the second cutting portion 463 for cutting the object, and the non-cutting portion 461 which can come into smooth contact with the biological tissue. The non-cutting portion 461 is located in the maximum outer diameter portion of the rotary structure 460. In the medical device 450 configured as described above, the non-cutting portion 461 is located in the maximum outer diameter portion of the rotary structure 460. Accordingly, while the rotating first cutting portion 462 and the rotating second cutting portion 463 effectively cut the object inside the biological lumen, the non-cutting portion 461 can minimize the damage of the biological tissue which may be caused by the first cutting portion 462 and the second cutting portion 463. Therefore, the relative safety of the medical device and treatment method can be improved by reducing the damage to the biological tissue.

In addition, according to the present disclosure, there is also provided the treatment method for cutting the object inside the biological lumen. The treatment method is used in order to cut the object inside the biological lumen by using the above-described medical device 450. The treatment method has a step of inserting the rotary structure 460 into the biological lumen, a step of rotating the rotary structure 460 and cutting the object inside the biological lumen by using the first cutting portion 462 and the second cutting portion 463 while bringing the non-cutting portion 461 into contact with the biological tissue, and a step of removing the rotary structure 460 from the inside of the biological lumen. According to the treatment method, in the cutting step, the non-cutting portion 461 located in the maximum outer diameter portion of the rotary structure 460 comes into contact with the biological tissue. Accordingly, while the first cutting portion 462 and the second cutting portion 463 effectively cut the object inside the biological lumen, the non-cutting portion 461 can minimize the damage to the biological tissue which may be caused by the first cutting portion 462 and the second cutting portion 463. Therefore, the relative safety of the medical device and treatment can be improved by reducing the damage to the biological tissue.

The present disclosure is not limited to the above-described embodiments, and within the technical idea of the present disclosure, the present disclosure can be modified in various ways by the person skilled in the art. For example, the biological lumen into which the medical device is inserted is not limited to the blood vessel. For example, the biological lumen may be a vessel, a ureter, a bile duct, a fallopian duct, or a hepatic duct.

In addition, according to the first embodiment, the first non-cutting portion 56 is expandable. However, the second non-cutting portion may also be expandable. For example, in order to enable the first non-cutting portion and the second non-cutting portion to be expanded, the first non-cutting portion and the second non-cutting portion may be formed using a balloon which is inflated by injecting the fluid into the balloon.

In addition, the collecting device may not be the mechanism for collecting the debris by using the filter. Alternatively, other mechanisms (for example, an aspirating mechanism) which can collect the fallen debris may be provided. Alternatively, the medical device may not include the collecting device for collecting the debris.

The detailed description above describes a medical device and a treatment method for cutting an object from an inner wall surface of a biological lumen. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for cutting an object inside a biological lumen, the medical device comprising:
   a rotatable drive shaft;
   a rotary structure configured to interlock with a distal side of the drive shaft so as to be rotated by the drive shaft;
   the rotary structure having a cutting portion configured to cut the object, and a non-cutting portion capable of coming into contact with a biological tissue, and wherein the non-cutting portion is located in a maximum outer diameter portion of the rotary structure;
   the non-cutting portion including a first non-cutting portion and a second non-cutting portion, the first non-cutting portion being proximal to the second non-cutting portion and wherein an outer diameter of the first non-cutting portion is larger in a radial direction than an outer diameter of the second non-cutting portion and an outer diameter of a proximal portion of the cutting portion is larger in the radial direction than an outer diameter of a distal portion of the cutting portion;
   wherein the cutting portion of the rotary structure includes a tapered cutting portion disposed on a distal side of the first non-cutting portion, the tapered cutting portion tapering towards the second non-cutting portion of the rotary structure, the tapered cutting portion being interposed between the first non-cutting portion and the second non-cutting portion along an axial direction, and the tapered cutting portion is located inside a tangential line between the first non-cutting portion and the second non-cutting portion in a cross section along the axial direction; and
   a distal tapered portion disposed on a distal side of the second non-cutting portion, the distal tapered portion tapering in a conical shape towards a distal end of the rotary structure.

2. The medical device according to claim 1, further comprising:
   an outer sheath configured to accommodate the drive shaft so as to be relatively rotatable.

3. The medical device according to claim 2, wherein the outer sheath is movable relative to the drive shaft along the axial direction.

4. The medical device according to claim 1, wherein the tapered cutting portion has a cutout portion.

5. The medical device according to claim 4, wherein the cutout portion communicates from the tapered cutting portion to the first non-cutting portion.

6. The medical device according to claim 5, further comprising:
   a proximal portion of the cutout portion is larger in a circumferential direction than a distal portion of the cutout portion.

7. The medical device according to claim 1, further comprising:
   a proximal tapered portion disposed on a proximal side of the first non-cutting portion.

8. The medical device according to claim 1, wherein an angle to a central axis of the rotary structure of the distal tapered portion is greater than an angle to the central axis of the rotary structure of the tapered cutting portion.

9. A treatment method for cutting an object inside a biological lumen with a medical device, the medical device including a rotatable drive shaft, a rotary structure that interlocks with a distal side of the drive shaft so as to be rotated by the drive shaft, and the rotary structure having a cutting portion for cutting the object, and a non-cutting portion capable of coming into contact with a biological tissue, and wherein the non-cutting portion is located in a maximum outer diameter portion of the rotary structure, the non-cutting portion having a first non-cutting portion and a second non-cutting portion, the first non-cutting portion being proximal to the second non-cutting portion and wherein an outer diameter of the first non-cutting portion is larger in a radial direction than an outer diameter of the second non-cutting portion and an outer diameter of a proximal portion of the cutting portion is larger in the radial direction than an outer diameter of a distal portion of the cutting portion, wherein the cutting portion of the rotary structure includes a tapered cutting portion disposed on a distal side of the first non-cutting portion, the tapered cutting portion tapering towards the second non-cutting portion of the rotary structure, and a distal tapered portion disposed on a distal side of the second non-cutting portion, the distal tapered portion tapering in a conical shape towards a distal end of the rotary structure, the tapered cutting portion being interposed between the first non-cutting portion and the second non-cutting portion along an axial direction, and the tapered cutting portion is located inside a tangential line between the first non-cutting portion and the second non-cutting portion in a cross section along the axial direction, the method comprising:

inserting the rotary structure into the biological lumen; and causing the tapered cutting portion to cut the object inside the biological lumen while the rotary structure is rotated and the first non-cutting portion and the second non-cutting portion are brought into contact with the biological tissue.

10. The treatment method according to claim 9, further comprising:

inclining the tapered cutting portion and the distal tapered portion inside the biological lumen while the object is being cut.

11. The treatment method according to claim 9, comprising:

moving a rotational center axis of the rotary structure so as to swing the rotary structure inside the biological lumen.

12. The treatment method according to claim 9, comprising:

rotating a proximal portion of an outer sheath which is capable of accommodating the drive shaft and whose distal portion is curved to adjust a position and inclination of the rotary structure inside the biological lumen.

13. The treatment method according to claim 9, comprising:

moving an outer sheath which is capable of accommodating the drive shaft relative to the rotary structure in the axial direction to adjust a position and an inclination of the rotary structure inside the biological lumen.

14. A medical device for cutting an object inside a biological lumen, the medical device comprising:

a rotatable drive shaft;

a rotary structure configured to interlock with a distal side of the drive shaft so as to be rotated by the drive shaft;

the rotary structure having a cutting portion configured to cut the object, and a non-cutting portion capable of coming into contact with a biological tissue, and wherein the non-cutting portion is located in a maximum outer diameter portion of the rotary structure;

the non-cutting portion includes a first non-cutting portion and a second non-cutting portion, the first non-cutting portion being proximal to the second non-cutting portion and wherein an outer diameter of the first non-cutting portion is larger in a radial direction than an outer diameter of the second non-cutting portion and an outer diameter of a proximal portion of the cutting portion is larger in the radial direction than an outer diameter of a distal portion of the cutting portion;

the cutting portion of the rotary structure includes a tapered cutting portion disposed on a distal side of the first non-cutting portion, the tapered cutting portion tapering towards the second non-cutting portion of the rotary structure, the tapered cutting portion being interposed between the first non-cutting portion and the second non-cutting portion along an axial direction, and the tapered cutting portion is located inside a tangential line between the first non-cutting portion and the second non-cutting portion in a cross section along the axial direction; and a distal tapered portion disposed on a distal side of the second non-cutting portion, the distal tapered portion tapering in a conical shape towards a distal end of the rotary structure, and a proximal tapered portion on a proximal side of the first non-cutting portion, the proximal tapered portion tapering towards a proximal side of the rotary structure.

15. The medical device according to claim 14, wherein an angle to a central axis of the rotary structure of the distal tapered portion is greater than an angle to the central axis of the rotary structure of the tapered cutting portion.

16. The medical device according to claim 14, further comprising:

an outer sheath configured to accommodate the drive shaft so as to be relatively rotatable.

17. The medical device according to claim 16, wherein the outer sheath is movable relative to the drive shaft along the axial direction.

* * * * *